United States Patent
Chen et al.

(10) Patent No.: US 7,592,337 B2
(45) Date of Patent: Sep. 22, 2009

(54) DI-ARYL SUBSTITUTED TETRAZOLE MODULATORS OF METABOTROPIC GLUTAMATE RECEPTOR-5

(75) Inventors: Chixu Chen, San Diego, CA (US); Nicholas D. P. Cosford, San Diego, CA (US); Brian W. Eastman, San Diego, CA (US); Dehua Huang, San Diego, CA (US); Steve F. Poon, San Diego, CA (US); Thomas S. Reger, San Diego, CA (US); Jeffrey R. Roppe, Temecula, CA (US); Nicholas D. Smith, San Diego, CA (US)

(73) Assignee: Merck & Co., Inc., Rahway, NJ (US)

( * ) Notice: Subject to any disclaimer, the term of this patent is extended or adjusted under 35 U.S.C. 154(b) by 786 days.

(21) Appl. No.: 10/506,479

(22) PCT Filed: Mar. 7, 2003

(86) PCT No.: PCT/US03/07074

§ 371 (c)(1),
(2), (4) Date: Sep. 1, 2004

(87) PCT Pub. No.: WO03/077918

PCT Pub. Date: Sep. 25, 2003

(65) Prior Publication Data

US 2005/0153986 A1    Jul. 14, 2005

Related U.S. Application Data

(60) Provisional application No. 60/363,456, filed on Mar. 12, 2002.

(51) Int. Cl.
| | |
|---|---|
| *A61K 31/535* | (2006.01) |
| *A61K 31/4965* | (2006.01) |
| *A61K 31/44* | (2006.01) |
| *A61K 31/47* | (2006.01) |
| *A61K 31/425* | (2006.01) |
| *A61K 31/41* | (2006.01) |
| *A61K 31/415* | (2006.01) |
| *A61K 31/385* | (2006.01) |
| *A61K 31/38* | (2006.01) |
| *A61K 31/335* | (2006.01) |
| *A61K 31/34* | (2006.01) |
| *C07D 413/00* | (2006.01) |
| *C07D 239/00* | (2006.01) |
| *C07D 241/00* | (2006.01) |
| *C07D 221/02* | (2006.01) |
| *C07D 421/00* | (2006.01) |
| *C07D 277/04* | (2006.01) |

(52) U.S. Cl. .............................. 514/236.2; 514/255.05; 514/256; 514/299; 514/314; 514/336; 514/365; 514/381; 514/406; 514/436; 514/444; 514/463; 514/468; 544/111; 544/242; 544/336; 546/112; 546/268.1; 548/146; 548/250; 548/255; 548/356.1; 549/17; 549/59; 549/472

(58) Field of Classification Search ............. 514/236.2, 514/255.05, 256, 299, 314, 336, 365, 381, 514/406, 436, 444, 463, 468; 544/111, 242, 544/336; 546/112, 268.1; 548/146, 250, 548/255, 356.1; 549/17, 59, 472

See application file for complete search history.

(56) References Cited

U.S. PATENT DOCUMENTS

| | | |
|---|---|---|
| 6,660,753 B2 | 12/2003 | Van Wagenen et al. |
| 7,087,601 B2 | 8/2006 | Arruda et al. |
| 7,105,548 B2 | 9/2006 | Cosford et al. |
| 7,112,595 B2 | 9/2006 | Wagenen et al. |
| 7,253,190 B2 | 8/2007 | Cosford et al. |
| 7,268,151 B2 | 9/2007 | Cosford et al. |
| 2005/0026963 A1 | 2/2005 | Cosford et al. |
| 2005/0085514 A1 | 4/2005 | Cosford et al. |
| 2006/0189681 A1 | 8/2006 | Wagenen et al. |
| 2006/0193926 A1 | 8/2006 | Cosford et al. |
| 2006/0194807 A1 | 8/2006 | Cosford et al. |
| 2006/0217420 A1 | 9/2006 | Cosford et al. |
| 2007/0027321 A1 | 2/2007 | Kamenecka et al. |
| 2007/0149547 A1 | 6/2007 | Bonnefous et al. |

OTHER PUBLICATIONS

Caplus Accession No. 1986:11139, Kitaeva, et al. Radioprotective and antitumor activity of some tetrazole derivatives Khimiko-Farmatsecticheskii Zhurnal (1986), vol. 20, No. 5, pp. 559-63.

*Primary Examiner*—Rei-Tsang Shiao
*Assistant Examiner*—Joseph R Kosack
(74) *Attorney, Agent, or Firm*—J. Eric Thies; William Krovatin

(57) ABSTRACT

Tetrazole compounds substituted directly, or by a bridge, with i) a heteroaryl moiety containing N adjacent to the point of connection of the heteroaryl and ii) another heteroaryl or aryl ring, with at least one of the rings being further substituted with another ring, are mGluR5 modulators useful in the treatment of psychiatric and mood disorders such as, for example, schizophrenia, anxiety, depression, panic, and bipolar disorder, as well as in the treatment of pain, Parkinson's disease, cognitive dysfunction, epilepsy, circadian rhythm disorders, drug addiction, drug abuse, drug withdrawal, obesity and other diseases.

9 Claims, No Drawings

DI-ARYL SUBSTITUTED TETRAZOLE MODULATORS OF METABOTROPIC GLUTAMATE RECEPTOR-5

RELATED APPLICATION DATA

This is a National filing under 35 USC 371 of PCT/US03/07074, filed Mar. 7, 2003, which claims priority from U.S. Ser. No. 60/363,456, filed Mar. 12, 2002.

BACKGROUND OF THE INVENTION

1. Field of the Invention

The present invention is directed to tetrazole compounds substituted with i) a heteroaryl ring and ii) another heteroaryl or aryl ring with at least one of the rings being further substituted with another ring. In particular, this invention is directed to tetrazole compounds substituted directly, or by a bridge, with i) a heteroaryl moiety containing N adjacent to the point of connection of the heteroaryl and ii) another heteroaryl or aryl ring, with at least one of the rings being further substituted with another ring, which are metabotropic glutamate receptor—subtype 5 ("mGluR5") modulators useful in the treatment of psychiatric and mood disorders such as, for example, schizophrenia, anxiety, depression, panic, bipolar disorder, and circadian rhythm disorders, as well as in the treatment of pain, Parkinson's disease, cognitive dysfunction, epilepsy, drug addiction, drug abuse, drug withdrawal, obesity and other diseases.

2. Related Background

A major excitatory neurotransmitter in the mammalian nervous system is the glutamate molecule, which binds to neurons, thereby activating cell surface receptors. Such surface receptors are characterized as either ionotropic or metabotropic glutamate receptors. The metabotropic glutamate receptors ("mGluR") are G protein-coupled receptors that activate intracellular second messenger systems when bound to glutamate. Activation of mGluR results in a variety of cellular responses. In particular, mGluR1 and mGluR5 activate phospholipase C, which is followed by mobilizing intracellular calcium.

Modulation of metabotropic glutamate receptor subtype 5 (mGluR5) is useful in the treatment of diseases that affect the nervous system (see for example W. P. J. M Spooren et al., *Trends Pharmacol. Sci.*, 22:331-337 (2001) and references cited therein). For example, recent evidence demonstrates the involvement of mGluR5 in nociceptive processes and that modulation of mGluR5 using mGluR5-selective compounds is useful in the treatment of various pain states, including acute, persistent and chronic pain [K Walker et al., *Neuropharmacology*, 40:1-9 (2001); F. Bordi, A. Ugolini *Brain Res.*, 871:223-233 (2001)], inflammatory pain [K Walker et al., *Neuropharmacology*, 40:10-19 (2001); Bhave et al. *Nature Neurosci.* 4:417423 (2001)] and neuropathic pain [Dogrul et al. *Neurosci. Lett.* 292:115-118 (2000)].

Further evidence supports the use of modulators of mGluR5 in the treatment of psychiatric and neurological disorders. For example, mGluR5-selective compounds such as 2-methyl-6-(phenylethynyl)-pyridine ("MPEP") are effective in animal models of mood disorders, including anxiety and depression [W. P. J. M Spooren et al., *J. Pharmacol. Exp. Ther.*, 295:1267-1275 (2000); E. Tatarczynska et al, *Brit. J. Pharmacol.*, 132:1423-1430 (2001); A. Klodzynska et al, *Pol. J. Pharmacol.*, 132:1423-1430 (2001)]. Gene expression data from humans indicate that modulation of mGluR5 may be useful for the treatment of schizophrenia [T. Ohnuma et al, *Mol. Brain. Res.*, 56:207-217 (1998); ibid, *Mol. Brain. Res.*, 85:24-31 (2000)]. Studies have also shown a role for mGluR5, and the potential utility of mGluR5-modulatory compounds, in the treatment of movement disorders such as Parkinson's disease [W. P. J. M Spooren et al., *Europ. J. Pharmacol.* 406:403-410 (2000); H. Awad et al., *J. Neurosci.* 20:7871-7879 (2000); K. Ossawa et al. *Neuropharmacol.* 41:413-420 (2001)]. Other research supports a role for mGluR5 modulation in the treatment of cognitive dysfunction [G. Riedel et al, *Neuropharmacol.* 39:1943-1951 (2000)], epilepsy [A. Chapman et al, *Neuropharmacol.* 39:1567-1574 (2000)] and neuroprotection [V. Bruno et al, *Neuropharmacol.* 39:2223-2230 (2000)]. Studies with mGluR5 knockout mice and MPEP also suggest that modulation of these receptors may be useful in the treatment of drug addiction, drug abuse and drug withdrawal [C. Chiamulera et al. *Nature Neurosci.* 4:873-874 (2001)].

International Patent Publications WO 01/12627 and WO 99/26927 describe heteropolycyclic compounds and their use as metabotropic glutamate receptor antagonists.

U.S. Pat. No. 3,647,809 describes pyridyl-1,2,4-oxadiazole derivatives. U.S. Pat. No. 4,022,901 describes 3-pyridyl-5-isothiocyanophenyl oxadiazoles. International Patent Publication WO 98/17652 describes oxadiazoles, WO 97/03967 describes various substituted aromatic compounds, JP 13233767A and WO 94/22846 describe various heterocyclic compounds.

Compounds that include ringed systems are described by various investigators as effective for a variety of therapies and utilities. For example, International Patent Publication No. WO 98/25883 describes ketobenzamides as calpain inhibitors, European Patent Publication No. EP 811610 and U.S. Pat. Nos. 5,679,712, 5,693,672 and 5,747,541 describe substituted benzoylguanidine sodium channel blockers, and U.S. Pat. No. 5,736,297 describes ring systems useful as a photosensitive composition.

However, there remains a need for novel compounds and compositions that therapeutically inhibit mGluR5 with minimal side effects.

SUMMARY OF THE INVENTION

The present invention is directed to novel tetrazole compounds substituted directly, or by a bridge, with i) a heteroaryl moiety containing N adjacent to the point of connection of the heteroaryl and ii) another heteroaryl or aryl ring, with at least one of the rings being further substituted with another ring, which are metabotropic glutamate receptor—subtype 5 modulators useful in the treatment of psychiatric and mood disorders such as, for example, schizophrenia, anxiety, depression, bipolar disorders, and panic, as well as in the treatment of pain, Parkinson's disease, cognitive dysfunction, epilepsy, circadian rhythm and sleep disorders—such as shift-work induced sleep disorder and jet-lag, drug addiction, drug abuse, drug withdrawal, obesity and other diseases. This invention also provides a pharmaceutical composition which includes an effective amount of the novel tetrazole compounds substituted with a heteroaryl moiety, and a pharmaceutically acceptable carrier.

This invention further provides a method of treatment of psychiatric and mood disorders such as, for example, schizophrenia, anxiety, depression, panic, bipolar disorders, and circadian rhythm and sleep disorders, as well as a method of treatment of pain, Parkinson's disease, cognitive dysfunction, epilepsy, obesity, drug addiction, drug abuse and drug withdrawal by the administration of an effective amount of the novel tetrazole compounds substituted with a heteroaryl moiety.

DETAILED DESCRIPTION OF THE INVENTION

The compounds of the present invention are represented by Formula (I):

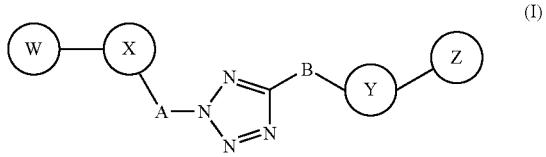

or a pharmaceutically acceptable salt thereof, wherein

X and Y each independently is aryl or heteroaryl wherein at least one of X and Y is a heteroaryl with N adjacent to the position of attachment to A or B respectively;

X is optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^1$, $R^2$, and $R^3$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$S_{O_2}$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

W is —$C_{3-7}$cycloalkyl, -hetero$C_{3-7}$cycloalkyl, —$C_{0-6}$alkylaryl, or —$C_{0-6}$alkylheteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents;

Y is optionally substituted with 1-7 independent halogen, —CN, $NO_2$, —$C_{1-6}$alkyl, —$C_{1-6}$alkenyl, —$C_{1-6}$alkynyl, —$OR^5$, —$NR^5R^6$, —$C(=NR^5)NR^6R^7$, —$N(=NR^5)NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —$C(=NR^5)R^6$, or —$C(=NOR^5)R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{1-6}$alkyl), —($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{1-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

Z is —$C_{3-7}$cycloalkyl, -hetero$C_{3-7}$cycloalkyl, —$C_{0-6}$alkylaryl, or —$C_{0-6}$alkylheteroaryl optionally substituted with 1-7 independent halogen, —CN, $N_{0-2}$, —$C_{0-6}$alkyl, —$C_{1-6}$alkenyl, —$C_{1-6}$alkynyl, —$OR^1$, -$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents;

one of W and Z is optionally absent; and any N may be an N-oxide.

In one aspect, the compounds of this invention are represented by Formula (I) or a pharmaceutically acceptable salt thereof, wherein X is 2-pyridyl optionally substituted with 1-4 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^1$, $R^2$, and $R^3$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$CO_{0-2}$alkyl-$NR^9CO$—$C_{0-2}$alkyl-, —$C_{0-2}$alkyl-$NR^9SO_2$—$C_{0-2}$alkyl- or -hetero$C_{0-4}$alkyl;

W is —$C_{3-7}$cycloalkyl, -hetero$C_{3-7}$cycloalkyl, —$C_{0-6}$alkylaryl, or —$C_{0-6}$alkylheteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents;

Y is aryl or heteroaryl optionally substituted with 1-7 independent halogen, —CN, $NO_2$, —$C_{1-6}$alkyl, —$C_{1-6}$alkenyl, —$C_{1-6}$alkynyl, —$OR^5$, —$NR^5R^6$, —C(=$NR^5$)$NR^6R^7$, —N(=$NR^5$)$NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —C(=$NR^5$)$R^6$, or —C(=$NOR^5$)$R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}CO$—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

Z is —$C_{3-7}$cycloalkyl, -hetero$C_{3-7}$cycloalkyl, —$C_{0-6}$alkylaryl, or —$C_{0-6}$alkylheteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents;

one of W and Z is optionally absent; and any N may be an N-oxide.

In an embodiment of this one aspect, the compounds of this invention are represented by Formula (I) or a pharmaceutically acceptable salt thereof, wherein X is 2-pyridyl optionally substituted with 1-4 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^1$, $R^2$, and $R^3$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9CO$—$C_{0-2}$alkyl-, —$C_{0-2}$alkyl-$NR^9SO_2$—$C_{0-2}$alkyl- or -hetero$C_{0-4}$alkyl;

W is —$C_{3-7}$cycloalkyl, -hetero$C_{3-7}$cycloalkyl, —$C_{0-6}$alkylaryl, or —$C_{0-6}$alkylheteroaryl optionally substituted with 1-7 independent halogen, —CN, $N_{0-2}$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents;

Y is phenyl optionally substituted with 1-5 independent halogen, —CN, $NO_2$, —$C_{1-6}$alkyl, —$C_{1-6}$alkenyl, —$C_{1-6}$alkynyl, —$OR^5$, —$NR^5R^6$, —C(=$NR^5$)$NR^6R^7$, —N(=$NR^5$)$NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —C(=$NR^5$)$R^6$, or —C(=$NOR^5$)$R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}CO$—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

Z is —$C_{3-7}$cycloalkyl, -hetero$C_{3-7}$cycloalkyl, —$C_{0-6}$alkylaryl, or —$C_{0-6}$alkylheteroaryl optionally substituted with 1-7 independent halogen, —CN, $N_{0-2}$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR1R^2$, —$COR^1$, —$CO_2R^1$, —$CONR^1R^2$, —$C(=NR^1)R^2$, or —$C(=NOR^1)R^2$ substituents;

one of W and Z is optionally absent; and any N may be an N-oxide.

In a second aspect, the compounds of this invention are represented by Formula (I) or a pharmaceutically acceptable salt thereof, wherein X is aryl or heteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR1R^2$, —$COR^1$, —$CO_2R^1$, —$CONR^1R^2$, —$C(=NR^1)R^2$, or —$C(=NOR^1)R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}alkyl)$, —$O(C_{3-7}cycloalkyl)$, —$O(aryl)$, —$N(C_{0-6}alkyl)(C_{0-6}alkyl)$, —$N(C_{0-6}alkyl)(C_{3-7}cycloalkyl)$, or —$N(C_{0-6}alkyl)(aryl)$ groups;

$R^1$, $R^2$, and $R^3$ each independently is —$C_{0-6}$alkyl, —$C_{3-7}$cycloalkyl, heteroaryl, or aryl; any of which is optionally substituted with 1-5 independent halogen, —CN, —$C^{1-6}$alkyl, —$O(C_{0-6}alkyl)$, —$O(C_{3-7}cycloalkyl)$, —$O(aryl)$, —$N(C_{0-6}alkyl)(C_{0-6}alkyl)$, —$N(C_{0-6}alkyl)(C_{3-7}cycloalkyl)$, —$N(C_{0-6}alkyl)(aryl)$ substituents;

$R^4$ is —$C_{1-6}$alkyl, —$C_{3-7}$cycloalkyl, heteroaryl, or aryl; optionally substituted with 1-5 independent halogen, —CN, —$C_{1-6}$alkyl, —$O(C_{0-6}alkyl)$, —$O(C_{3-7}cycloalkyl)$, —$O(aryl)$, —$N(C_{0-6}alkyl)(C_{0-6}alkyl)$, —$N(C_{0-6}alkyl)(C_{3-7}cycloalkyl)$, —$N(C_{0-6}alkyl)(aryl)$ substituents;

A is —$C_{0-4}$alkyl, —$C_{0-2}$alkyl-SO—$C_{0-2}$alkyl-, —$C_{0-2}$alkyl-$S_{0-2}$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

W is —$C_{3-7}$cycloalkyl, -hetero$C_{3-7}$cycloalkyl, —$C_{0-6}$alkylaryl, or —$C_{0-6}$alkylheteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents;

Y is 2-pyridyl optionally substituted with 1-4 independent halogen, —CN, $NO_2$, —$C_{1-6}$alkyl, —$C_{1-6}$alkenyl, —$C_{1-6}$alkynyl, —$OR^5$, —$NR^5R^6$, —$C(=NR^5)NR^6R^7$, —$N(=NR^5)NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —$C(=NR^5)R^6$, or —$C(=NOR^5)R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}alkyl)$, —$O(C_{3-7}cycloalkyl)$, —$O(aryl)$, —$N(C_{0-6}alkyl)(C_{0-6}alkyl)$, —$N(C_{0-6}alkyl)(C_{3-7}cycloalkyl)$, or —$N(C_{0-6}alkyl)(aryl)$ groups;

$R^5$, $R^6$, and $R^7$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —$O(C_{0-6}alkyl)$, —$O(C_{3-7}cycloalkyl)$, —$O(aryl)$, —$N(C_{0-6}alkyl)(C_{0-6}alkyl)$, —$N(C_{0-6}alkyl)(C_{3-7}cycloalkyl)$, —$N(C_{0-6}alkyl)(aryl)$ substituents;

$R^8$ is —$C_{1-6}$alkyl, —$C_{3-7}$cycloalkyl, heteroaryl, or aryl; optionally substituted with 1-5 independent halogen, —CN, —$C_{1-6}$alkyl, —$O(C_{1-6}alkyl)$, —$O(C_{3-7}cycloalkyl)$, —$O(aryl)$, —$N(C_{0-6}alkyl)(C_{0-6}alkyl)$, —$N(C_{0-6}alkyl)(C_{3-7}cycloalkyl)$, —$N(C_{0-6}alkyl)(aryl)$ substituents;

B is —$C_{0-4}$alkyl, —$C_{0-2}$alkyl-SO—$C_{0-2}$alkyl-, —$C_{0-2}$alkyl-$S_{0-2}$—$C_{0-2}$alkyl-, —$C_{0-2}$alkyl-CO—$C_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl, or aryl; any of which is optionally substituted with 1-5 independent halogen, —CN, $C_{1-6}$alkyl, —$O(C_{0-6}alkyl)$, —$O(C_{3-7}cycloalkyl)$, —$O(aryl)$, —$N(C_{0-6}alkyl)(C_{0-6}alkyl)$, —$N(C_{0-6}alkyl)(C_{3-7}cycloalkyl)$, —$N(C_{0-6}alkyl)(aryl)$ substituents;

Z is —$C_{3-7}$cycloalkyl, -hetero$C_{3-7}$cycloalkyl, —$C_{0-6}$alkylaryl, or —$C_{0-6}$alkylheteroaryl optionally substituted with 1-7 independent halogen, —CN, $N_{0-2}$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$C_{0-2}R^1$, —$CONR^1R^2$, —$C(=NR^1)R^2$, or —$C(=NOR^1)R^2$ substituents;

one of W and Z is optionally absent; and any N may be an N-oxide.

In a third aspect, the compounds of this invention are represented by Formula (I) or a pharmaceutically acceptable salt thereof, wherein X is phenyl optionally substituted with 1-5 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}alkyl)$, —$O(C_{3-7}cycloalkyl)$, —$O(aryl)$, —$N(C_{0-6}alkyl)(C_{0-6}alkyl)$, —$N(C_{0-6}alkyl)(C_{3-7}cycloalkyl)$, or —$N(C_{0-6}alkyl)(aryl)$ groups;

$R^1$, $R^2$, and $R^3$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —$O(C_{0-6}alkyl)$, —$O(C_{3-7}cycloalkyl)$, —$O(aryl)$, —$N(C_{0-6}alkyl)(C_{0-6}alkyl)$, —$N(C_{0-6}alkyl)(C_{3-7}cycloalkyl)$, —$N(C_{0-6}alkyl)(aryl)$ substituents;

$R^4$ is —$C_{1-6}$alkyl, —$C_{3-7}$cycloalkyl, heteroaryl, or aryl; optionally substituted with 1-5 independent halogen, —CN, —$C_{1-6}$alkyl, —$O(C_{0-6}alkyl)$, —$O(C_{3-7}cycloalkyl)$, —$O(aryl)$, —$N(C_{0-6}alkyl)(C_{0-6}alkyl)$, —$N(C_{0-6}alkyl)(C_{3-7}cycloalkyl)$, —$N(C_{0-6}alkyl)(aryl)$ substituents;

A is —$C_{0-4}$alkyl, —$C_{0-2}$alkyl-SO—$C_{0-2}$alkyl-, —$C_{0-2}$alkyl-$S_{0-2}$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

W is —$C_{3-7}$cycloalkyl, -hetero$C_{3-7}$cycloalkyl, —$C_{0-6}$alkylaryl, or —$C_{0-6}$alkylheteroaryl optionally substituted with 1-7 independent halogen, —CN, $N_{0-2}$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR1R^2$, —$COR^1$, —$CO_2R^1$, —$CONR^1R^2$, —$C(=NR^1)R^2$, or —$C(=NOR^1)R^2$ substituents;

Y is aryl or heteroaryl optionally substituted with 1-7 independent halogen, —CN, $N_{0-2}$, —$C_{1-6}$alkyl, —$C_{1-6}$alkenyl, —$C_{1-6}$alkynyl, —$OR^5$, —$NR^5R^6$, —$C(=NR^5)NR^6R^7$, —$N(=NR^5)NR^6R^7$, —$NR^5COR^6$, —$NR^5CO_2R^6$, —$NR^5R^6$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —$C(=NR^5)R^6$, or —$C(=NOR^5)R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —$O$(aryl), —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups;

$R^5$, $R^6$, and $R^7$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —$O(C_{0-6}$alkyl), —$O(C_{3-7}$cycloalkyl), —$O$(aryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

$R^8$ is —$C_{1-6}$alkyl, —$C_{3-7}$cycloalkyl, heteroaryl, or aryl; optionally substituted with 1-5 independent halogen, —CN, —$C_{1-6}$alkyl, —$O(C_{0-6}$alkyl), —$O(C_{3-7}$cycloalkyl), —$O$(aryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —$O(C_{0-6}$alkyl), —$O(C_{3-7}$cycloalkyl), —$O$(aryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

Z is —$C_{3-7}$cycloalkyl, -hetero$C_{3-7}$cycloalkyl, —$C_{0-6}$alkylaryl, or —$C_{0-6}$alkylheteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents;

one of W and Z is optionally absent; and any N may be an N-oxide.

In an embodiment of this third aspect, the compounds of this invention are represented by Formula (I) or a pharmaceutically acceptable salt thereof, wherein X is phenyl optionally substituted with 1-5 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —$O$(aryl), —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups;

$R^1$, $R^2$, and $R^3$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —$O(C_{0-6}$alkyl), —$O(C_{3-7}$cycloalkyl), —$O$(aryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

$R^4$ is —$C_{1-6}$alkyl, —$C_{3-7}$cycloalkyl, heteroaryl, or aryl; optionally substituted with 1-5 independent halogen, —CN, —$C_{1-6}$alkyl, —$O(C_{1-6}$alkyl), —$O(C_{3-7}$cycloalkyl), —$O$(aryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

A is —$C_{0-4}$alkyl, —$C_{0-2}$alkyl-SO—$C_{0-2}$alkyl-, —$C_{0-2}$alkyl-$S_{0-2}$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9S^{0-2}$—$C_{0-2}$alkyl- or -hetero$C^{0-4}$alkyl;

W is —$C_{3-7}$cycloalkyl, -hetero$C_{3-7}$cycloalkyl, —$C_{0-6}$alkylaryl, or —$C_{0-6}$alkylheteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents;

Y is 2-pyridyl optionally substituted with 1-4 independent halogen, —CN, $NO_2$, —$C_{1-6}$alkyl, —$C_{1-6}$alkenyl, —$C_{1-6}$alkynyl, —$OR^5$, —$NR^5R^6$, —$C(=NR^5)NR^6R^7$, —$N(=NR^5)NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO^2NR^5R^6$, —$COR^5$, —$CO_2R^5$, —$CONR^5R^6$, —$C(=NR^5)R^6$, or —$C(=NOR^5)R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —$O$(aryl), —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups;

$R^5$, $R^6$, and $R^7$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —$O(C_{0-6}$alkyl), —$O(C_{3-7}$cycloalkyl), —$O$(aryl), —$N(C_{0-6}$alkyl)($C_{0-6}$alkyl), —$N(C_{1-6}$alkyl)($C_{3-7}$cycloalkyl), —$N(C_{0-6}$alkyl)(aryl) substituents;

$R^8$ is —$C_{1-6}$alkyl, —$C_{3-7}$cycloalkyl, heteroaryl, or aryl; optionally substituted with 1-5 independent halogen, —CN, —$C_{1-6}$alkyl, —$O(C_{0-6}$alkyl), —$O(C_{3-7}$cycloalkyl), —$O$(aryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —($C_{0-6}$alkyl), —$O(C_{3-7}$cycloalkyl), —$O$(aryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

Z is —$C_{3-7}$cycloalkyl, —hetero$C_{3-7}$cycloalkyl, —$C_{0-6}$alkylaryl, or —$C_{0-6}$alkylheteroaryl optionally substituted with 1-7 independent halogen, —CN, $NO_2$, —$C_{1-6}$alkyl, —$C_{1-6}$alkenyl, —$C_{1-6}$alknynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents;

one of W and Z is optionally absent; and any N may be an N-oxide.

In a fourth aspect, the compounds of this invention are represented by Formula (I) or a pharmaceutically acceptable salt thereof, wherein X is aryl or heteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —O(aryl), —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups;

$R^1$, $R^2$, and $R^3$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —$O(C_{0-6}$alkyl), —$O(C_{3-7}$cycloalkyl), —O(aryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

$R^4$ is —$C_{1-6}$alkyl, —$C_{3-7}$cycloalkyl, heteroaryl, or aryl; optionally substituted with 1-5 independent halogen, —CN, —$C_{1-6}$alkyl, —$O(C_{0-6}$alkyl), —$O(C_{3-7}$cycloalkyl), —O(aryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

W is —$C_{3-7}$cycloalkyl, -hetero$C_{3-7}$cycloalkyl, —$C_{0-6}$alkylaryl, or —$C_{0-6}$alkylheteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents;

Y is 1,3-thiazolyl optionally substituted with 1-2 independent halogen, —CN, $NO_2$, —$C_{1-6}$alkyl, —$C_{1-6}$alkenyl, —$C_{1-6}$alkynyl, —$OR^5$, —$NR^5R^6$, —$C(=NR^5)NR^6R^7$, —$N(=NR^5)NR^6R^7$, —$NR^5COR^6$, —$NR^5CO_2R^6$, —$NR^5R^6$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —$C(=NR^5)R^6$, or —$C(=NOR^5)R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), ($C_{3-7}$cycloalkyl), —O(aryl), —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups;

$R^5$, $R^6$, and $R^7$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —$O(C_{0-6}$alkyl), —$O(C_{3-7}$cycloalkyl), —O(aryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

$R^8$ is —$C_{1-6}$alkyl, —$C_{3-7}$cycloalkyl, heteroaryl, or aryl; optionally substituted with 1-5 independent halogen, —CN, —$C_{1-6}$alkyl, —$O(C_{0-6}$alkyl), —$O(C_{3-7}$cycloalkyl), —O(aryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —$O(C_{0-6}$alkyl), —$O(C_{3-7}$cycloalkyl), —O(aryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

Z is —$C_{3-7}$cycloalkyl, -hetero$C_{3-7}$cycloalkyl, —$C_{0-6}$alkylaryl, or —$C_{0-6}$alkylheteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents;

one of W and Z is optionally absent; and any N may be an N-oxide.

In an embodiment of this fourth aspect, the compounds of this invention are represented by Formula (I) or a pharmaceutically acceptable salt thereof, wherein X is phenyl optionally substituted with 1-5 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R_4$, —$SO_2NR^1R^2$, —$COR^1$, —$CO_2R^1$, —$CONR^1R^2$, —$C(=NR^1)R^2$, or —$C(=NOR^1)R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —O(aryl), —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups;

$R^1$, $R^2$, and $R^3$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, ($C_{0-6}$alkyl), —$O(C_{3-7}$cycloalkyl), —O(aryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

$R^4$ is —$C_{1-6}$alkyl, —$C_{3-7}$cycloalkyl, heteroaryl, or aryl; optionally substituted with 1-5 independent halogen, —CN, —$C_{1-6}$alkyl, —$O(C_{0-6}$alkyl), —$O(C_{3-7}$cycloalkyl), —O(aryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

A is —$C_{0-4}$alkyl, —$C_{0-2}$alkyl-SO—$C_{0-2}$alkyl-, —$C_{0-2}$alkyl-$S_{0-2}$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9S_{0-2}$—$C_{0-2}$alkyl- or -hetero$C_{0-4}$alkyl;

W is —$C_{3-7}$cycloalkyl, -hetero$C_{3-7}$cycloalkyl, —$C_{0-6}$alkylaryl, or —$C_{0-6}$alkylheteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C)=$NR^1)R^2$, —$C(=NR^1)R^2$, or —$C(=NOR^1)R^2$ substituents;

Y is 1,3-thiazolyl optionally substituted with 1-2 independent halogen, —CN, $NO_2$, —$C_{1-6}$alkyl, —$C_{1-6}$alkenyl, —$C_{1-6}$alkynyl, —$OR^5$, —$NR^5R^6$, —$C(=NR^5)NR^6R^7$, —$N(=NR^5)NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CORN^5R^6$, —C(=NR$^5$)R$^6$, or —C(=NOR$^5$)R$^6$ substituents, wherein optionally two substituents are combined to form a cycloalkyl or heterocycloalkyl ring fused to Y; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups;

R$^5$, R$^6$, and R$^7$ each independently is —C$_{0-6}$alkyl, —C$_{3-7}$cycloalkyl, heteroaryl, or aryl; any of which is optionally substituted with 1-5 independent halogen, —CN, —C$_{1-6}$alkyl, —O(C$_{0-6}$alkyl), —O(C$_{3-7}$cycloalkyl), (aryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

R$^8$ is —C$_{1-6}$alkyl, —C$_{3-7}$cycloalkyl, heteroaryl, or aryl; optionally substituted with 1-5 independent halogen, —CN, —C$_{1-6}$alkyl, —O(C$_{1-6}$alkyl), —O(C$_{3-7}$cycloalkyl), —O(aryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

B is —C$_{0-4}$alkyl, —C$_{0-2}$alkyl-SO—C$_{0-2}$alkyl-, —C$_{0-2}$alkyl-SO$_2$—C$_{0-2}$alkyl-, —C$_{0-2}$alkyl-CO—C$_{0-2}$alkyl-, —C$_{0-2}$alkyl-NR$^{10}$CO—C$_{0-2}$alkyl-, —C$_{0-2}$alkyl-NR$^{10}$SO$_2$—C$_{0-2}$alkyl- or -heteroC$_{0-4}$alkyl;

R$^9$ and R$^{10}$ each independently is —C$_{0-6}$alkyl, —C$_{3-7}$cycloalkyl, heteroaryl, or aryl; any of which is optionally substituted with 1-5 independent halogen, —CN, —C$_{1-6}$alkyl, —O(C$_{0-6}$alkyl), —O(C$_{3-7}$cycloalkyl), —O(aryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

Z is —C$_{3-7}$cycloalkyl, -heteroC$_{3-7}$cycloalkyl, —C$_{0-6}$alkylaryl, or —C$_{0-6}$alkylheteroaryl optionally substituted with 1-7 independent halogen, —CN, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents;

one of W and Z is optionally absent; and any N may be an N-oxide.

In a fifth aspect, the compounds of this invention are represented by Formula (I) or a pharmaceutically acceptable salt thereof, wherein X is aryl or heteroaryl optionally substituted with 1-7 independent halogen, —CN, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to X; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups;

R$^1$, R$^2$, and R$^3$ each independently is —C$_{0-6}$alkyl, —C$_{3-7}$cycloalkyl, heteroaryl, or aryl; any of which is optionally substituted with 1-5 independent halogen, —CN, —C$_{1-6}$alkyl, —O(C$_{0-6}$alkyl), —O(C$_{3-7}$cycloalkyl), —O(aryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

R$^4$ is —C$_{1-6}$alkyl, —C$_{3-7}$cycloalkyl, heteroaryl, or aryl; optionally substituted with 1-5 independent halogen, —CN, —C$_{1-6}$alkyl, —O(C$_{1-6}$alkyl), —O(C$_{3-7}$cycloalkyl), —O(aryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

A is —C$_{0-4}$alkyl, —C$_{0-2}$alkyl-SO—C$_{0-2}$alkyl-, —C$_{0-2}$alkyl-SO$_2$—C$_{0-2}$alkyl-, —C$_{0-2}$alkyl-CO—C$_{0-2}$alkyl-, —C$_{0-2}$alkyl-NR$^9$CO—C$_{0-2}$alkyl-, —C$_{0-2}$alkyl-NR$^9$SO$_2$—C$_{0-2}$alkyl- or -heteroC$_{0-4}$alkyl;

W is —C$_{0-6}$alkylaryl or —C$_{0-6}$alkylheteroaryl optionally substituted with 1-7 independent halogen, —CN, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents;

Y is aryl or heteroaryl optionally substituted with 1-7 independent halogen, —CN, NO$_2$, —C$_{1-6}$alkyl, —C$_{1-6}$alkenyl, —C$_{1-6}$alkynyl, —OR$^5$, —NR$^5$R$^6$, —C(=NR$^5$)NR$^6$R$^7$, —N(=NR$^5$)NR$^6$R$^7$, —NR$^5$COR$^6$, —NR$^5$CO$_2$R$^6$, —NR$^5$SO$_2$R$^8$, —NR$^5$CONR$^6$R$^7$, —SR$^8$, —SOR$^8$, —SO$_2$R$^8$, —SO$_2$NR$^5$R$^6$, —COR$^5$, —CO$_2$R$^5$, —CONR$^5$R$^6$, —C(=NR$^5$)R$^6$, or —C(=NOR$^5$)R$^6$ substituents, wherein optionally two substituents are combined to form a cycloalkyl or heterocycloalkyl ring fused to Y; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups;

R$^5$, R$^6$, and R$^7$ each independently is —C$_{0-6}$alkyl, —C$_{3-7}$cycloalkyl, heteroaryl, or aryl; any of which is optionally substituted with 1-5 independent halogen, —CN, —C$_{1-6}$alkyl, —O(C$_{0-6}$alkyl), —O(C$_{3-7}$cycloalkyl), —O(aryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

R$^8$ is —C$_{1-6}$alkyl, —C$_{3-7}$cycloalkyl, heteroaryl, or aryl; optionally substituted with 1-5 independent halogen, —CN, —C$_{1-6}$alkyl, —O(C$_{1-6}$alkyl), —O(C$_{3-7}$cycloalkyl), —O(aryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

B is —C$_{0-4}$alkyl, —C$_{0-2}$alkyl-SO—C$_{0-2}$alkyl-, —C$_{0-2}$alkyl-SO$_2$—C$_{0-2}$alkyl-, —C$_{0-2}$alkyl-CO—C$_{0-2}$alkyl-, —C$_{0-2}$alkyl-NR$^{10}$CO—C$_{0-2}$alkyl-, —C$_{0-2}$alkyl-NR$^{10}$SO$_2$—C$_{0-2}$alkyl- or -heteroC$_{0-4}$alkyl;

R$^9$ and R$^{10}$ each independently is —C$_{0-6}$alkyl, —C$_{3-7}$cycloalkyl, heteroaryl, or aryl; any of which is optionally substituted with 1-5 independent halogen, —CN, C$_{1-6}$alkyl, —O(C$_{0-6}$alkyl), —O(C$_{3-7}$cycloalkyl), —O(aryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

Z is —C$_{3-7}$cycloalkyl, -heteroC$_{3-7}$cycloalkyl, —C$_{0-6}$alkylaryl, or —C$_{0-6}$alkylheteroaryl optionally substituted with 1-7 independent halogen, —CN, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents;

one of W and Z is optionally absent; and any N may be an N-oxide.

In a sixth aspect, the compounds of this invention are represented by Formula (I) or a pharmaceutically acceptable salt thereof, wherein X is aryl or heteroaryl optionally substituted with 1-7 independent halogen, —CN, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^1$, $R^2$, and $R^3$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-SO$_2$—$C_{0-2}$alkyl-, —$C_{0-2}$alkyl-CO—$C_{0-2}$alkyl-, —$C_{0-2}$alkyl-NR$^9$CO—$C_{0-2}$alkyl-, —$C_{0-2}$alkyl-NR$^9$SO$_2$—$C_{0-2}$alkyl- or -hetero$C_{0-4}$alkyl;

W is —$C_{0-6}$alkylaryl or —$C_{0-6}$alkylheteroaryl optionally substituted with 1-7 independent halogen, —CN, NO$_2$, —$C_{1-6}$alkyl, —$C_{1-6}$alkenyl, —$C_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents;

Y is pyrazolyl optionally substituted with 1-3 independent halogen, —CN, NO$_2$, —$C_{1-6}$alkyl, —$C_{1-6}$alkenyl, —$C_{1-6}$alkynyl, —OR$^5$, —NR$^5$R$^6$, —C(=NR$^5$)NR$^6$R$^7$, —N(=NR$^5$)NR$^6$R$^7$, —NR$^5$COR$^6$, —NR$^5$CO$_2$R$^6$, —NR$^5$SO$_2$R$^8$, —NR$^5$CONR$^6$R$^7$, —SR$^8$, —SOR$^8$, —SO$_2$R$^8$, —SO$_2$NR$^5$R$^6$, —COR$^5$, —CO$_2$R$^5$, —CONR$^5$R$^6$, —C(=NR$^5$)R$^6$, or —C(=NOR$^5$)R$^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$allyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-SO$_2$—$C_{0-2}$alkyl-, —$C_{0-2}$alkyl-CO—$C_{0-2}$alkyl-, —$C_{0-2}$alkyl-NR$^{10}$CO—$C_{0-2}$alkyl-, —$C_{0-2}$alkyl-NR$^{10}$SO$_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

Z is —$C_{3-7}$cycloalkyl, -hetero$C_{3-7}$cycloalkyl, —$C_{0-6}$alkylaryl, or —$C_{0-6}$alkylheteroaryl optionally substituted with 1-7 independent halogen, —CN, NO$_2$, —$C_{-6}$alkyl, —$C_{1-6}$alkenyl, —$C_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents;

one of W and Z is optionally absent; and any N may be an N-oxide.

In an embodiment of this sixth aspect, the compounds of this invention are represented by Formula (I) or a pharmaceutically acceptable salt thereof, wherein X is phenyl optionally substituted with 1-5 independent halogen, —CN, NO$_2$, —$C_{1-6}$alkyl, —$C_{1-6}$alkenyl, —$C_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^1$, $R^2$, and $R^3$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, $C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —CO$_4$alkyl, —$C_{0-2}$alkyl-SO—$C_{0-2}$alkyl-, —$C_{0-2}$alkyl-SO$_2$—$C_{0-2}$alkyl-, —$C_{0-2}$alkyl-CO—$C_{0-2}$alkyl-, —$C_{0-2}$alkyl-NR$^9$CO—$C_{0-2}$alkyl-, —$C_{0-2}$alkyl-NR$^9$SO$_2$—$C_{0-2}$alkyl- or -hetero$C_{0-4}$alkyl;

W is —$C_{0-6}$alkylaryl or —$C_{0-6}$alkylheteroaryl optionally substituted with 1-7 independent halogen, —CN, NO$_2$, —$C_{1-6}$alkyl, —$C_{1-6}$alkenyl, —$C_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or C(=NOR$^1$)R$^2$ substituents;

Y is pyrazolyl optionally substituted with 1-3 independent halogen, —CN, NO$_2$, —$C_{1-6}$alkyl, —$C_{1-6}$alkenyl, —$C_{1-6}$alkynyl, —OR$^5$, —NR$^5$R$^6$, —C(=NR$^5$)NR$^6$R$^7$, —N(=NR$^5$)NR$^6$R$^7$, —NR$^5$COR$^6$, —NR$^5$CO$_2$R$^6$, —NR$^5$SO$_2$R$^8$, —NR$^5$CONR$^6$R$^7$, SR$^8$, —SOR$^8$, —SO$_2$R$^8$, —SO$_2$NR$^5$R$^6$, —COR$^5$, CO$_2$R$^5$, —CONR$^5$R$^6$, —C(=NR$^5$)R$^6$, or —C(=NOR$^5$)R$^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), (aryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{1-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl—$SO_2$—$C_{0-2}$alkyl-, —$C_{0-2}$alkyl-CO—$C_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

Z is —$C_{3-7}$cycloalkyl, -hetero$C_{3-7}$cycloalkyl, —$C_{0-6}$alkylaryl, or —$C_{0-6}$alkylheteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1C_{0-2}R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents;

one of W and Z is optionally absent; and any N may be an N-oxide.

In a seventh aspect, the compounds of this invention are represented by Formula (I) or a pharmaceutically acceptable salt thereof, wherein X is aryl or heteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^1$, $R^2$, and $R^3$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

W is —$C_{0-6}$alkylaryl or —$C_{0-6}$alkylheteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents;

Y is imidazolyl optionally substituted with 1-3 independent halogen, —CN, $NO_2$, —$C_{1-6}$alkyl, —$C_{1-6}$alkenyl, —$C_{1-6}$ alkynyl, —$OR^5$, —$NR^5R^6$, —C(=$NR^5$)$NR^6R^7$, —N(=$NR^5$)$NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —C(=$NR^5$)$R^6$, or —C(=$NOR^5$)$R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

Z is —$C_{3-7}$cycloalkyl, -hetero$C_{3-7}$cycloalkyl, —$C_{0-6}$alkylaryl, or —$C_{0-6}$alkylheteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, $CONR^1R^2$, —C(=$NR^1$)$R^2$, or —C(=$NOR^1$)$R^2$ substituents;

one of W and Z is optionally absent; and any N may be an N-oxide.

In an embodiment of this seventh aspect, the compounds of this invention are represented by Formula (I) or a pharmaceutically acceptable salt thereof, wherein X is phenyl optionally substituted with 1-5 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^1$, $R^2$, and $R^3$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_3$-7cycloalkyl), —N($C_{0-6}$alkyl)(aryl) substituents;

$R^4$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

W is —$C_{3-7}$cycloalkyl, -hetero$C_{3-7}$cycloalkyl, —$C_{0-6}$alkylaryl, or —$C_{0-6}$alkylheteroaryl optionally substituted with 1-7 independent halogen, —CN, $NO_2$, —$C_{1-6}$alkyl, —$C_{1-6}$alkenyl, —$C_{1-6}$alkynyl, —OR, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, $O_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents;

Y is imidazolyl optionally substituted with 1-3 independent halogen, —CN, $NO_2$, —$C_{1-6}$alkyl, —$C_{1-6}$alkenyl, —$C_{1-6}$alkynyl, —$OR^5$, —$NR^5R^6$, —C(=$NR^5$)$NR^6R^7$, —N(=$NR^5$)$NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —C(=$NR^5$)$R^6$, or —C(=$NOR^5$)$R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

Z is —$C_{3-7}$cycloalkyl, -hetero$C_{3-7}$cycloalkyl, —$C_{0-6}$alkylaryl, or —$C_{0-6}$alkylheteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents;

one of W and Z is optionally absent; and
any N may be an N-oxide.

In an eighth aspect, the compounds of this invention are represented by Formula (I) or a pharmaceutically acceptable salt thereof, wherein X is 3-pyridyl optionally substituted with 1-4 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^1$, $R^2$, and $R^3$ each independently is —$C_{0-6}$alkyl, —$C_{3-7}$cycloalkyl, heteroaryl, or aryl; any of which is optionally substituted with 1-5 independent halogen, —CN, $C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

W is —$C_{3-7}$cycloalkyl, -hetero$C_{3-7}$cycloalkyl, —$C_{0-6}$alkylaryl, or —$C_{0-6}$alkylheteroaryl optionally substituted with 1-7 independent halogen, —CN, $NO_2$, —$C_{0-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents;

Y is aryl or heteroaryl optionally substituted with 1-7 independent halogen, —CN, $NO_2$, —$C_{1-6}$alkyl, —$C_{1-6}$alkenyl, —$C_{1-6}$alkynyl, —$OR^5$, —$NR^5R^6$, —C(=$NR^5$)$NR^6R^7$, —N(=$NR^5$)$NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —C(=$NR^5$)$R^6$, or —C(=$NOR^5$)$R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$Alkyl-, —$C_{0-2}$alkyl-CO—$C_{0-2}$alkyl-, —$C_{0-2}$alkyl-$NR^{10}CO$—$C_{0-2}$alkyl-, —$C_{0-2}$alkyl-$NR^{10}SO_2$—$C_{0-2}$alkyl- or -heteroC$_{0-4}$alkyl;

$R^9$ and $R^{10}$ each independently is —$C_{0-6}$alkyl, $C_{3-7}$cycloalkyl, heteroaryl, or aryl; any of which is optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

Z is —$C_{3-7}$cycloalkyl, -heteroC$_{3-7}$cycloalkyl, —$C_{0-6}$alkylaryl, or —$C_{0-6}$alkylheteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents;

one of W and Z is optionally absent; and any N may be an N-oxide.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "aryl" means an aromatic substituent which is a single ring or multiple rings fused together. When formed of multiple rings, at least one of the constituent rings is aromatic. The preferred aryl substituents are phenyl and naphthyl groups.

The term "cycloalkyloxy" unless specifically stated otherwise includes a cycloalkyl group connected by a short $C_{1-2}$ alkyl length to the oxy connecting atom.

The term "$C_{0-6}$alkyl" includes alkyls containing 6, 5, 4, 3, 2, 1, or no carbon atoms. An alkyl with no carbon atoms is a hydrogen atom substituent when the alkyl is a terminal group and is a direct bond when the alkyl is a bridging group.

The term "hetero" unless specifically stated otherwise includes one or more O, S, or N atoms. For example, heterocycloalkyl and heteroaryl include ring systems that contain one or more O, S, or N atoms in the ring, including mixtures of such atoms. The hetero atoms replace ring carbon atoms. Thus, for example, a heterocycloC$_5$alkyl is a five-member ring containing from 4 to no carbon atoms. Examples of heteroaryls include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, benzoxazolyl, isoxazolyl, thiazolyl, benzothiazolyl, isothiazolyl, imidazolyl, benzimidazolyl, oxadiazolyl, thiadiazolyl, triazolyl, and tetrazolyl. Examples of heterocycloalkyls include azetidinyl, pyrrolidinyl, piperidinyl, piperazinyl, morpholinyl, tetrahydrofuranyl, imidazolinyl, pyrolidin-2-one, piperidin-2-one, and thiomorpholinyl.

The term "heteroC$_{0-4}$alkyl" means a heteroalkyl containing 3, 2, 1, or no carbon atoms. However, at least one heteroatom must be present. Thus, as an example, a heteroC$_{0-4}$alkyl having no carbon atoms but one N atom would be a —NH— if a bridging group and a —$NH_2$ if a terminal group. Analogous bridging or terminal groups are clear for an O or S heteroatom.

The term "amine" unless specifically stated otherwise includes primary, secondary and tertiary amines substituted with $C_{0-6}$alkyl.

The term "carbonyl" unless specifically stated otherwise includes a $C_{0-6}$alkyl substituent group when the carbonyl is terminal.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, optionally substituted multiple moieties such as, for example, alkylaryl are intended to mean that the aryl and the aryl groups are optionally substituted. If only one of the multiple moieties is optionally substituted then it will be specifically recited such as "an alkylaryl, the aryl optionally substituted with halogen or hydroxyl."

Compounds described herein contain one or more double bonds and may thus give rise to cis/trans isomers as well as other conformational isomers. The present invention includes all such possible isomers as well as mixtures of such isomers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. Such additional therapeutic ingredients include, for example, i) opiate agonists or antagonists, ii) calcium channel antagonists, iii) 5HT receptor agonists or antagonists iv) sodium channel antagonists, v) NMDA receptor agonists or antagonists, vi) COX-2 selective inhibitors, vii) NK1 antagonists, viii) non-steroidal anti-inflammatory drugs ("NSAID"), ix) GABA-A receptor modulators, x) dopamine agonists or antagonists, xi) selective serotonin reuptake inhibitors ("SSRI") and/or selective serotonin and norepinephrine reuptake inhibitors ("SSNRI"), xii) tricyclic antidepressant drugs, xiv) norepinephrine modulators, xv) L-DOPA, xvi) buspirone, xvii) lithium, xviii) valproate, ixx) neurontin (gabapentin), xx) olanzapine, xxi) nicotinic agonists or antagonists including nicotine, xxii) muscarinic agonists or antagonists, xxiii) heroin substituting drugs such as methadone, levo-alpha-acetylmethadol, buprenorphine and naltrexone, and xxiv) disulfiram and acamprosate. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Creams, ointments, jellies, solutions, or suspensions containing the compound of Formula I can be employed for topical use. Mouth washes and gargles are included within the scope of topical use for the purposes of this invention.

Dosage levels from about 0.01 mg/kg to about 140 mg/kg of body weight per day are useful in the treatment of psychiatric and mood disorders such as, for example, schizophrenia, anxiety, depression, panic, bipolar disorders, and circadian disorders, as well as being useful in the treatment of pain which are responsive to mGluR5 inhibition, or alternatively about 0.5 mg to about 7 g per patient per day. For example, schizophrenia, anxiety, depression, and panic may be effectively treated by the administration of from about 0.01 mg to 75 mg of the compound per kilogram of body weight per day, or alternatively about 0.5 mg to about 3.5 g per patient per day. Pain may be effectively treated by the administration of from about 0.01 mg to 125 mg of the compound per kilogram of body weight per day, or alternatively about 0.5 mg to about 5.5 g per patient per day. Further, it is understood that the mGluR5 inhibiting compounds of this invention can be administered at prophylactically effective dosage levels to prevent the above-recited conditions.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 1 mg to about 1000 mg of the active ingredient, typically 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient. Thus, a tablet, cachet, or capsule conveniently contains 0.1 mg, 1mg, 5 mg, 25 mg, 50 mg, 100 mg, 200 mg, 300 mg, 400 mg, or 500 mg of the active ingredient taken one or two tablets, cachets, or capsules, once, twice, or three times daily.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The compounds and pharmaceutical compositions of this invention have been found to exhibit biological activity as mGluR5 inhibitors. Accordingly, another aspect of the invention is the treatment in mammals of, for example, schizophrenia, anxiety, depression, panic, bipolar disorders, circadian rhythm and sleep disorders, pain, Parkinson's disease, cognitive dysfunction, epilepsy, obesity, drug addiction, drug abuse and drug withdrawal—maladies that are amenable to amelioration through inhibition of mGluR5—by the administration of an effective amount of the compounds of this invention. The term "mammals" includes humans, as well as other animals such as, for example, dogs, cats, horses, pigs, and cattle. Accordingly, it is understood that the treatment of mammals other than humans is the treatment of clinical correlating afflictions to those above recited examples that are human afflictions.

Further, as described above, the compound of this invention can be utilized in combination with other therapeutic compounds. In particular, the combinations of the mGluR5 inhibiting compound of this invention can be advantageously used in combination with i) opiate agonists or antagonists, ii) calcium channel antagonists, iii) 5HT receptor agonists or antagonists iv) sodium channel antagonists, v) NMDA receptor agonists or antagonists, vi) COX-2 selective inhibitors, vii) NK1 antagonists, viii) non-steroidal anti-inflammatory drugs ("NSAID"), ix) GABA-A receptor modulators, x) dopamine agonists or antagonists, xi) selective serotonin reuptake inhibitors ("SSRI") and/or selective serotonin and norepinephrine reuptake inhibitors ("SSNRI"), xii) tricyclic antidepressant drugs, xiii) norepinephrine modulators, xiv) L-DOPA, xv) buspirone, xvi) lithium, xvii) valproate, xviii) neurontin (gabapentin), xix) olanzapine, xx) nicotinic agonists or antagonists including nicotine, xxi) muscarinic agonists or antagonists, xxii) heroin substituting drugs such as methadone, levo-alpha-acetylmethadol, buprenorphine and naltrexone, and xxiii) disulfiram and acamprosate.

The abbreviations used herein have the following tabulated meanings. Abbreviations not tabulated below have their meanings as commonly used unless specifically stated otherwise.

| | |
|---|---|
| Ac | acetyl |
| AIBN | 2,2'-azobis(isobutyronitrile) |
| BINAP | 1,1'-bi-2-naphthol |
| Bn | benzyl |
| CAMP | cyclic adenosine-3',5'-monophosphate |
| DAST | (diethylamino)sulfur trifluoride |
| DEAD | diethyl azodicarboxylate |
| DBU | 1,8-diazabicyclo[5.4.0]undec-7-ene |
| DIBAL | diisobutylaluminum hydride |
| DMAP | 4-(dimethylamino)pyridine |
| DMF | N,N-dimethylformamide |
| Dppf | 1,1'-bis(diphenylphosphino)-ferrocene |
| EDCI | 1-(3-dimethylaminopropyl)-3-ethylcarbodiimide hydrochloride |
| Et$_3$N | triethylamine |
| GST | glutathione transferase |
| HMDS | hexamethyldisilazide |
| LDA | lithium diisopropylamide |
| m-CPBA | metachloroperbenzoic acid |

-continued

| | |
|---|---|
| MMPP | monoperoxyphthalic acid |
| MPPM | monoperoxyphthalic acid, magnesium salt 6H$_2$O |
| Ms | methanesulfonyl = mesyl = SO$_2$Me |
| MsO | methanesulfonate = mesylate |
| NBS | N-bromo succinimide |
| NSAID | non-steroidal anti-inflammatory drug |
| o-Tol | ortho-tolyl |
| OXONE ® | 2KHSO$_5$•KHSO$_4$•K$_2$SO$_4$ |
| PCC | pyridinium chlorochromate |
| Pd$_2$(dba)$_3$ | Bis(dibenzylideneacetone) palladium(0) |
| PDC | pyridinium dichromate |
| PDE | Phosphodiesterase |
| Ph | Phenyl |
| Phe | Benzenediyl |
| PMB | para-methoxybenzyl |
| Pye | Pyridinediyl |
| r.t. | room temperature |
| Rac. | Racemic |
| SAM | aminosulfonyl or sulfonamide or SO$_2$NH$_2$ |
| SEM | 2-(trimethylsilyl)ethoxymethoxy |
| SPA | scintillation proximity assay |
| TBAF | tetra-n-butylammonium fluoride |
| Th | 2- or 3-thienyl |
| TFA | trifluoroacetic acid |
| TFAA | trifluoroacetic acid anhydride |
| THF | Tetrahydrofuran |
| Thi | Thiophenediyl |
| TLC | thin layer chromatography |
| TMS-CN | trimethylsilyl cyanide |
| TMSI | trimethylsilyl iodide |
| Tz | 1H (or 2H)-tetrazol-5-yl |
| XANTPHOS | 4,5-Bis-diphenylphosphanyl-9,9-dimethyl-9H-xanthene |
| C$_3$H$_5$ | Allyl |

ALKYL GROUP ABBREVIATIONS

| | |
|---|---|
| Me = | Methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | cyclobutyl |
| c-Pen = | cyclopentyl |
| c-Hex = | cyclohexyl |

Assays Demonstrating Biological Activity

The compounds of this invention were tested against the hmGluR5a receptor stably expressed in mouse fibroblast Ltk$^-$ cells (the hmGluR5a/L38-20 cell line) and activity was detected by changes in [Ca$^{++}$]$_i$, measured using the fluorescent Ca$^{++}$-sensitive dye, fura-2. InsP assays were performed in mouse fibroblast Ltk$^-$ cells (LM5a cell line) stably expressing hmGluR5a. The assays described in International Patent Publication WO 0116121 can be used.

Calcium Flux Assay

The activity of compounds was examined against the hmGluR5a receptor stably expressed in mouse fibroblast Ltk- cells (the hmGluR5a/L38 cell line). See generally Daggett et al., *Neuropharmacology* 34:871-886 (1995). Receptor activity was detected by changes in intracellular calcium ([Ca$^{2+}$]$_i$) measured using the fluorescent calcium-sensitive dye, fura-2. The hmGluR5a/L38-20 cells were plated onto 96-well plates, and loaded with 3 µM fura-2 for 1h. Unincorporated dye was washed from the cells, and the cell plate was transferred to a 96-channel fluorimeter (SIBIA-SAIC, La Jolla, Calif.) which is integrated into a fully automated plate handling and liquid delivery system. Cells were excited at 350 and 385 nm with a xenon source combined with optical filters. Emitted light was collected from the sample through a dichroic mirror and a 510 nm interference filter and directed into a cooled CCD camera (Princeton Instruments). Image pairs were captured approximately every 1 s, and ratio images were generated after background subtraction. After a basal reading of 20 s, an EC$_{80}$ concentration of glutamate (10 µM) was added to the well, and the response evaluated for another 60 s. The glutamate-evoked increase in [Ca']$_i$ in the presence of the screening compound was compared to the response of glutamate alone (the positive control).

Phosphatidylinositol Hydrolysis (PI) Assays

Inositolphosphate assays were performed as described by Berridge et al. [Berridge et al, *Biochem. J.* 206: 587-5950 (1982); and Nakajima et al., *J. Biol. Chem.* 267:2437-2442 (1992)] with slight modifications. Mouse fibroblast Ltk cells expressing hmGluR5 (hmGluR5/L38-20 cells) were seeded in 24-well plates at a density of 8×105 cells/well. One µCi of [$^3$H]-inositol (Amersham PT6-271; Arlington Heights, Ill.; specific activity=17.7 Ci/mmol) was added to each well and incubated for 16 h at 37° C. Cells were washed twice and incubated for 45 min in 0.5 mL of standard Hepes buffered saline buffer (HBS; 125 mM NaCl, 5 mM KCl, 0.62 mM MgSO$_4$, 1.8 mM CaCl$_2$, 20 mM HEPES, 6 mM glucose, pH to 7.4). The cells were washed with HBS containing 10 mM LiCl, and 400 µL buffer added to each well. Cells were incubated at 37° C. for 20 min. For testing, 50 µL of 10× compounds used in the practice of the invention (made in HBS/LiCl (100 mM)) was added and incubated for 10 minutes. Cells were activated by the addition of 10 µM glutamate, and the plates left for 1 hour at 37° C. The incubations were terminated by the addition of 1 mL ice-cold methanol to each well. In order to isolate inositol phosphates (IPs), the cells were scraped from wells, and placed in numbered glass test tubes. One mL of chloroform was added to each tube, the tubes were mixed, and the phases separated by centrifugation. IPs were separated on Dowex anion exchange columns (AG 1-X8 100-200 mesh formate form). The upper aqueous layer (750 µL) was added to the Dowex columns, and the columns eluted with 3 mL of distilled water. The eluents were discarded, and the columns were washed with 10 mLs of 60 mM ammonium formate/5 mM Borax, which was also discarded as waste. Finally, the columns were eluted with 4 mL of 800 mM ammonium formate/0.1 M formic acid, and the samples collected in scintillation vials. Scintillant was added to each vial, and the vials shaken, and counted in a scintillation counter after 2 hours. Phosphatidylinositol hydrolysis in cells treated with certain exemplary compounds was compared to phosphatidylinositol hydrolysis in cells treated with the agonist alone in the absence of compound.

The compounds of this application have mGluR5 inhibitory activity as shown by IC$_{50}$ values of less than 10 µM in the calcium flux assay or inhibition at a concentration of 100 µM in the PI assay. Preferably, the compounds should have IC$_{50}$ values of less than 1 µM in the calcium flux assay and IC$_{50}$ values of less than 10 µM in the PI assay. Even more preferably, the compounds should have IC$_{50}$ values of less than 500 nM in the calcium flux assay and IC$_{50}$ values of less than 1 µM in the PI assay Examples 1 to 347 have mGluR5 inhibitory activity as shown by inhibition at 10 µM or less in the calcium flux assay or inhibition at 100 µM or less in the PI assay.

The examples that follow are intended as an illustration of certain preferred embodiments of the invention and no limitation of the invention is implied.

Unless specifically stated otherwise, the experimental procedures were performed under the following conditions. All operations were carried out at room or ambient temperature—that is, at a temperature in the range of 18-25° C. Evaporation of solvent was carried out using a rotary evaporator under reduced pressure (600-4000 pascals: 4.5-30 mm. Hg) with a bath temperature of up to 60° C. The course of reactions was followed by thin layer chromatography (TLC) and reaction times are given for illustration only. Melting points are uncorrected and 'd' indicates decomposition. The melting points given are those obtained for the materials prepared as described. Polymorphism may result in isolation of materials with different melting points in some preparations. The structure and purity of all final products were assured by at least one of the following techniques: TLC, mass spectrometry, nuclear magnetic resonance (NMR) spectrometry or microanalytical data. When given, yields are for illustration only. When given, NMR data is in the form of delta (δ) values for major diagnostic protons, given in parts per million (ppm) relative to tetramethylsilane (TMS) as internal standard, determined at 300 MHz, 400 MHz or 500 MH using the indicated solvent. Conventional abbreviations used for signal shape are: s. singlet; d. doublet; t. triplet; m. multiplet; br. broad; etc. In addition, "Ar" signifies an aromatic signal. Chemical symbols have their usual meanings; the following abbreviations are used: v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

Methods of Synthesis

Compounds of the present invention can be prepared according to the following methods. The substituents are the same as in Formula I except where defined otherwise.

In accordance with another embodiment of the present invention, there are provided methods for the preparation of heteroaryl-substituted tetrazole compounds as described above. For example, many of the heterocyclic compounds described above can be prepared using synthetic chemistry techniques well known in the art (see *Comprehensive Heterocyclic Chemistry*, Katritzky, A. R. and Rees, C. W. eds., Pergamon Press, Oxford, 1984) from a heteroaryl-substituted tetrazole of Formula (I).

In Schemes 1 to 3 below, W, X, Y, Z, A and B are as defined above for Formula (I).

Scheme 1

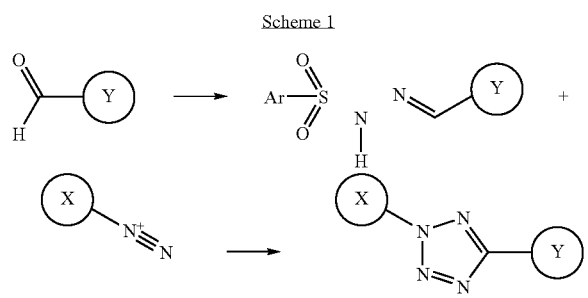

Referring to Scheme 1, ring system Y containing an aldehyde moiety (prepared using synthetic chemistry techniques well known in the art) is reacted with an arylsulfonylhydrazide in a suitable solvent (e.g. EtOH, MeOH, THF, DME, DMF etc.) at a temperature between 0° C. to 100° C. for 5 to 60 min to form an arylsulfonylhydrazone. An amine-substituted X (prepared using synthetic chemistry techniques well known in the art) is treated with nitrous acid, at a temperature of −10° C. to 0° C., in a suitable solvent such as, for example, water. In this manner an arenediazonium species is generated which then reacts with an arylsulfonylhydrazone in a 1,3-dipolar cycloaddition reaction to form a substituted tetrazole as shown (for example, see A. S. Shawali et al., *J. Heterocyclic Chem.* 1979, 16, 123-128). The product from Scheme 1, a disubstituted tetrazole, can be isolated and purified employing standard techniques, such as solvent extraction, acid-base extraction, chromatography, crystallization, distillation and the like.

Scheme 2

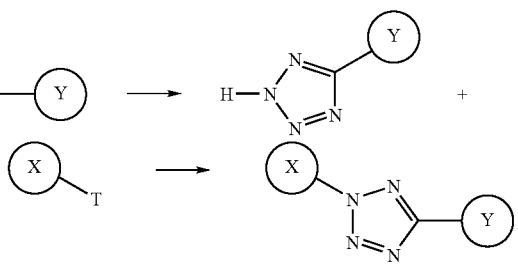

As shown in Scheme 2 above, Y substituted with a nitrile functional group (prepared using methods well known in the art) is reacted with an azide moiety, such as $LiN_3$, $NaN_3$ or $TMSN_3$, in a suitable solvent (e.g. toluene, benzene, xylenes etc.) at a temperature in the range of about 25° C. to 180° C. to form a monosubstituted tetrazole. This reaction can conveniently be performed with an added catalyst such as dibutyltin oxide. The resulting tetrazole may then be coupled with X substituted with a group T. T maybe a metalloid species such as $B(OR)_2$, BiLn and the like and the reaction may be promoted with stoichiometric or catalytic amounts of metal salts such as $Cu(OAc)_2$, CuI or CuOTf and the like. Conveniently, a base (e.g. pyridine, $NEt_3$, $Cs_2CO_3$, $K_2CO_3$ etc.) will also be present and the reaction is carried out in a suitable solvent (e.g. DCM, THF, DME toluene, MeCN, DMF, $H_2O$ etc.). Additionally, molecular sieves may be used as a cocatalyst (see for example Fedorov, A. Y.; Finet, J-P. *Tetrahedron Lett.* 1999, 40, 2747-2748).

Alternatively T may be a halogen or other functional group capable of undergoing a metal catalyzed N-arylation cross-coupling reaction in which case additional promoters such as 1,10-phenanthrolene and dibenzylideneacetone may also be added to the reaction mixture. The cross-coupling reaction maybe carried out at ambient temperature or heated to a temperature between about 30° C. to 150° C. The reaction mixture is then maintained at a suitable temperature for a time in the range of about 4 to 72 hours, with 18 hours typically being sufficient (see for example Lam, P. Y. S.; Clark, C. G.; Saubern, S.; Adams, J.; Winters, M. P.; Cham, D. M. T.; Combs, A. *Tetrahedron Lett.* 1998, 39, 2941-2944 and Kiyomori, A.; Marcoux, J. F.; Buchwald, S. L. *Tetrahedron Lett.* 1999, 40, 2657-2660). The product from Scheme 2, a disubstituted tetrazole, can be isolated and purified employing standard techniques, such as solvent extraction, acid-base extraction, chromatography, crystallization, distillation and the like.

Scheme 3

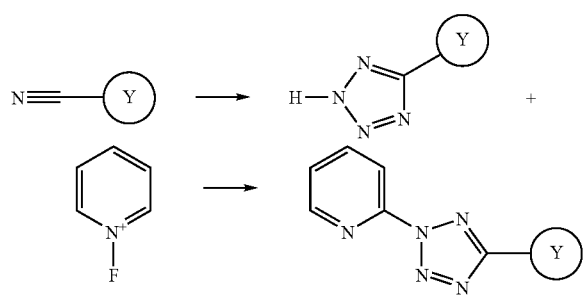

Referring to Scheme 3, the monosubstituted tetrazole is prepared as described in Scheme 2 from a suitable nitrile-substituted precursor. The tetrazole is then reacted with an N-fluoropyridinium salt, which may be optionally substituted, in the presence of a suitable base (e.g. MeONa, EtONa, tBuOK and the like) for a period of time sufficient for the reaction to proceed to completion, typically from about 1 to 12 h, at a temperature in the range of about −100° C. to 50° C., with −78° C. to 23° C. being advantageous (see for example Kiselyov, A. S. and Strekowski, L. *J. Heterocyclic Chem.* 1993, 30, 1361-1364). The product from Scheme 3, a 2-pyridyltetrazole derivative, can be isolated and purified employing standard techniques, such as solvent extraction, acid-base extraction, chromatography, crystallization, distillation and the like.

In the schemes above, ring systems X and/or Y may already contain a pendant ring W and/or Z. However, if required, ring systems W and/or Z may be appended to X and/or Y respectively where G and/or J are functional groups capable of undergoing a metal catalyzed-cross coupling (such as halogen, trifluoromethane-sulfonate, $B(OR)_2$, ZnX, $SnR_3$, and the like -Scheme 4 below). Ring systems W and Z are substituted with groups P, Q, S and T which may be for example, halogen, trifluoromethanesulfonate, $B(OR)_2$, ZnX, $SnR_3$, and the like. Typically, a transition metal catalyst such as $Pd(PPh_3)_4$, $Pd(PPh_3)_2Cl_2$, $Pd(OAc)_2$, $NiCl_2(dppe)$, $Pd(OAc)_2$, $Pd_2(dba)_3$, $Cu(OAc)_2$, CuI or the like may be employed, typically along with a suitable base such as $K_2CO_3$, $K_3PO_4$, $Cs_2CO_3$, $Et_3N$, pyridine or the like. Additionally, ligands such as BINAP, di-tert-butyl phosphinobiphenyl, di-cyclohexylphosphino biphenyl, tri tert-butylphosphine, XANTPHOS, triphenylarsine and the like may be added. The reaction is carried out in a suitable solvent such as toluene, DME, dioxane, THF, water or a combination of the above and is typically heated at 50° C.-150° C. for between 1 and 48 hrs. The reaction may be homogeneous or heterogeneous (see for example Miyaura, N.; Suzuki, A. *Chem. Rev.* 1995, 95, 2457-2483 and Dai, C.; Pu, G. C *J. Am. Chem. Soc.*, 2001, 123, 2719-2724 and Littke, A. F.; Fu, G. C. *Angew. Chem. Int. Ed.* 1999, 38, 6, 2411-2413 and Dai, C; Fu, G. C. *J. Am. Chem. Soc.* 2001, 123, 2719-2724).

Scheme 4

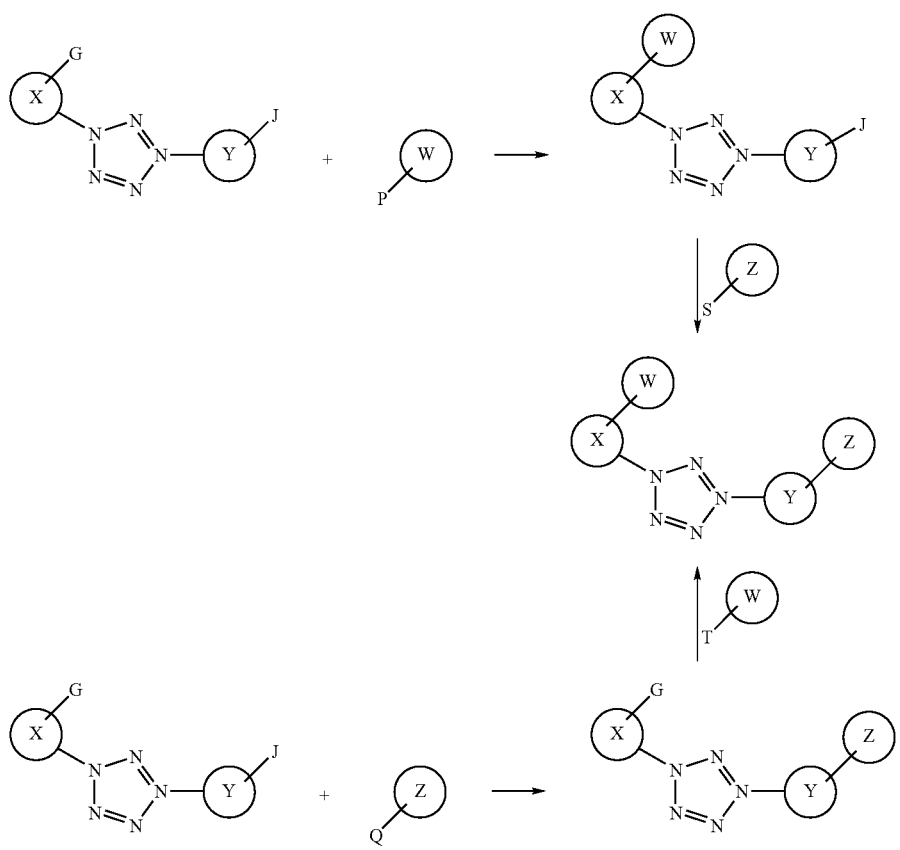

Alternatively ring systems W or Z may be a nitrogen containing heterocycle wherein the nitrogen is directly attached to the ring system X or Y respectively. In this case G and/or J are groups capable of undergoing a metal catalyzed N-aryl crosscoupling (such as halogen, trifluoromethane-sulfonate, $B(OR)_2$, ZnX, $SnR_3$, and the like—Scheme 4). Typically a transition metal such as CuI, $Cu(OAc)_2$, $Cu(OTf)_2$, Pd $(PPh_3)_4$, $Pd(PPh_3)_2Cl_2$, $Pd(OAc)_2$, $Pd_2(dba)_3$, $NiCl_2(dppe)$ is used along with a suitable base such as $K_2CO_3$, $K_3PO_4$, $Cs_2CO_3$, NaOtBu or the like. Additionally, phosphine containing ligands such as BINAP, di-tert-butyl phosphinobiphenyl, di-cyclohexylphosphino biphenyl, tri tert-butylphosphine, XANTPHOS and the like may be added. Further, additives such as 1,10-phenanthroline, 1,2-diaminocyclohexane, dibenzylideneacetone may be used. The reaction is typically carried out in a solvent such as toluene, DME, dioxane, THF, water or a combination of the above and is typically heated at 50° C.-150° C. for between 1 and 48 hrs. The reaction may be homogeneous or heterogeneous. The product from Scheme 4, can be isolated and 20 purified employing standard techniques, such as solvent extraction, acid-base extraction, chromatography, crystallization, distillation and the like (see for example Lam, P. Y. S.; Clark, C. G.; Saubern, S.; Adams, J.; Winters, M. P.; Cham, D. M. T.; Combs, A. *Tetrahedron Lett.* 1998, 39, 2941-2944 and Kiyomori, A.; Marcoux, J. F.; Buchwald, S. L. *Tetrahedron Lett.* 1999, 40, 2657-2660 and Wolfe, J. P.; Tomori, H.; Sadighi, J. P.; Yin, J.; Buchwald, S. L *J. Org. Chem.,* 2000, 65, 1158-1174 and Yin, J.; Buchwald, S. L.; *Org. Lett.,* 2000, 2, 1101-1104).

In addition, many of the heterocyclic intermediate compounds described above can be prepared using other synthetic chemistry techniques well known in the art (see *Comprehensive Heterocyclic Chemistry*, Katritzky, A. R. and Rees, C. W. eds., Pergamon Press, Oxford, 1984) and references cited there within.

EXAMPLE 1

1-Methyl-3-[3-(5-pyridin-2-yl-2H-tetrazol-2-yl)phenyl]imidazolidin-2-one 3-(3-Methylinidazolidin-2-one)aniline (76 mg, 0.4 mmol) was dissolved in 6N HCl (0.5 mL, 3.0 mmol), cooled to 0° C., and a solution of $NaNO_2$ (30 mg, 0.43 mmol) in $H_2O$ (0.5 mL) was added dropwise. The internal reaction temperature was maintained at <5° C. by the addition of ice chips to the flask. Separately, 2-pyridyl carboxaldehyde (43 mg, 0.4 mmol) and toluenesulfonyl hydrazide (69 mg, 0.4 mmol) were combined in ethanol (0.5 mL). The resulting reaction mixture was stirred at ambient temperature for 15 min and monitored by TLC for the disappearance of aldehyde (2,4-DNP stain). NaOH pellets (160 mg, 4.0 mmol) were then added along with $H_2O$ (1 mL) and the reaction mixture was cooled to 0° C. with an ice bath.

The 3-(3-methylimidazolidin-2-one)aniline diazotization reaction contents were then added dropwise via pipet. The resulting reaction was stirred for an additional 10 min at 0° C., then the cooling bath was removed and the reaction was allowed to warm to ambient temperature. The crude mixture was diluted with EtOAc (10 mL) and washed with $H_2O$ (3×10 mL). The organic phase was dried ($MgSO_4$), filtered, and concentrated in vacuo. The residue was chromatographed on silica gel eluting with hexanes:EtOAc (3:1) to afford 2-[2-(3-(3-methylimidazolidin-2-one)phenyl)-2H-tetrazol-5-yl]pyridine as a pale orange solid. $^1$H-NMR ($CDCl_3$, 300 MHz) δ 8.84 (d, 1H), 8.33 (d, 1H), 8.20-8.21 (m, 1H), 7.98-8.02 (m, 1H), 7.87-7.92 (m, 2H), 7.41-7.54 (m, 2H), 3.89-3.95 (m, 2H), 3.52-3.57 (m, 2H), 2.93 (s, 3H. MS (ESI) 322.1 $(M+H)^+$.

Compound 1

2-[2-(4-Bromophenyl)-2H-tetrazol-5-yl]pyridine

Following the procedure described in EXAMPLE 1 for the synthesis of 1-methyl-3-[3-(5-pyridin-2-yl-2H-tetrazol-2-yl)phenyl]imidazolidin-2-one, but using 4-bromoaniline (17.2 g, 100 mmol) and pyridine-2-carboxaldehyde (10.7 g, 100 mmol), 2-[2-(4-bromophenyl)-2H-tetrazol-5-yl]pyridine was obtained as an orange solid. $^1$H-NMR ($CDCl_3$, 300 MHz) δ 8.83 (d, 1H), 8.33 (d, 1H), 8.15 (d, 2H), 7.96-7.87 (m, 1H), 7.70 (d, 2H), 7.44 (dd, 1H).

EXAMPLE 2

2-[2-(4-Pyridin-2-ylphenyl)-2H-tetrazol-5-yl]pyridine

A solution of 2-[2-(4-bromophenyl)-2H-tetrazol-5-yl]pyridine (300 mg, 1 mmol), 2-pyridylzinc bromide (0.5M in THF, 2 mL) and tetrakis-(triphenylphosphine)palladium(0) (100 mg, 0.085 mmol) in anhydrous THF (10 mL) was degassed for 15 min and heated to 60° C. After 4 hours, a further equivalent of 2- pyridylzinc bromide (0.5M in THF, 2 mL) was added and the reaction mixture was heated at reflux overnight. The reaction mixture was then quenched with brine (25 mL), extracted with EtOAc (3×25 mL), dried over $Na_2SO_4$ and concentrated in vacuo. The crude residue was chromatographed on silica gel, eluting with EtOAc to afford a yellow solid. This was dissolved in anhydrous THF (10 mL) and HCl in ether (1.5 equiv) was added and the resulting precipitate was filtered to afford a yellow solid.

$^1$H-NMR ($CD_3OD$, 300 MHz) δ 9.00-8.94 (m, 2H), 8.81-8.70 (m, 2H), 8.67-8.61 (m, 3H), 8.53 (d, 1H), 8.33 (d, 2H), 8.17-8.09 (m, 2H). MS (ESI) 301.1 $(M+H)^+$.

EXAMPLE 3

2-[2-(4-Pyridin-4-ylphenyl)-2H-tetrazol-5-yl]pyridine

A solution of 2-[2-(4-bromophenyl)-2H-tetrazol-5-yl]pyridine (300 mg, 1 mmol), potassium carbonate (0.276 g, 2.0 mmol), and pyridin-4-ylboronic acid (123 mg, 1 mmol) in ethylene glycol dimethyl ether (20 mL) and water (4 mL) was degassed with argon for 15 min. Then tetrakis (triphenylphosphine)palladium(0) (80 mg, 0.068 mmol) was added, the mixture degassed for another 15 min, and the solution was stirred at 65° C. for 12 h. The reaction mixture was then quenched with water (30 mL), extracted with EtOAc (3×30 mL) and washed with brine. The organic phase was dried over $Na_2SO_4$ and concentrated in vacuo. The crude residue was chromatographed on silica gel, eluting with EtOAc to afford a yellow solid. This was dissolved in anhydrous THF (10 mL) and HCl (1.5equiv) in ether was added. The resulting precipitate was filtered off to afford 2-[2-(4-ylphenyl)-2H-tetrazol-5-yl]pyridine as a yellow solid. $^1$H NMR (CD₃OD, 300 MHz) δ 8.99-8.97 (m, 3H), 8.74 (d, 1H), 8.62-8.54 (m, 5H), 8.35 (d, 2H), 8.05 (t, 1H). Ms (ESI) 301.0 (M+H)⁺.

Compound 2

2-[2-(3-Iodophenyl)-2H-tetrazol-5-yl]pyridine

Following the procedure described in EXAMPLE 1 for the synthesis of 1-methyl-3-[3-(5-pyridin-2-yl-2H-tetrazol-2-yl) phenyl]imidazolidin-2-one, but using 3-iodoaniline (11 g, 50 mmol) and pyridine-2-carboxaldehyde (4.7 mL, 50 mmol), 2-[2-(3-iodophenyl)-2H-tetrazol-5-yl]pyridine was obtained as a biege solid. ¹H-NMR (CDCl₃, 300 MH) δ NMR 8.92 (d, 1H), 8.69 (m, 1H), 8.44 (d, 1H), 8.30 (d, 1H), 8.03-8.06 (m, 1H), 7.87-7.88 (m, 1H), 7.56-7.59 (m, 1H), 7.32-7.35 (m, 1H).

EXAMPLE 4

2-{2-[3-(1H-Imidazol-1-yl)phenyl]-2H-tetrazol-5-yl}pyridine

2-[2-(3-Iodophenyl)-2H-tetrazol-5-yl]pyridine (520 mg, 1.5 mmol), imidazole (133 mg, 2.0 mmol), potassium carbonate (435 mg, 3.2 mmol), copper (I) iodide (57 mg, 0.3 mmol) and 1,2-diamino cyclohexane (90 µL, 0.8 mmol) were weighed into a flask and flushed with Ar(g). Dry dioxane (0.7 mL) was added and the reaction mixture heated at 100° C. for 18 h. The reaction mixture was then poured into NH₄OH (10% in H₂O), NH₄Cl (sat aq) (1/1, 10 mL) and shaken with EtOAc (30 mL). The organic layer was separated and the aqueous layer extracted with EtOAc (3×30 mL), the combined organics were dried over Na₂SO₄, filtered and concentrated onto silica gel. Purification by liquid chromatography on silica gel (hexane:EtOAc=90:10) gave a yellow solid. This was recrystallized from EtOAc/Hexane to give yellow crystals which were dissolved in CH₂Cl₂/Et₂O and HCl in ether (1.5 equiv) was added. The resulting precipitate was filtered off to afford 2-{2-[3-(1H-imidazol-1-yl)phenyl]-2H-tetrazol-5-yl}pyridine as a yellow solid. ¹H NMR ((CD₃)₂SO, 300 MHz) δ 9.94 (s, 1H), 8.23-8.84 (m, 1H), 8.68-8.69 (m, 1H), 8.48-8.49 (m, 1H), 8.39-8.42 (m, 1H), 8.30-8.33 (m, 1H) 8.07-8.13 (m, 2H), 7.97-8.03 (m, 2H), 7.63-7.67 (m, 1H). MS (ESI) 262.2 (MH-N₂)⁺.

Compound 3

2-(2-Methoxy-4-nitrophenyl)pyridine

2-Pyridylzinc bromide (15.0 mmol, 30.0 mL of 0.5M solution in THF) was added via syringe to a stirred solution of 2-iodo-5-nitroanisole (4.0 g, 14.3 mmol) and tetrakis(triphenylphosphine)palladium (828 mg, 0.7 mmol) in deoxygenated THF. The mixture was stirred at 60° C. for 16 h, followed by the addition of additional tetrakis(triphenylphosphine)palladium (170 mg, 0.14 mmol) and 2-pyridylzinc bromide (5.0 mmol, 10.0 mL of 0.5M solution in THF). Continued stirring at 60° C. resulted in the disappearance by TLC analysis of the starting material 2-iodo-5-nitroanisole. The reaction mixture was concentrated in vacuo, dissolved in EtOAc (200 mL) and partitioned with H₂O (100 mL). The EtOAc was washed with an additional portion of H₂O, then dried (MgSO₄), filtered, and concentrated in vacuo. The crude residue was purified by silica gel chromatography, eluting with 3:1 hexanes:EtOAc to afford 2-(2-methoxy4-nitrophenyl) as a white solid. ¹H-NMR (CDCl₃, 300 MHz) δ 8.75 (m, 1H), 7.95-7.98 (m, 2H), 7.86-7.91 (m, 2H), 7.75-7.80 (m, 1H), 7.28-7.33 (m, 1H), 3.98 (s, 3H).

Compound 4

3-Methoxy-4-pyridin-2-ylaniline

Tin(II) chloride dihydrate (6.77 g, 30.0 mmol) and 2-(2-methoxy-4-nitrophenyl)pyridine (2.30 g, 10.0 mmol) were combined in MeOH (100 mL) and stirred at reflux for 18 h. The reaction mixture was then cooled to RT and concentrated in vacuo. The residue was then partitioned with EtOAc (200 mL) and 1N aqueous NaOH (100 mL). The aqueous layer was washed with EtOAc (3×75 mL), and the combined EtOAc layers were back-extracted with H₂O (100 mL), dried (MgSO₄), filtered, and concentrated in vacuo. The resulting residue was purified by SiO₂ chromatography, eluting with 2:1 EtOAc:hexanes to afford 3-methoxy4-pyridin-2-ylaniline as an amber oil. ¹H-NMR (CDCl₃, 300 MHz) δ 8.63 (m, 1H), 7.78 (d, 1H), 7.57-7.67 (m, 2H), 7.04-7.13 (m, 1H), 6.34-6.41(dd, 1H), 6.26 (d, 1H), 3.72-3.92 (s, 2H), 3.72 (s, 3H).

Compound 5

3-Methoxy-4-(3-methyl-1,2,4-oxadiazol-5-yl)aniline

To a suspension of methyl amidoxime hydrochloride (1.8 g, 16.3 mmol) in TBF (80 mL) at rt was added NaH (1.32 g of a 60% dispersion in oil, 33.1 mmol). Reaction was stirred at 60° C. for 15 min, then methyl-4-amino-2-methoxy benzoate (1.0 g, 5.5 mmol) was added and stirring was continued. After 4 h, DMF (60 mL) was added to aid solubility and the reaction temperature was increased to 90° C. After 1.5 h, reaction was complete by TLC analysis. Reaction was quenched at rt with H₂O (20 mL), then concentrated via rotary evaporation. The crude residue was partitioned in a separatory funnel with EtOAc (100 mL) and H₂O (50 mL). The EtOAc layer was washed with an additional portion of H₂O (50 mL), then dried (MgSO₄), filtered, and concentrated in vacuo. The residue was then purified by silica gel chromatography, eluting with 3:1 EtOAc:Hexanes to afford 3-methoxy-4-(3-methyl-1,2,4-oxadiazol-5-yl)aniline as a tan solid. ¹H NMR (CD₃OD, 500 MHz) δ 7.72 (m, 1H), 6.31-6.37 (m, 2H), 3.87 (s, 3H), 2.36 (s, 3H). MS (EST) 206.1 (M+H)⁺.

Compound 6

2-{2-[3-(Trimethylstannyl)phenyl]-2H-tetrazol-5-yl}pyridine

A solution of 2-[2-(3-bromophenyl)-2H-tetrazol-5-yl]pyridine (750 mg, 2.5 mmol), hexamethylditin (895 mg, 2.8 mmol), cesium fluoride (418 mg, 2.8 mmol) and tetrakis(triphenylphosphine)palladium(0) (145 mg, 0.13 mmol) in 20 mL of dry toluene was degassed with nitrogen for 15 min. The solution was heated to 100° C. and stirred under nitrogen for 6 h. The reaction mixture was allowed to cool to rt, diluted with 10 mL of ethyl acetate, and then filtered through a pad of Celite. Water (40 mL) was added to the solution, extracted with 3×40 mL of ethyl acetate, and then the organic extracts were combined and washed with brine. The extracts were dried over Na₂SO₄, filtered, and then concentrated. The crude material was chromatographed over silica gel, eluting with 30% EtOAc/hexanes. Purification yielded a yellow oil, which crystallized upon sitting to afford 2-{2-[3-(trimethylstannyl)

phenyl]-2H-tetrazol-5-yl}pyridine as a light yellow solid. ¹H NMR (CD₃OD, 500 MHz) δ 8.72-8.88 (m, 1H), 8.39-8.43 (m, 2H), 8.21-8.22 (m, 111), 7.92-7.95 (m, 1H), 7.60-7.62 (m, 1H), 7.52-7.55 (m, 1H), 7.46-7.48 (m, 1H), 0.40 (s, 9H).

EXAMPLE 5

2-[2-(2-Pyrazin-3-ylphenyl)-2H-tetrazol-5-yl]pyridine

A vial containing 2-[2-(3-trimethylstannylylphenyl)-2H-tetrazol-5-yl]pyridine (70 mg, 0.18 mmol), chloropyrazine (23 mg, 2.0 mmol), tris(dibenzylideneacetone)dipalladium (0) (10 mg, 0.01 mmol), cesium fluoride (60 mg, 0.4 mmol), and tri-t-butyl-phosphine (0.101 mL of 10% weight in hexanes, 0.05 mmol) was sealed with a septum cap and purged with nitrogen. Degassed dioxane (2 mL) was added to the vial via syringe and stirred under nitrogen for 10 min. The reaction mixture was subjected to microwave conditions at 140° C. for 600 s using the Personal Chemistry Smith Creator microwave instrument. The reaction mixture was diluted with EtOAc, then extracted with 3× EtOAc and water. The organic extracts were combined, dried over NaSO₄, filtered, and then concentrated. The crude material was chromatographed over silica gel, eluting with 75% EtOAc/hexanes, to yield a yellow solid. The solid was further purified with a Waters preparatory HPLC instrument to yield 2-[2-(2-pyrazin-3-ylphenyl)-2H-tetrazol-5-yl]pyridine as a light yellow solid. ¹H NMR (CD₃OD, 500 Miz) 9.34 (s, 1H), 9.08 (s, 1H), 8.98 (m, 1H), 8.86 (s, 1H), 8.81 (m, 1H), 8.69 (m, 1H), 8.62 (t, 1H), 8.41-8.45 (m, 2H), 8.08 (m, 1H), 7.90 (t, 1H). MS 302 (M+H)⁺.

EXAMPLE 6

2-[2-(4-Morpholin-3-ylphenyl)-2H-tetrazol-5-yl]pyridine

To a flask containing 2-[2-(4-bromophenyl)-2H-tetrazol-5-yl]pyridine (150 mg, 0.5 mmol), tris(dibenzylideneacetone)dipalladium(0) (26 mg, 0.025 mmol), 2-(dicyclohexylphosphino)biphenyl (18 mg, 0.05 mmol), and sodium t-butoxide (67 mg, 0.7 mmol), degassed toluene was added and the resulting mixture was stirred under nitrogen until homogeneity. Morpholine (53 μL, 0.6 mmol) was added to the mixture via syringe, and the reaction was heated to 80° C. The solution was then stirred for 18 h under nitrogen. The reaction mixture was quenched with water (20 mL), extracted with EtOAc (3×20 mL), and washed with brine. The organic phase was dried over Na₂SO₄ and concentrated in vacuo. The crude residue was chromatographed on silica gel eluting with 40% EtOAc in hexanes to afford a yellow solid. This was dissolved in anhydrous THF (10 mL) and HCl (1.5equiv) in ether was added, the precipitate was filtered to afford 2-[2-(4-morpholin-3-ylphenyl)-2H-tetrazol-5-yl]pyridine as a yellow solid. ¹H NMR ((CD₃)₂SO, 300 MHz) δ 8.82 (d, 1H), 8.28 (d, 1H), 8.08 (dt, 1H), 7.51-7.68 (m, 4H), 7.23 (m, 1H), 3.77 (m, 4H), 3.25 (m, 4H). MS (ESI) MS 309 (M+H)⁺.

EXAMPLE 7

2-{2-[3-(2H-Tetrazol-5-yl)phenyl]-2H-tetrazol-5-yl}pyridine 3-(5-Pyridin-2-yl-2H-tetrazol-2-yl)benzonitrile (300 mg, 1.21 mmol), sodium azide (86.5 mg, 1.33 mmol) and zinc bromide (272 mg, 1.21 mmol) were suspended in water (3 mL). The reaction was capped with a reflux condenser and stirred at 90° C. for 24 h, after which time it was cooled to rt and HCl 3N (1.5 mL) and ethyl acetate (20 mL) were added and the mixture stirred vigorously until no solid was left. The organic layer was isolated and aqueous layer extracted with ethyl acetate (2×20 mL). The combined organic layers were evaporated, 10 mL of 0.25N NaOH was added, the mixture was stirred for 30min, until the original precipitate was dissolved and a suspension of zinc hydroxide was formed. The suspension was filtered, and the solid washed with 10 ml 1 N NaOH. To the filtrate was added 2 mL of 3N HCl with stirring causing the tetrazole to precipitate. The tetrazole was filtered and washed with 5 mL of 3N HCl and dried in vacuo to afford white powder. ¹H NMR (CD₃OD, 500 MHz) δ 8.91 (s, 1H), 8.83 (d, 1H), 8.41 (d, 1H), 8.32-8.25 (m, 2H), 8.09 (t, 1H), 7.95 (t, 1H), 7.64 (t, 1H). MS 292.1 (M+H)⁺.

EXAMPLE 8

2-Pyridin-2-yl-5-(5-pyridin-2-yl-2H-tetrazol-2-yl)benzonitrile

2-[2-(3-Fluoro-4-pyridin-2-ylphenyl)-2H-tetrazol-5-yl]pyridine (300 mg, 0.94 mmol) and sodium cyanide (92 mg, 1.9 mmol ) were suspended in methyl sulfoxide (6 ml). The reaction was capped with a reflux condenser and stirred at 170° C. for 16 h, after which time it was cooled to ambient temperature. To the reaction solution added ethyl acetate (10 ml) then water (60 ml) causing 2-pyridin-2-yl-5-(5-pyridin-2-yl-2H-tetrazol-2-yl)benzonitrile to precipitate as white powder. ¹H NMR (CD₃OD, 500 MHz) δ 8.84-8.81 (m, 2H), 8.73 (d, 1H), 8.60 (dd 1H), 8.32 (d, 1H), 8.24 (d, 1H), 8.09-8.07 (m, 2H), 8.01 (d, 1H), 7.64 (m, 1H), 7.58(m, 1H). MS 326.2 (M+H)⁺.

EXAMPLE 9 to EXAMPLE 347 shown below were all prepared similarly to the schemes and procedures described above (ND=not determined).

| EXAMPLE | Structure | ¹H NMR | MS (ESI) |
|---------|-----------|--------|----------|
| 9. | 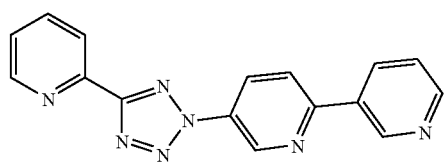 | 9.72 (m, 2H), 9.45 (d, 1H), 8.90-8.99 (m, 3H), 8.77 (d, 1H), 8.55-8.62 (m, 2H), 8.32 (dd, 1H), 8.07 (dd, 1H). | MS 302.1 (M + H)⁺. |

-continued

| EXAMPLE | Structure | ¹H NMR | MS (ESI) |
|---|---|---|---|
| 10. | 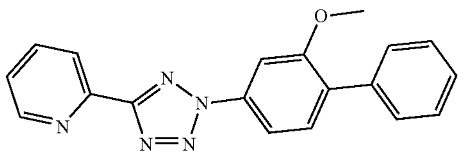 | 8.87 (d, 1H), 8.38 (d, 1H), 7.98-7.92 (m, 2H), 7.88 (d, 1H), 7.59-7.38 (m, 7H), 3.97 (s, 3H). | MS 330.6 (M + H)+. |
| 11. | 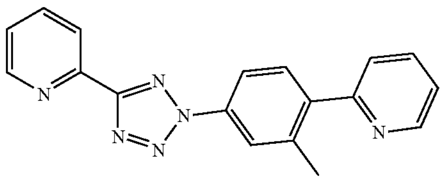 | 8.75-8.77 (d, 1H), 8.66-8.68 (d, 1H), 8.35-8.38 (d, 1H), 8.23 (s, 1H), 8.15-8.19 (d, 1H), 8.06-8.10 (t, 1H), 7.96-8.00 (t, 1H), 7.58-7.62 (m, 3H), 7.46-7.50 (m, 1H), 2.45 (s, 3H) | MS 315.1 (M + H)+. |
| 12. | 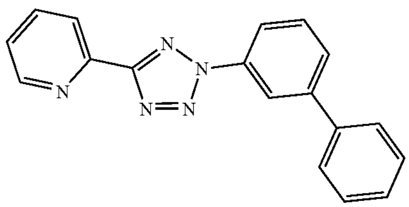 | ND | MS 300.1 (M + H)+. |
| 13. | 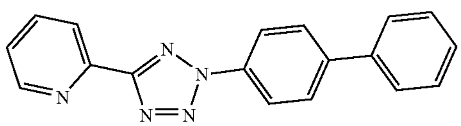 | ND | MS 300.2 (M + H)+. |
| 14. | 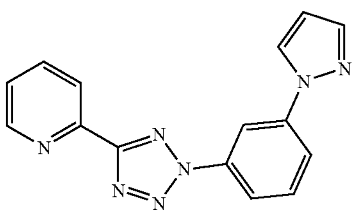 | 8.82-8.83 (m, 1H), 8.76 (d, 1H), 8.67 (t, 1H), 8.30 (d, 1H), 8.06-8.14 (m, 3H), 7.81-7.86 (m, 2H), 7.64 (ddd, 1H), 6.64 (dd, 1H). | MS 290.2 (M + H)+. |
| 15. | 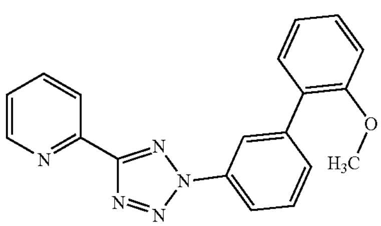 | 8.83 (d, 1H), 8.50 (s, 1H), 8.32 (d, 1H), 8.18-8.20 (m, 1H), 8.08-8.11 (m, 1H), 7.97 (d, 1H), 7.81 (t, 1H), 7.64 (m, 1H), 7.47 (t, 1H), 7.39 (d, 1H), 7.34 (m, 1H), 7.05 (dd, 1H), 3.92 (s, 3H). | MS 330 (M + H)+ |
| 16. | 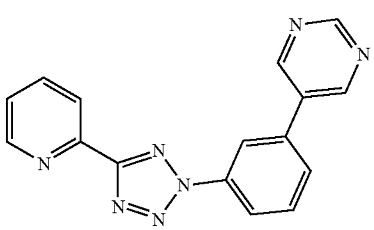 | 9.32 (s, 2H), 9.29 (s, 1H), 8.83 (m, 1H), 8.59 (t, 1H), 8.28-8.33 (m, 2H), 8.07-8.13 (m, 2H), 7.90 (t, 1H), 7.62 (m, 1H). | MS 302 (M + H)+ |
| 17. | 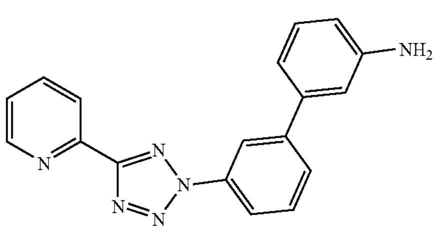 | 8.83 (m, 1H), 8.41 (m, 1H), 8.31 (d, 1H), 8.25-8.27 (m, 1H), 8.10 (dt, 1H), 7.95 (d, 1H), 7.86 (t, 1H), 7.82 (d, 1H), 7.76 (m, 1H), 7.63-7.66 (m, 2H), 7.40 (d, 1H), 3.90 (brm). | MS 315 (M + H)+ |

-continued

| EXAMPLE | Structure | ¹H NMR | MS (ESI) |
|---------|-----------|--------|----------|
| 18. | 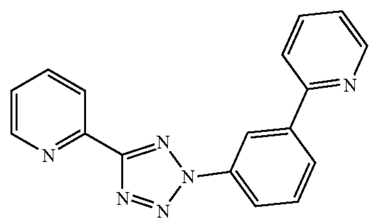 | 8.92-8.93 (m, 1H), 8.80-8.82 (m, 1H), 8.75-8.77 (m, 1H), 8.23-8.34 (m, 3H), 8.14-8.17 (m, 1H), 8.07 (ddd, 1H), 7.97 (ddd, 1H), 7.82 (dd, 1H), 7.62 (ddd, 1H), 7.44-7.48 (m, 1H). | MS 301 (M + H)+. |
| 19. | 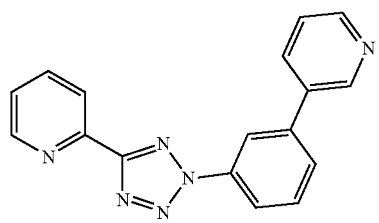 | 9.04 (d, 1H, J=2.8 Hz), 8.81-8.30 (m, 1H), 8.67 (dd, 1H), 8.47-8.48 (m, 1H), 8.30-8.32 (m, 1H), 8.23-8.28 (m, 2H), 8.08 (ddd), 8.02-8.04 (m, 1H), 7.85 (dd, 1H), 7.63 (ddd, 1H), 7.55-7.60 (m, 1H). | MS 301 (M + H)+. |
| 20. | 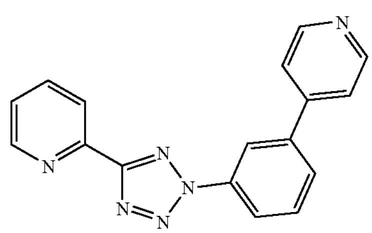 | 8.81-8.83 (m, 1H), 8.71-8.73 (m, 2H), 8.51-8.52 (m, 1H), 8.26-8.32 (m, 2H), 8.05-8.11 (m, 2H), 7.84-7.89 (m, 3H), 7.62 (ddd, 1H). | MS 301 (M + H)+. |
| 21. | 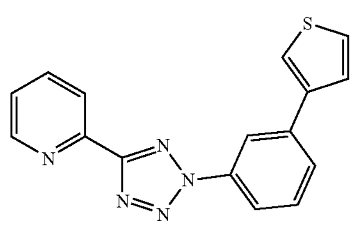 | 8.83 (m, 1H), 8.47 (m, 1H), 8.31 (m, 1H), 8.18 (t, 1H), 8.09 (m, 1H), 8.08 (t, 1H), 8.01 (m, 1H), 7.72-7.79 (m, 3H), 7.63 (m, 1H). | MS 306 (M + H)+ |
| 22. | 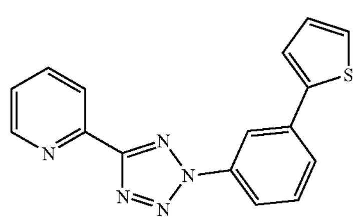 | 8.84 (d, 1H), 8.39 (m, 1H), 8.32 (d, 1H), 8.12 (d, 1H), 8.08 (dt, 1H), 7.96 (d, 1H), 7.77 (d, 1H), 7.76 (d, 1H), 7.71 (d, 1H), 7.64 (dd, 1H), 7.24 (dd, 1H) | MS 306 (M + H)+ |
| 23. | 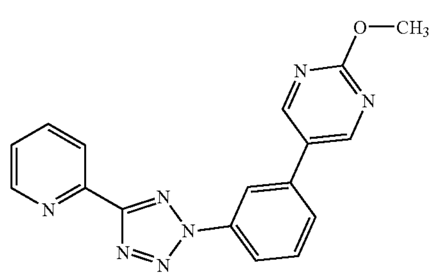 | 9.10 (s, 2H), 8.83 (m, 1H), 8.51 (m, 1H), 8.31 (d, 1H), 8.20 (m, 1H), 8.12 (dt, 1H), 8.06 (m, 1H), 7.86 (t, 1H), 7.58-7.68 (m, 2H), 4.05 (s, 3H). | MS 332 (M + H)+ |

-continued

| EXAMPLE | Structure | ¹H NMR | MS (ESI) |
|---|---|---|---|
| 24. | (pyridin-2-yl tetrazole linked to phenyl with 6-methoxypyridin-3-yl substituent) | 8.82 (m, 1H), 8.65 (d, 1H), 8.41 (t, 1H), 8.31 (d, 1H), 8.16-8.21 (m, 2H), 8.09 (dt, 1H), 7.96 (d, 1H), 7.81 (t, 1H), 7.64 (m, 1H), 6.99 (d, 1H), 3.93 (s, 3H). | MS 331 (M + H)⁺ |
| 25. | (pyridin-2-yl tetrazole linked to 2-chloro-4-(pyridin-2-yl)phenyl) | 8.47 (d, 1H), 8.38 (d, 1H), 7.98 (s, 1H), 7.91-7.82 (m, 3H), 7.70-7.65 (t, 1H) 7.57-7.53 (m, 1H), 7.34-7.31 (t, 1H), 7.22-7.20 (m, 1H), 6.26 (b, 1H) | MS 357.7 (M + Na)⁺ |
| 26. | (pyridin-2-yl tetrazole linked to 2-methoxy-4-(pyridin-2-yl)phenyl) | 8.92 (d, 1H), 8.84 (d, 1H), 8.74 (dd, 1H), 8.50 (d, 1H) 8.39 (d, 1H), 8.09-8.27 (m, 4H), 8.01 (d, 1H), 7.73-7.78 (m, 1H), 4.14 (s, 3H). | MS 331.0 (M + H)⁺. |
| 27. | (pyridin-2-yl tetrazole linked to 2-methoxy-4-(thiazol-2-yl)phenyl) | 8.97 (d, 1H), 8.80 (d, 1H), 8.66 (dd, 1H), 8.52 (d, 1H), 8.18-8.21 (m, 2H), 8.09-8.14 (m, 2H), 8.03 (d, 1H), 4.30 (s, 3H). | MS 337.0 (M + H)⁺. |
| 28. | (pyridin-2-yl tetrazole linked to 3-chloro-5-(pyridin-3-yl)phenyl) | 9.42 (s, 1H), 9.11 (d, 1H), 8.99 (d, 1H), 8.91 (br, 1H), 8.72 (s, 1H), 8.70~8.60 (m, 1H), 8.50~8.55 (m, 1H), 8.44 (dd, 1H), 8.28 (dd, 1H), 8.21 (m, 1H), 7.88~7.84 (m, 1H). | MS 335.1 (M + H)⁺. |
| 29. | (pyridin-2-yl tetrazole linked to 4-methoxy-3-(pyridin-3-yl)phenyl) | 8.24 (s, 1H), 8.94 (dd, 1H), 8.90~8.80 (m, 1H), 8.55 (d, 1H), 8.45~8.8.33 (m, 3H), 8.23 (dd, 1H), 8.78~8.82 (m, 1H), 7.55 (d, 1H), 4.03 (s, 3H). | MS 331.0 (M + H)⁺. |
| 30. | (pyridin-2-yl tetrazole linked to 4-(pyrazol-1-yl)phenyl) | ND | MS 290.0 (M + H)⁺. |
| 31. | (pyridin-2-yl tetrazole linked to 3-chloro-4-morpholinophenyl) | 8.84-8.86 (d, 1H), 8.34-8.37 (m, 2H), 8.14-8.18 (m, 1H), 7.89-7.95 (m, 1H), 7.43-7.47 (m, 1H), 7.18-7.21 (d, 1H), 3.91-3.94 (t, 4H), 3.15-3.18 (t, 4H). | MS 343.0 (M + H)⁺. |

-continued

| EXAMPLE | Structure | ¹H NMR | MS (ESI) |
|---------|-----------|--------|----------|
| 32. | 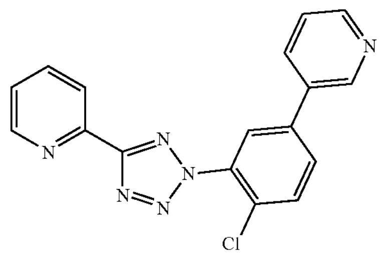 | 9.37 (s, 1H) 9.07 (d, 1H), 8.96 (br, 2H), 8.78-8.75 (m, 1H), 8.60 (t, 1H), 8.46 (s, 1H), 8.24-8.23 (m, 2H), 8.13-8.04 (m, 2H). | MS 335.0 (M + H)⁺ |
| 33. | 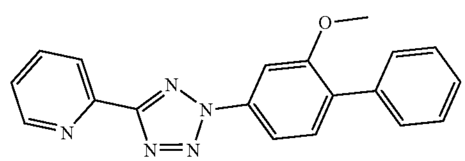 | 8.87 (d, 1H), 8.38 (d, 1H), 7.98-7.92 (m, 2H), 7.88 (d, 1H), 7.59-7.38 (m, 7H), 3.97 (s, 3H). | MS 330.6 (M + H)⁺. |
| 34. | 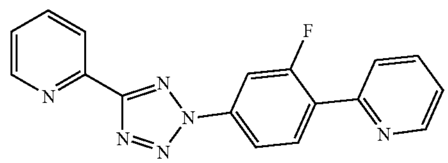 | 9.05 (m, 2H), 8.84 (m, 2H), 8.75 (1H), 8.46 (m, 3H), 8.219 (m, 3H). | MS 318.8 (M + H)⁺. |
| 35. | 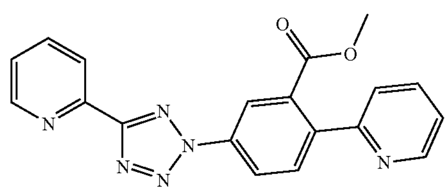 | 8.86 (d, 1H), 8.75 (s, 1H), 8.69 (s, 1H), 8.49 (d, d 1H), 8.38 (d, 1H), 7.93 (t, 1H), 7.80 (m, 2H), 7.57 (d, 1H), 7.47 (t, 1H), 7.32 (t, 1H). | MS 359.0 (M + H)⁺. |
| 36. | 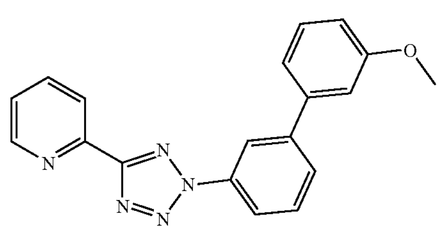 | 8.82 (d, 1H), 8.4 (s, 1H), 8.33 (d, 1H), 8.20 (m, 1H), 8.1 (m, 1H), 7.97 (d, 1H), 7.81 (t, 1H), 7.62 (dd, 1H), 7.48 (t, 1H), 7.38 (d, 1H), 7.34 (m, 1H), 7.05 (dd, 1H), 3.85 (s, 3H). | MS 330 (M + H)⁺ |
| 37. | 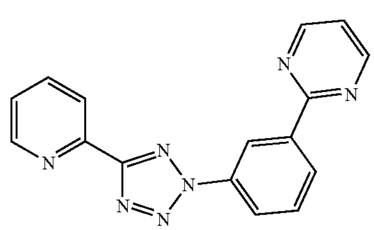 | 9.20 (s, 1H), 9.02 (d, 2H), 8.84 (d, 1H), 8.64 (d, 1H), 8.38 (dd, 1H), 8.33 (d, 1H), 8.11 (dt, 1H), 7.89 (t, 1H), 7.65 (dd, 1H), 7.58 (t, 1H). | MS 302 (M + H)⁺ |
| 38. | 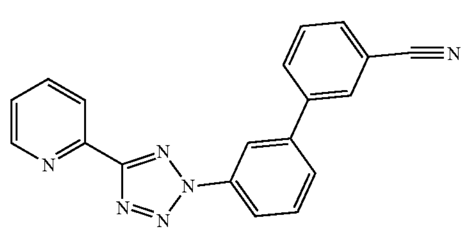 | 8.83 (d, 1H), 8.52 (m, 1H), 8.38 (m, 1H), 8.32 (d, 1H), 8.25 (m, 1H), 8.20 (m, 1H), 8.10 (dt, 1H), 8.05 (d, 1H), 7.94 (d, 1H), 7.85 (t, 1H), 7.76 (t, 1H), 7.64 (m, 1H). | MS 325 (M + H)⁺ |

-continued

| EXAMPLE | Structure | ¹H NMR | MS (ESI) |
|---|---|---|---|
| 39. | 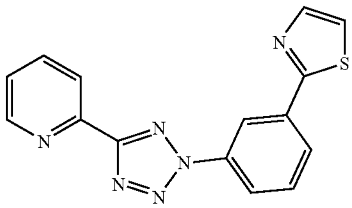 | 8.84 (d, 1H), 8.74 (d, 1H), 8.32 (m, 2H), 8.21 (d, 1H), 8.10 (m, 1H), 8.06 (m, 1H), 7.96 (m, 1H), 7.87 (m, 1H), 7.64 (m, 1H). | MS 307 (M + H)⁺ |
| 40. | 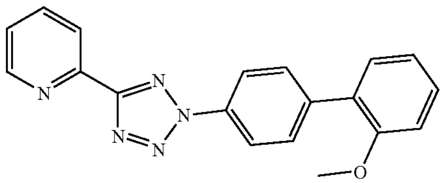 | 8.83 (d, 1H), 8.40 (s, 1H), 8.32 (d, 1H), 8.19 (m, 1H), 8.10 (dt, 1H), 7.97 (d, 1H), 7.81 (t, 1H), 7.64 (dd, 1H), 7.47 (t, 1H), 7.38 (d, 1H), 7.34 (m, 1H), 7.05 (dd, 1H), 3.88, (s, 3H). | MS 330 (M + H)⁺ |
| 41. | 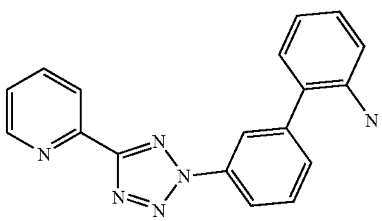 | 8.82 (d, 1H), 8.25-8.32 (m, 3H), 8.09 (dt, 1H), 7.85 (t, 1H), 7.79 (d, 1H), 7.64 (m, 1H), 7.47 (m, 2H), 7.41 (m, 1H), 7.34 (m, 1H), 3.73 (bm, 2H). | MS 315 (M + H)⁺ |
| 42. | 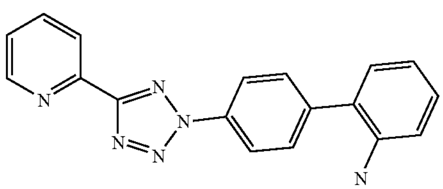 | 8.84 (d, 1H), 8.30-8.32 (m, 3H), 8.10 (m, 1H), 7.87 (d, 2H), 7.65 (dd, 1H), 7.44-7.49 (m, 3H), 7.36 (m, 1H). | MS 315 (M + H)⁺ |
| 43. | 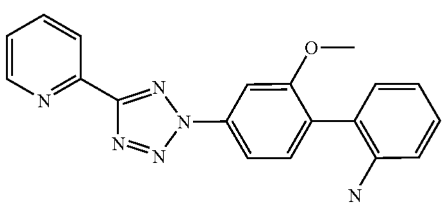 | 9.06 (d, 1H), 9.00, (d, 1H), 8.78 (dd, 1H), 8.23 (dd, 1H), 8.06 (m, 2H), 7.70 (d, 1H), 7.64 (m, 2H), 7.58 (m, 1H), 7.54 (m, 1H), 4.09 (s, 3H). | MS 345.3 (M + H)⁺ |
| 44. | 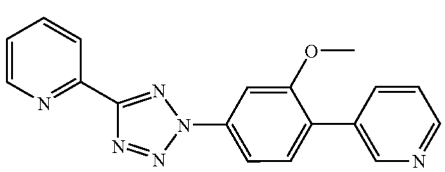 | 9.22 (s, 1H), 9.00 (d, 1H), 8.93 (d, 1H), 8.89 (d, 1H), 8.83 (d, 1H), 8.72 (dd, 1H), 8.23 (dd, 1H), 8.09-8.16 (m, 3H), 7.89 (d, 1H), 4.09 (s, 3H). | MS 331.3 (M + H)⁺ |
| 45. | 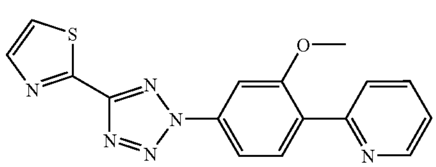 | 8.89 (d, 1H), 8.68 (dd, 1H), 8.34 (d, 1H), 8.11-8.15 (m, 3H), 8.07 (dd, 1H), 7.97-8.00 (m, 2H), 4.12 (s, 3H). | MS 336.8 (M + H)⁺ |

-continued

| EXAMPLE | Structure | ¹H NMR | MS (ESI) |
|---|---|---|---|
| 46. | 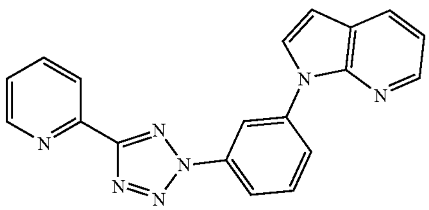 | 8.94 (t, 1H), 8.82 (d, 1H), 8.41 (dd, 1H), 8.31 (d, 1H), 8.19 (dd, 1H), 8.18 (d, 1H), 8.16 (d, 1H), 8.14 (s, 1H), 8.09 (dt, 1H), 7.88 (t, 1H), 7.64 (ddd, 1H), 7.29 (dd, 1H), 6.83 (d, 1H) | MS 340 (M + H)⁺ |
| 47. | 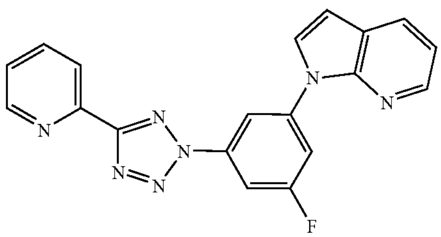 | 8.98 (br s, 1H), 8.83 (d, 1H), 8.45 (dd, 1H), 8.32 (d, 1H), 8.26 (dt, 1H), 8.26 (d, 1H), 8.16 (dd, 1H), 8.10 (dt, 1H), 8.01 (dt, 1H), 7.64 (ddd, 1H), 7.32 (dd, 1H), 6.86 (d, 1H) | MS 358 (M + H)⁺ |
| 48. | 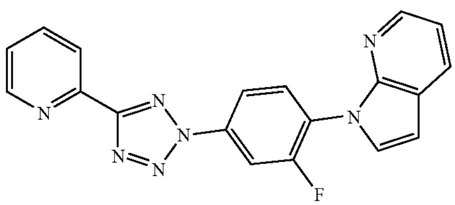 | 8.84 (d, 1H), 8.35 (dd, 1H), 8.32 (s, 1H), 8.31 (dd, 1H), 8.23 (dd, 1H), 8.15 (dd, 1H), 8.14-8.08 (m, 2H), 7.87 (dd, 1H), 7.64 (ddd, 1H), 7.27 (dd, 1H), 6.83 (d, 1H) | MS 358 (M + H)⁺ |
| 49. | 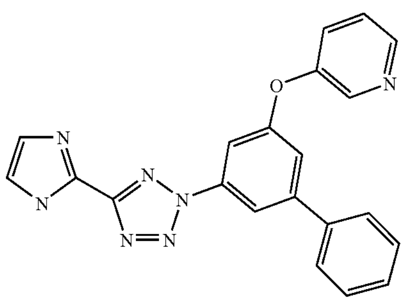 | 8.60 (s, 1H), 8.52-8.51 (d, 1H), 8.364-8.358 (t, 1H), 7.923-7.919 (t, 1H), 7.88-7.7.86 (m, 1H), 7.77-7.72 (m, 4H), 7.697-7.658 (m, 2H), 7.56-7.53 (m, 2H), 7.50-7.47 (m, 1H). | MS 410.97 (M⁺ + H). |
| 50. | 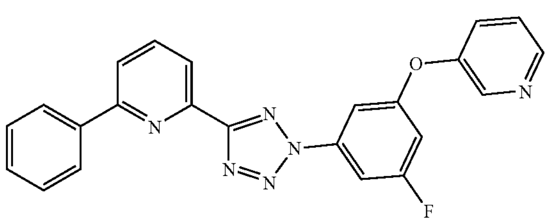 | 8.85 (s, 1H), 8.68-8.67 (d, 1H), 8.33-8.31 (dd, 1H), 8.27-8.55 (d, 1H), 8.17-78.00 (m, 7H), 7.54-7.46 (m, 3H), 7.31-7.30 (m, 1H). | MS 382.41 (M⁺ + H). |
| 51. | 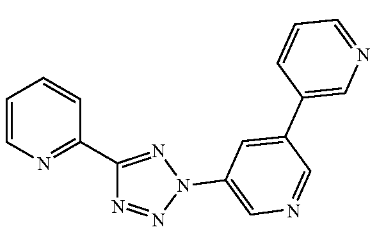 | 9.60 (d, 1H), 9.01 (d, 1H), 8.99 (d, 1H), 8.87 (d, 1H), 8.78 (m, 1H), 8.75 (d, 1H), 8.39 (d, 1H), 8.02 (d, 1H), 7.94 (dd, 1H), 7.50 (m, 2H). | MS 302.2 (M⁺ + H). |

-continued

| EXAMPLE | Structure | ¹H NMR | MS (ESI) |
|---|---|---|---|
| 52. | 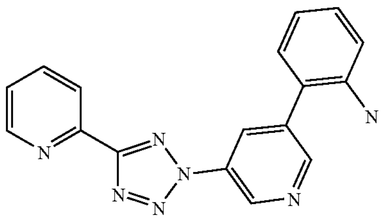 | 9.51 (d, 1H), 8.90 (d, 1H), 8.85 (d, 1H), 8.70 (dd, 1H), 8.36 (d, 1H), 7.92 (dd, 1H), 7.46 (m, 1H), 7.25 (dd, 1H), 7.19 (d, 1H), 6.91 (dd, 1H), 6.84 (d, 1H), 3.89 (s, 2H). | MS 316.5 (M⁺ + H). |
| 53. | 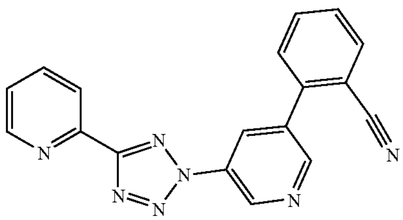 | 9.66 (d, 1H), 8.97 (s, 1H), 8.86 (d, 1H), 8.79 (m, 1H), 8.38 (d, 1H), 7.94 (dd, 1H), 7.87 (d, 1H), 7.78 (dd, 1H), 7.63 (m, 2H), 7.47 (m, 1H). | MS 326.4 (M⁺ + H). |
| 54. | 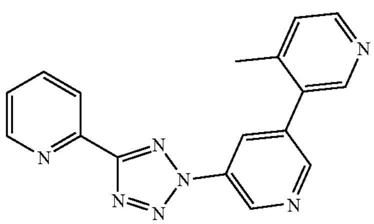 | 9.51 (d, 1H), 8.79 (d, 1H), 8.74 (d, 1H), 8.68 (m, 1H), 8.49 (m, 2H), 8.36 (d, 1H), 8.03 (dd, 1H), 7.58 (m, 1H), 7.40 (d, 1H), 2.42 (s, 3H). | MS 316.0 (M⁺ + H). |
| 55. | 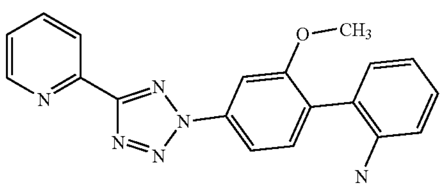 | 9.06 (d, 1H), 9.00 (d, 1H), 8.79 (dd, 1H), 8.23 (dd, 1H), 8.09 (m, 2H), 7.70 (d, 1H), 7.64 (m, 2H), 7.58 (m, 1H), 7.53 (m, 1H), 4.07 (s, 3H). | MS 345.3 (M⁺ + H). |
| 56. | 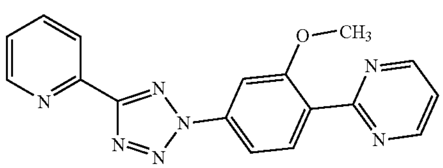 | 9.25 (d, 2H), 8.94 (s, broad, 1H), 8.70 (s, broad, 1H), 8.49 (m, 2H), 8.18 (s, 1H), 8.13 (d, 1H), 7.97 (s, broad, 1H), 7.91 (dd, 1H), 4.23 (s, 3H). | MS 331.9 (M⁺ + H). |
| 57. | 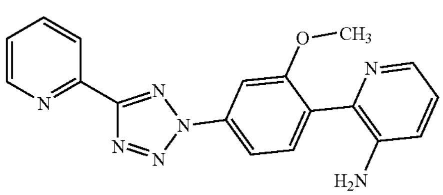 | ND | MS 346.3 (M⁺ + H). |
| 58. | 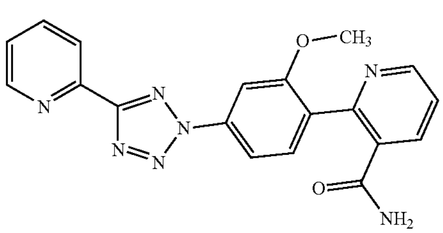 | 9.06 (m, 2H), 8.81-8.92 (m, 3H), 8.25 (m, 2H), 8.16 (d, 1H), 8.14 (s, 1H), 7.93 (d, 1H), 4.07 (s, 3H). | MS 374.3 (M⁺ + H). |

-continued

| EXAMPLE | Structure | ¹H NMR | MS (ESI) |
|---|---|---|---|
| 59. | 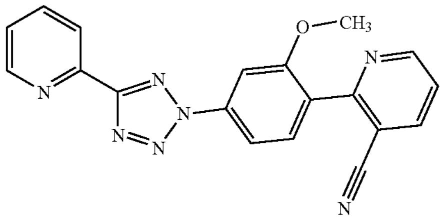 | 8.86-8.92 (m, 2H), 8.39 (d, 1H), 7.91-8.08 (m, 4H), 7.69 (d, 1H), 7.43-7.51 (m, 2H), 4.05 (s, 3H). | MS 356.4 (M⁺ + H). |
| 60. | 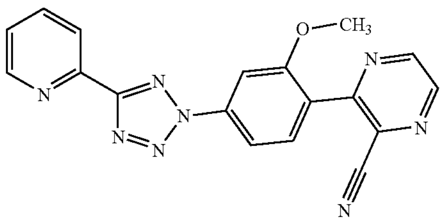 | 8.89 (m, 2H), 8.69 (d, 1H), 8.39 (d, 1H), 8.11 (d, 1H), 8.02 (d, 1H), 7.94 (dd, 1H), 7.73 (d, 1H), 7.48 (m, 1H), 4.08 (s, 3H). | MS 357.3 (M⁺ + H). |
| 61. | 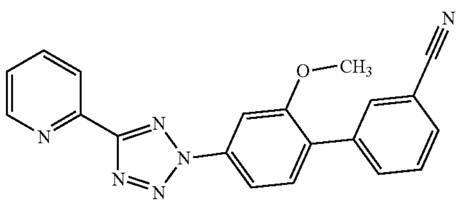 | 8.90 (d, 1H), 8.39 (d, 1H), 7.89-8.00 (m, 4H), 7.79 (d, 1H), 7.66 (d, 1H), 7.56 (m, 1H), 7.49 (m, 2H), 3.96 (s, 3H). | MS 355.3 (M⁺ + H). |
| 62. | 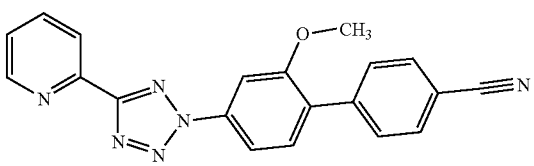 | 8.88 (d, 1H), 8.38 (d, 1H), 8.00 (d, 1H), 7.92 (m, 2H), 7.73 (d, 2H), 7.69 (d, 2H), 7.49 (m, 2H), 3.98 (s, 3H). | MS 355.3 (M⁺ + H). |
| 63. | 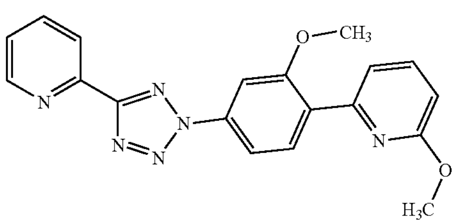 | 9.02 (d, 1H), 8.37 (d, 1H), 8.21 (d, 1H), 7.99 (d, 1H), 7.91 (m, 2H), 7.63 (m, 2H), 7.46 (m, 1H), 6.72 (m, 1H), 4.04 (s, 3H), 4.03 (s, 3H). | MS 361.1 (M⁺ + H). |
| 64. | 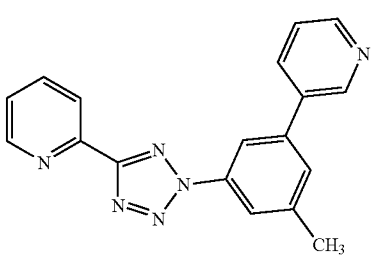 | 8.95 (d, 1H), 8.88 (d, 1H), 8.68 (m, 1H), 8.41 (d, 1H), 8.33 (s, 1H), 8.20 (s, 1H), 8.01 (m, 1H), 7.95 (m, 1H), 7.56 (s, 1H), 7.45 (m, 2H), 2.59 (s, 3H). | MS 315.4 (M⁺ + H). |
| 65. | 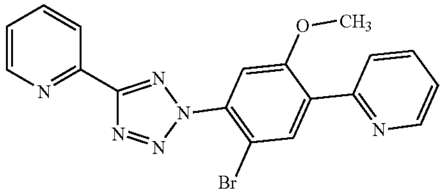 | 8.88 (d, 1H), 8.78 (d, 1H), 8.41 (d, 1H), 8.32 (s, 1H), 7.96 (m, 2H), 7.82 (m, 1H), 7.50 (m, 1H), 7.34 (m, 2H), 3.95 (s, 3H). | MS 411.0 (M⁺ + H + 2). |

-continued

| EXAMPLE | Structure | ¹H NMR | MS (ESI) |
|---|---|---|---|
| 66. | 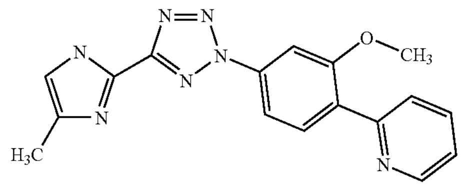 | 8.92-8.94 (m, 1H), 8.77-8.79 (m, 1H), 8.38-8.40 (m, 1H), 8.11-8.16 (m, 3H), 8.02-8.04 (m, 1H), 7.62 (s, 1H) | MS 334.3 (M⁺ + H). |
| 67. | 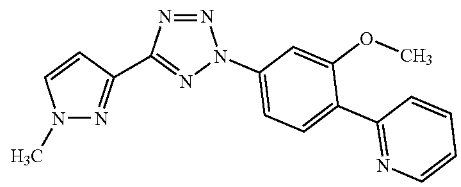 | 8.8 (d, 1H), 8.18-8.20 (m, 1H), 8.09-8.10 (m, 1H), 8.05 (d, 1H), 7.97 (d, 1H), 7.92 (m, 1H0, 7.90 (s, 1H) | MS 334.2 (M⁺ + H). |
| 68. | 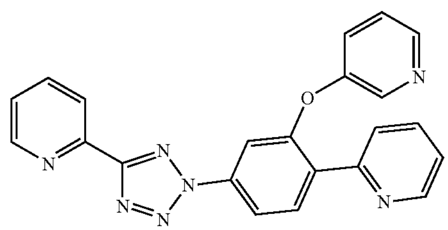 | 8.81-8.91 (m, 1H), 8.82-8.83 (m, 1H), 8.69-8.70 (d, 1H), 8.56-8.58 (m, 1H), 8.5-8.52 (d, 1H), 8.45-8.48 (dd, 1H), 8.22-8.4 (m, 3H), 8.29 (ddd, 1H), 8.20 (m, 1H), 7.88-8.03 (m, 2H), 7.78-7.80 (m, 1H) | MS 394.3 (M⁺ + H). |
| 69. | 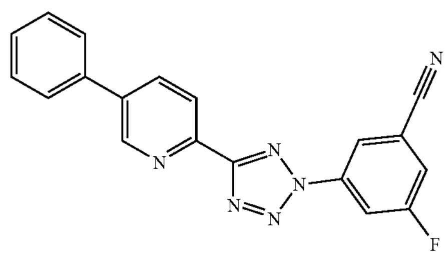 | 9.18 (m, 1H), 8.6 (s, 1H), 8.49 (ddd, 1H), 8.38 (m, 2H), 8.22 (m, 1H), 7.87 (m, 2H), 7.57 (m, 2H), 7.50 (m, 1H) | MS 343 (M⁺ + H). |
| 70. | 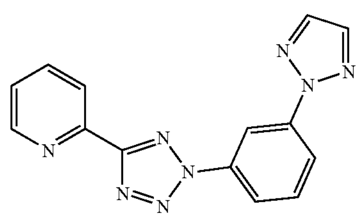 | 8.82-8.83 (m, 1H0, 8.79 (m, 1H), 8.25-8.34 (m, 5H), 8.08 (ddd, 1H), 7.92 (dd, 1H), 7.64 (dd, 1H) | MS 291 (M⁺ + H). |
| 71. | 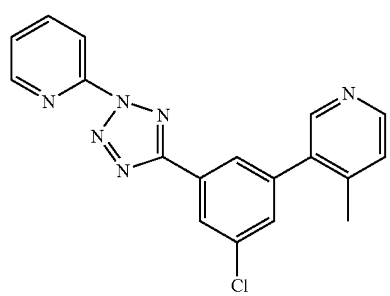 | 8.88 (s, 1H), 8.81-8.79 (d, 1H), 8.71-8.68 (m, 1H), 8.46-8.45 (m, 1H), 8.34-8.28 (m, 2H), 8.24-8.19 (m, 1H), 8.14-8.11 (d, 1H), 7.83-7.79 (m, 1H), 7.71-7.67 (m, 1H), 2.67 (s, 3H) | MS 349.1 (M⁺ + H). |

-continued

| EXAMPLE | Structure | ¹H NMR | MS (ESI) |
| --- | --- | --- | --- |
| 72. | 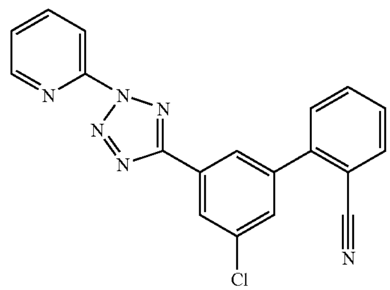 | 8.76-8.72 (m, 1H), 8.45-8.42 (m, 1H), 8.41-8.38 (m, 1H), 8.28-8.25 (d, 1H), 8.07-8.02 (m, 1H), 7.84-7.81 (m, 1H), 7.73-7.68 (m, 2H), 7.61-7.59 (d, 1H), 7.56-7.51 (m, 2H) | MS 359.0 (M⁺ + H). |
| 73. | 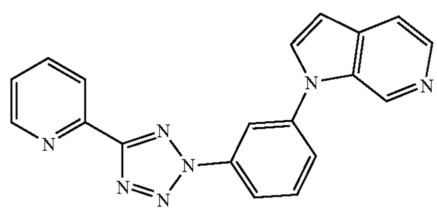 | 9.39 (s, 1H), 8.80-8.81 (d, 1H), 8.73-8.74 (d, 1H), 8.57 (s, 1H), 8.44-8.45 (d, 1H) 8.35-8.37 (d, 1H), 8.25-8.30 (m, 2H), 8.04-8.09 (m, 2H), 7.97-8.00 (dd, 1H), 7.61-7.63 (dd, 1H), 7.26 (d, 1H). | MS 340 (M⁺ + H) |
| 74. | 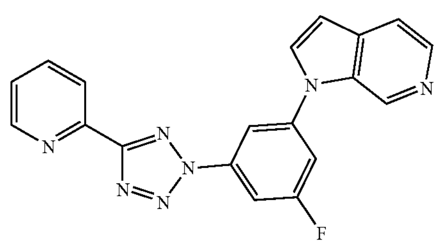 | 9.50 (s, 1H), 8.82-8.83 (m, 1H), 8.75-8.76 (d, 1H), 8.48 (m, 2H), 8.27-8.34 (m, 3H), 8.09-8.14 (m, 2H), 7.64-7.66 (dd, 1H), 7.29-7.30 (d, 1H). | MS 359 (M⁺ + H) |
| 75. | 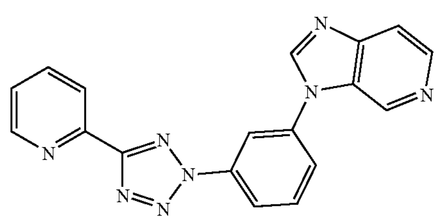 | ND | MS 341 (M⁺ + H) |
| 76. | 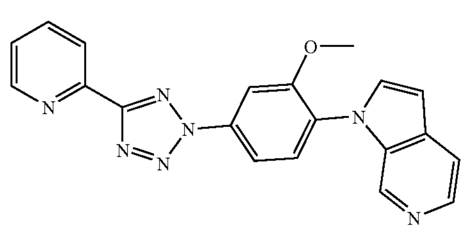 | ND | MS 370 (M⁺ + H) |
| 77. | 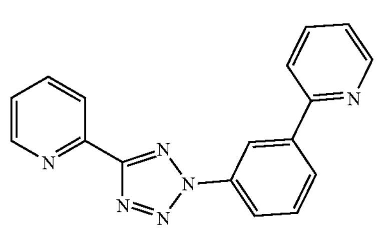 | 8.92-8.93 (m, 1H), 8.80-8.82 (m, 1H), 8.75-8.77 (m, 1H), 8.23-8.34 (m, 3H), 8.14-8.17 (m, 1H), 8.07 (ddd, 1H, J=10.0, 10.0, 2.4 Hz), 7.97 (ddd, 1H, J=10.4, 10.4, 2.4 Hz), 7.82 (dd, 1H, J=10.8, 10.8 Hz), 7.62 (ddd, 1H, J=10.0, 6.4, 1.2), 7.44-7.48 (m, 1H). | MS 301 (M⁺ + H) |

-continued

| EXAMPLE | Structure | ¹H NMR | MS (ESI) |
|---|---|---|---|
| 78. | 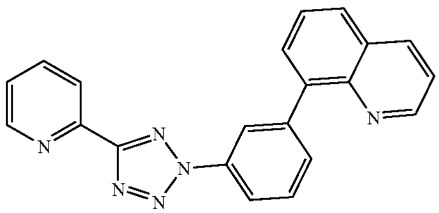 | 9.40-9.42 (d, 1H), 9.15-9.16 (d, 1H), 8.92-8.93 (m, 1H), 8.67-8.68 (d, 1H), 8.57-8.60 (m, 1H), 8.49-8.54 (m, 2H), 8.27-8.29 (d, 1H), 8.21-8.24 (dd, 1H), 8.15-8.18 (1H), 8.01-8.04 (t, 1H), 7.93-8.00 (m, 2H). | MS 351 (M⁺ + H) |
| 79. | 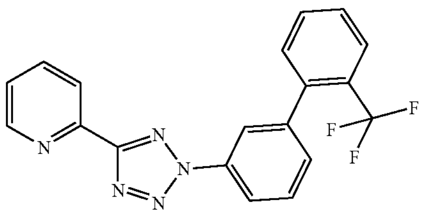 | 8.99 (m, 1H), 8.81-8.30 (d, 1H), 8.69-8.72 (m, 1H), 8.37-8.39 (dd, 1H), 8.27 (s 1H), 8.13-8.15 (m, 1H), 7.89-7.91 (d, 1H), 7.74-7.89 (m, 2H), 7.64-7.70 (m, 2H), 7.52-7.53 (d, 1H). | MS 368 (M⁺ + H) |
| 80. | 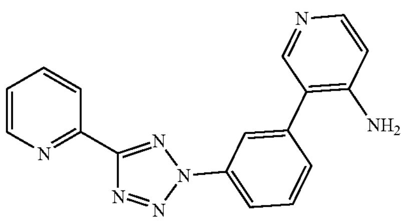 | 8.82-8.83 (d, 1H), 8.30-8.31 (d, 1H), 8.19-8.21 (m, 2H), 8.06-8.08 (m, 3H), 7.79-7.83 (m, 1H), 7.67-7.68 (d, 1H), 7.58-7.61 (m, 1H), 6.70-6.71 (d, 1H), 6.02 (s, 2H). | MS 316 (M⁺ + H) |
| 81. | 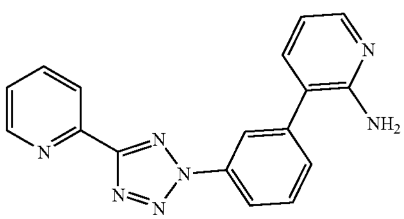 | 8.87-8.88 (m, 1H), 8.38-8.41 (m, 2H), 8.32-8.33 (m, 1H), 8.16-8.17 (dd, 1H), 7.93-7.95 (m, 1H), 7.68-7.71 (m, 2H), 7.47-7.50 (m, 1H), 6.82-6.85 (dd, 1H), 4.64 (s, 2H). | MS 316 (M⁺ + H) |
| 82. | 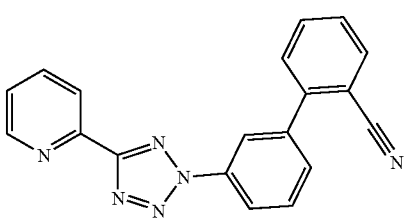 | 8.95-8.97 (m, 1H), 8.75-8.78 (m, 1H), 8.60-8.63 (m, 1H), 8.52 (m, 1H), 8.43 (m, 1H), 8.07 (m, 1H), 7.95-7.97 (d, 1H), 7.88-7.90 (m, 2H), 7.83-7.86 (m, 1H), 7.76-7.77 (d, 1H), 7.66-7.96 (dd, 1H). | MS 325 (M⁺ + H) |
| 83. | 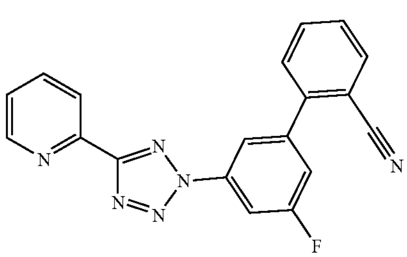 | 8.85-8.86 (d, 1H), 8.33-8.34 (d, 1H), 8.26-8.28 (m, 1H), 8.23-8.26 (m, 1H), 8.10-8.14 m, 1H), 8.08-8.10 (d, 1H), 7.85-7.92 (m, 3H), 7.74-7.76 (dd, 1H), 7.66-7.68 (m, 1H). | MS 344 (M⁺ + H) |

-continued
| EXAMPLE | Structure | ¹H NMR | MS (ESI) |
|---|---|---|---|
| 84. | 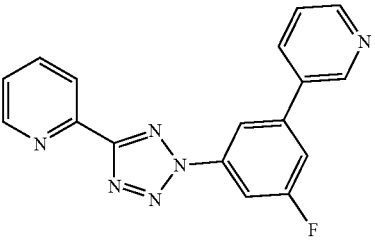 | 9.38 (s, 1H), 8.92-8.93 (d, 1H), 8.86-8.88 (m, 1H), 8.83-8.84 (d, 1H), 8.52 (s, 1H), 8.32-8.33 (d, 1H), 8.21-8.23 (m, 1H), 8.09-8.13 (m, 2H), 8.03-8.06 (m, 1H), 7.64-7.66 (m, 1H). | MS 319 (M⁺ + H) |
| 85. | 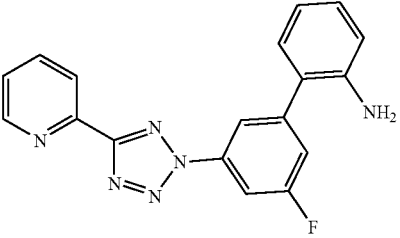 | 8.82-8.83 (m, 1H), 8.30-8.32 (d, 1H), 8.09-8.14 (m, 3H), 7.78-7.80 (d, 1H), 7.61-7.65 (m, 3H), 7.53-7.57 (m, 3H), 7.40-7.42 (m, 1H). | MS 333 (M⁺ + H) |
| 86. | 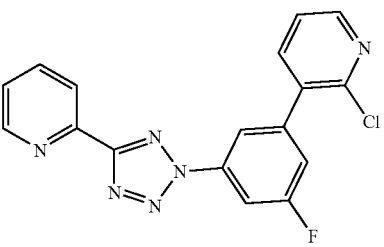 | 8.86-8.88 (m, 1H), 8.51-8.53 (dd, 1H). 8.38-8.39 (d, 1H), 8.22 (s, 1H), 8.12-8.14 (m, 1H), 7.92-7.96 (m, 1H), 7.78-7.81 (dd, 1H), 7.47-7.50 (m, 1H), 7.39-7.43 (m, 2H). | MS 354 (M⁺ + H) |
| 87. | 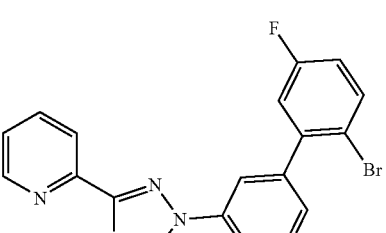 | 8.87-8.88 (d, 1H), 8.35-8.40 (m, 3H), 7.92-7.95 (m, 1H), 7.67-7.70 (m, 2H), 7.58-7.60 (d, 1H) 7.46-7.49 (dd, 1H), 7.16-7.19 (dd, 1H), 7.02-7.06 (m, 1H). | MS 396 (M⁺ + H) |
| 88. | 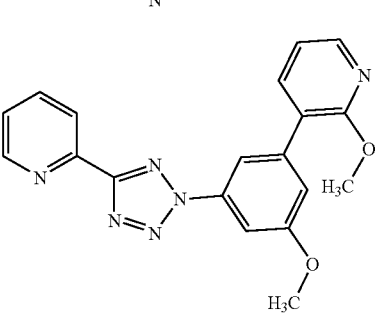 | 8.87-8.88 (m, 1H), 8.39-8.40 (d, 1H), 8.24-8.25 (d, 1H), 8.09 (s, 1H), 7.93-7.94 (m, 1H), 7.82-7.83 (m, 1H), 7.73-7.75 (dd, 1H), 7.44-7.48 (m, 1H), 7.30 (s, 1H), 7.03-7.05 (dd, 1H). | MS 361 (M⁺ + H) |
| 89. | 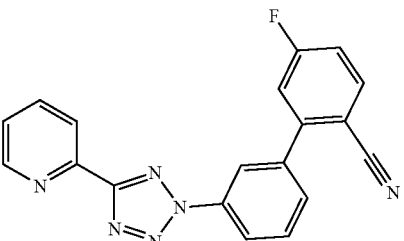 | 8.82-8.83 (m, 1H), 8.42 (s, 1H), 8.36-8.37 (m, 1H), 8.29-8.31 (m, 1H), 8.15-8.17 (m, 1H), 8.08-8.09 (m, 1H), 7.90-7.91 (m, 2H), 7.75-7.78 (m, 1H), 7.57-7.58 (m, 1H), 7.34-7.35 (m, 1H). | MS 343 (M⁺ + H) |

-continued

| EXAMPLE | Structure | ¹H NMR | MS (ESI) |
|---|---|---|---|
| 90. | 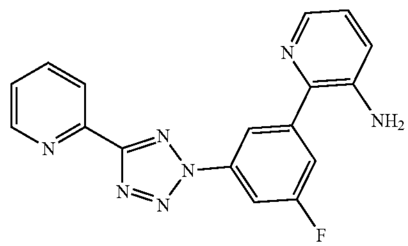 | 8.89-8.91 (m, 1H), 8.60-8.62 (m, 1H), 8.51 (s, 1H), 8.37-8.41 (m, 2H), 8.11-8.12 (d, 1H), 7.93-7.96 (d, 1H), 7.88-7.90 (m, 1H), 7.80-7.83 (m, 2H). | MS 334 (M⁺ + H) |
| 91. | 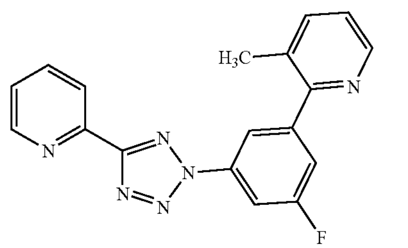 | 8.82-8.83 (d, 1H), 8.72-8.73 (d, 1H), 8.33 (s, 1H), 8.30-8.32 (d, 1H), 8.24-8.26 (d, 1H), 8.21-8.23 (d, 1H), 8.08-8.11 (m, 1H), 7.86-7.88 (d, 1H), 7.73-7.76 (dd, 1H), 7.63-7.65 (dd, 1H), 2.51 (s, 3H). | MS 333 (M⁺ + H) |
| 92. | 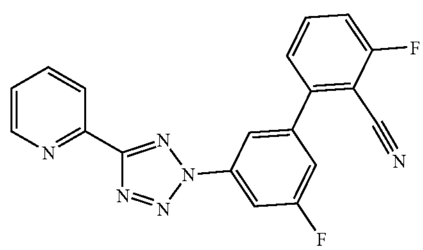 | 8.92-8.93 (d, 1H), 8.62-8.64 (d, 1H), 8.39-8.43 (m, 2H), 7.89-7.96 (m, 2H), 7.77-7.79 (m, 1H), 7.65-7.67 (d, 1H), 7.56-7.60 (m, 1H). | MS 361 (M⁺ + H) |
| 93. | 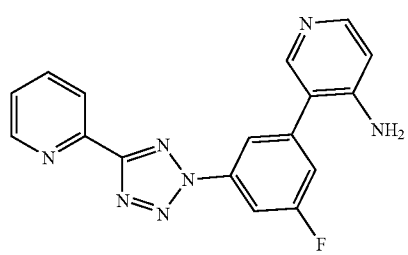 | 13.84 (m, 1H), 8.82-8.83 (d, 1H), 8.30-8.31 (d, 1H), 8.19-8.21 (d, 1H), 8.17 (s, 1H), 8.12-8.14 (d, 1H), 8.08-8.10 (m, 1H), 8.04-8.06 (m, 2H), 7.69-7.71 (d, 1H), 7.63-7.65 (m, 1H), 7.04-7.07 (dd, 1H). | MS 334 (M⁺ + H) |
| 94. | 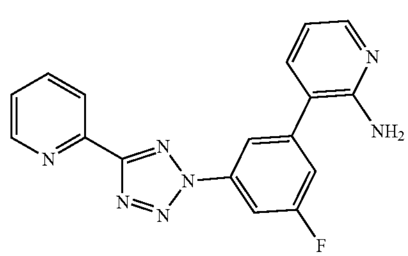 | 13.84 (m, 1H), 8.82 (s, 1H), 8.53 (m, 1H), 8.30-8.34 (m, 2H), 8.20-8.21 (m, 2H), 8.08-8.13 (m, 2H), 7.63-7.69 (m, 2H), 7.57 (m, 1H), 7.03-7.05 (d, 1H). | MS 334 (M⁺ + H) |
| 95. | 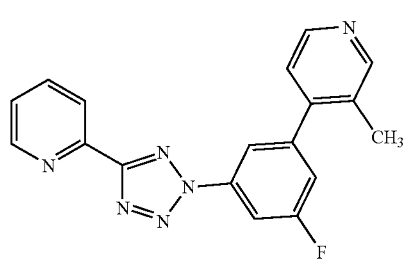 | 9.02 (s, 1H), 8.92-8.93 (d, 1H), 8.81-8.82 (d, 1H), 8.26-8.30 (m, 2H), 8.20 (m, 1H), 8.08-8.11 (m, 2H), 7.81-7.83 (dd, 1H), 7.63-7.65 (dd, 1H), 2.48 (s, 3H). | MS 333 (M⁺ + H) |

-continued

| EXAMPLE | Structure | ¹H NMR | MS (ESI) |
|---|---|---|---|
| 96. | 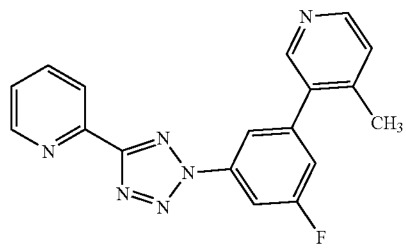 | 8.94 (s, 1H), 8.86-8.87 (d, 1H), 8.82-8.83 (d, 1H), 8.30-8.31 (d, 1H), 8.24-8.26 (m, 2H), 8.08-8.11 (m, 1H), 8.05-8.07 (d, 1H), 7.80-7.82 (m, 1H), 7.63-7.66 (dd, 1H), 2.58 (s, 3H). | MS 333 (M⁺ + H) |
| 97. | 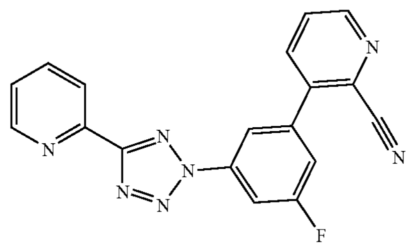 | 9.00-9.02 (m, 1H), 8.83-8.84 (m, 2H), 8.70-8.73 (m, 1H), 8.46 (s, 1H), 8.29-8.31 (d, 1H), 8.23-8.24 (m, 1H), 8.14-8.16 (m, 1H), 7.85-7.88 (dd, 1H), 7.79-7.81 (d, 1H), 7.64-7.68 (m, 1H), 7.56-7.59 (m, 1H). | MS 344 (M⁺ + H) |
| 98. | 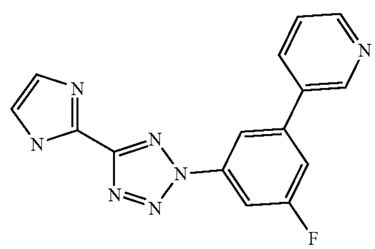 | 9.38 (s, 1H), 8.96-8.97 (d, 1H), 8.86-8.88 (d, 1H), 8.55 (s, 1H), 8.19-8.22 (m, 2H), 8.07-8.09 (dd, 1H), 7.86 (s, 2H). | MS 308 (M⁺ + H) |
| 99. | 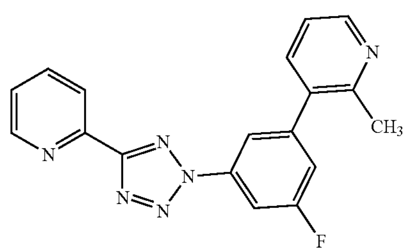 | 8.87-8.88 (d, 1H), 8.81-8.82 (d, 1H), 8.55-8.57 (d, 1H), 8.29-8.30 (d, 1H), 8.23-8.25 (m, 2H), 8.08-8.11 (m, 1H), 8.00-8.03 (m, 1H), 7.78-7.80 (d, 1H), 7.63-7.65 (dd, 1H), 2.77 (s, 3H). | MS 333 (M⁺ + H) |
| 100. | 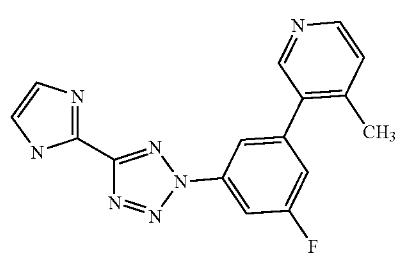 | 8.88 (s, 1H), 8.83-8.84 (d, 1H), 8.16-8.19 (m, 2H), 7.99-8.01 (d, 1H), 7.82-7.84 (d, 1H), 7.65 (s, 2H), 2.55 (s, 3H). | MS 322 (M⁺ + H) |
| 101. | 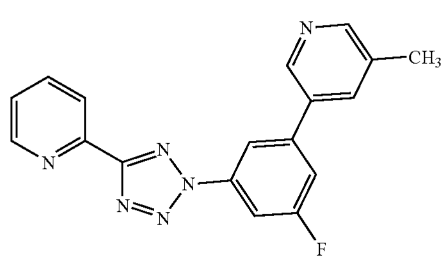 | 9.19-9.21 (m, 1H), 8.79-8.81 (m, 2H), 8.76 (s, 1H), 8.50 (m, 1H), 8.29-8.31 (d, 1H), 8.18-8.19 (d, 1H), 8.07-8.09 (m, 2H), 7.58-7.62 (m, 3H), 7.54-7.56 (m, 1H), 2.54 (s, 3H). | MS 333 (M⁺ + H) |

-continued

| EXAMPLE | Structure | ¹H NMR | MS (ESI) |
|---|---|---|---|
| 102. | 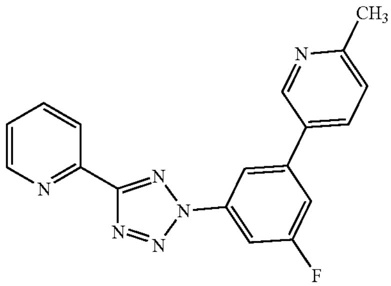 | 9.29 (s, 1H), 8.90-8.91 (d, 1H), 8.79-8.81 (m, 1H), 8.51 (s, 1H), 8.29-8.31 (d, 1H), 8.18-8.20 (, d, 1H), 8.09-8.11 (m, 2H), 8.01-8.03 (d, 1H), 7.53-7.62 (m, 4H), 2.80 (s, 3H). | MS 333 (M⁺ + H) |
| 103. | 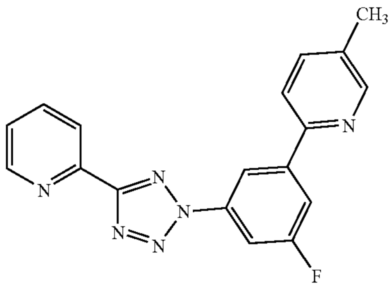 | 8.82-8.83 (d, 1H), 8.78 (s, 1H), 8.65 (m, 1H), 8.31-8.33 (d, 1H), 8.19-8.22 (m, 2H), 8.08-8.14 (m, 2H), 7.92-7.94 (dd, 1H), 7.60-7.66 (m, 1H). | MS 333 (M⁺ + H) |
| 104. | 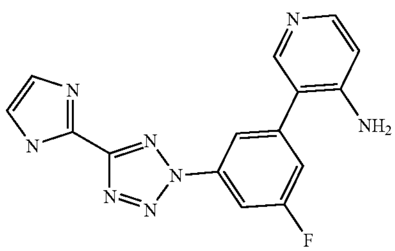 | 9.41-9.42 (d, 1H), 8.71 (d, 1H), 8.36 (s, 2H), 8.24 (s, 2H), 7.87 (s, 1H), 7.09-7.10 (d, 1H). | MS 323 (M⁺ + H) |
| 105. | 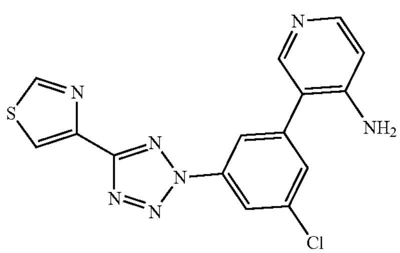 | 8.34 (s, 1H), 8.24-8.26 (d, 1H), 8.17-8.19 (d, 1H), 8.14 (s, 1H), 7.85 (s, 2H), 7.75-7.76 (m, 1H), 7.65 (s, 1H), 7.18-7.20 (d, 1H). | MS 356 (M⁺ + H) |
| 106. | 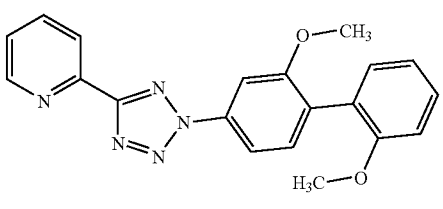 | 8.92-8.97 (m, 1H), 8.79-8.80 (d, 1H), 8.64-8.67 (dd, 1H), 8.09-8.11 (m, 1H), 7.90-7.92 (m, 2H), 7.47-7.49 (d, 1H), 7.38-7.41 (m, 1H), 7.23-7.25 (m, 1H), 7.09-7.10 (d, 1H), 7.02-7.05 (m, 1H), 3.94 (s, 3H), 3.80 (s, 3H). | MS 360 (M⁺ + H) |
| 107. | 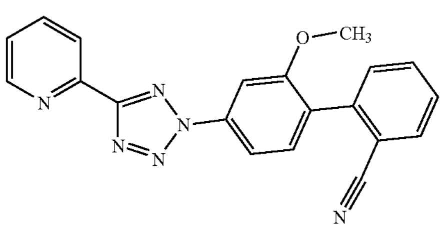 | 8.98-9.00 (m, 1H), 8.72-8.74 (d, 1H), 8.53-8.56 (m, 1H), 7.98-8.05 (m, 3H), 7.86-7.87 (d, 1H), 7.78-7.82 (m, 1H), 7.56-7.63 (m, 3H), 4.03 (s, 3H). | MS 355 (M⁺ + H) |

-continued

| EXAMPLE | Structure | ¹H NMR | MS (ESI) |
|---|---|---|---|
| 108. | 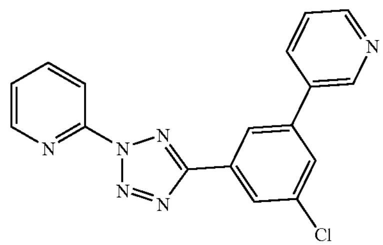 | ND | MS 335.2 (M⁺ + H). |
| 109. | 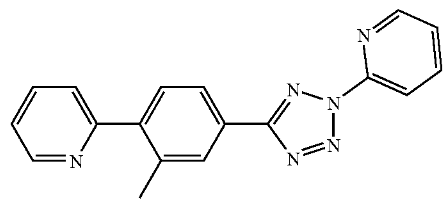 | 8.73-8.71 (m, 2H), 8.31-8.2 (m, 3H), 8.0 (dt, 1H), 7.78 (dt, 1H), 7.58 (d, 1H), 7.5-7.43 (m, 2H), 7.3-7.27 (m, 1H), 2.5 (s, 3H). | MS 315.4 (M⁺ + H). |
| 110. | 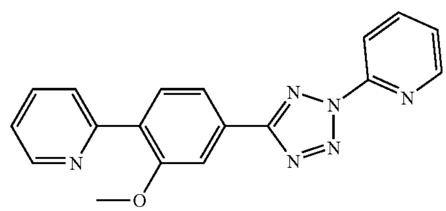 | 8.7 (br s, 2H), 8.28 (d, 1H), 8.10-8.0 (m, 2H), 7.9-7.8 (m, 2H), 7.8 (d, 1H), 7.75 (t, 1H), 7.52-7.48 (m, 1H), 7.3-7.2 (m, 1H), 4.1 (s, 3H). | MS 331.3 (M⁺ + H). |
| 111. | 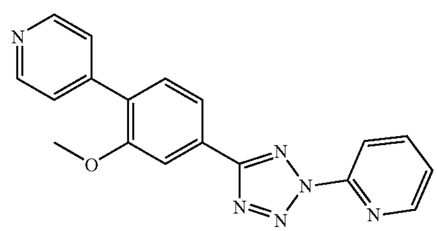 | ND | MS 331.8 (M⁺ + H). |
| 112. | 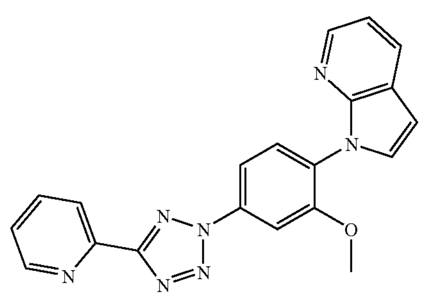 | 9.14-9.13 (d, 1H) 8.79-8.76 (d, 1H), 8.56-8.52 (m, 3H), 8.34-8.33 (d, 1H), 8.22-8.20 (d, 1H), 8.04-8.01 (t, 1H), 7.69-7.68 (d, 1H) 7.60-7.57 (m, 2H), 7.02-7.01 (d, 1H), 4.14 (s, 3H). | MS 370.1 (M⁺ + H). |
| 113. | 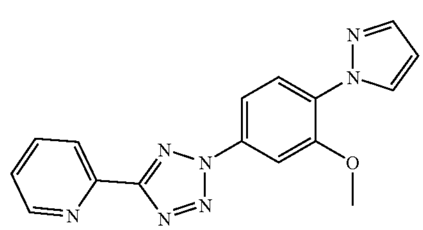 | 9.00-8.99 (d, 1H), 8.84-8.83 (d, 1H), 8.75-8.72 (t, 1H), 8.28-8.27 (d, 1H), 8.17-8.15 9t, 1H), 8.09 (s, 1H), 8.02-7.96 (m, 2H), 7.79 (s, 1H), 6.57-6.56 (t, 1H), 4.10 (s, 3H). | MS 320.3 (M⁺ + H). |
| 114. | 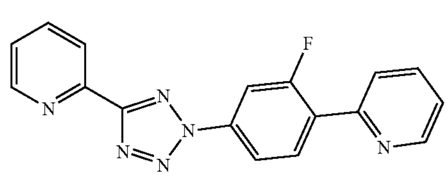 | 9.04--9.07 (m, 2H), 8.82-8.87 (m, 2H), 8.74-8.77 (m, 1H), 8.45-8.48 (m, 3H), 8.17-8.26 (m, 3H). | MS 319.9 (M⁺ + H) |

| EXAMPLE | Structure | ¹H NMR | MS (ESI) |
|---|---|---|---|
| 115. | 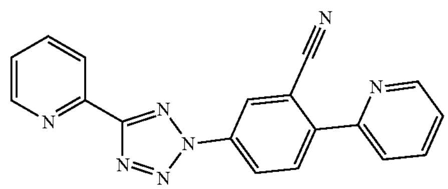 | 8.81-8.83 (m, 2H), 8.73-8.74 (d, 1H), 8.58-8.61 (dd, J=6, 6, 1H), 8.31-8.33, J=6, 1H), 8.23-8.25 (d, J=6.1H), 8.07-8.09 (m, 2H), 8.02-8.00 (d, J=6, 1H), 7.63-7.65 (t, 1H), 7.57-7.59 (t, 1H). | MS 326.2 (M⁺ + H) |
| 116. | 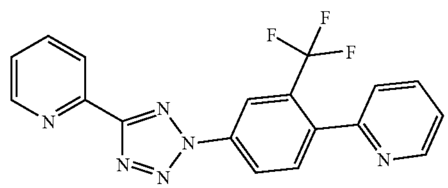 | 8.85 (s, 1H), 8.76-8.77 (d, J=3, 1H), 8.56-8.60 (m, 2H), 8.33-8.35 (d, J=6, 1H), 8.05-8.12 (m, 2H), 7.94-7.96 (d, J=6, 1H), 7.69-7.71 (d, J=6, 1H), 7.64-7.66 (m, 1H), 7.58-7.60 (m, 1H). | MS 369.2 (M⁺ + H) |
| 117. | 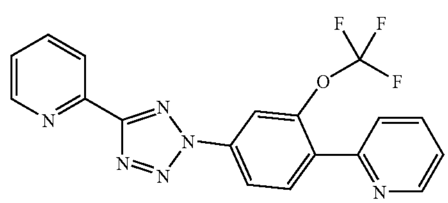 | 8.86-8.87 (d, J=3, 1H), 8.77-8.78 (d, J=3, 1H), 8.38-8.40 (d, J=6, 1H), 8.34 (s, 1H), 8.12-8.14 (d, J=6, 1H), 7.92-7.94 (t, 1H), 7.81-7.84 (m, 1H), 7.77-7.79 (d, J=6, 1H), 7.48-7.50 (t, 1H), 7.35-7.37 (t, 1H). | MS 385.1 (M⁺ + H) |
| 118. | 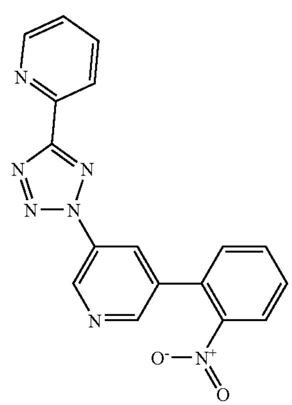 | ND | MS 346 (M + H) |
| 119. | 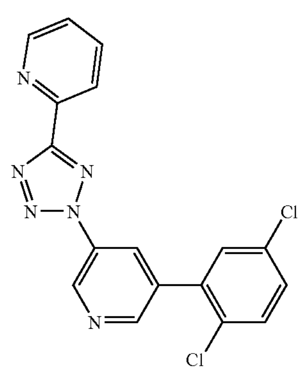 | ND | MS 370 (M + H) |

-continued
| EXAMPLE | Structure | ¹H NMR | MS (ESI) |
|---|---|---|---|
| 120. | 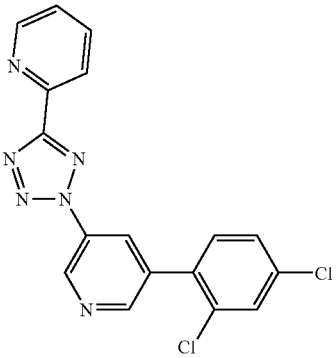 | ND | MS 370 (M + H) |
| 121. | 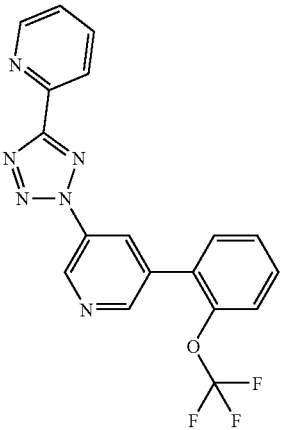 | ND | MS 385 (M + H) |
| 122. | 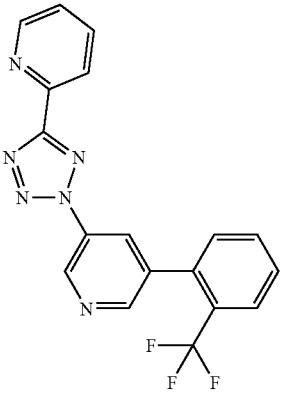 | ND | MS 369 (M + H) |
| 123. | 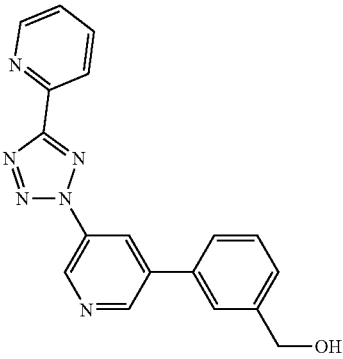 | ND | MS 331 (M + H) |

-continued

| EXAMPLE | Structure | ¹H NMR | MS (ESI) |
|---|---|---|---|
| 124. | 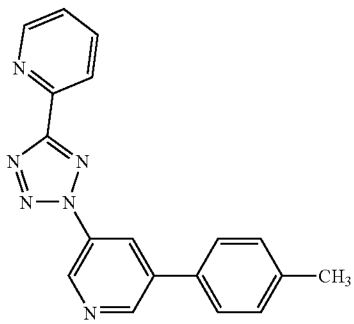 | ND | MS 315 (M + H) |
| 125. | 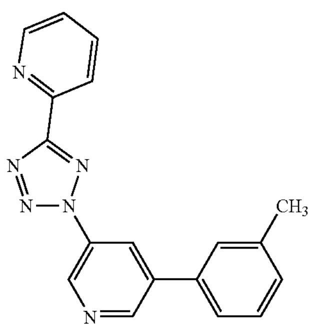 | ND | MS 315 (M + H) |
| 126. | 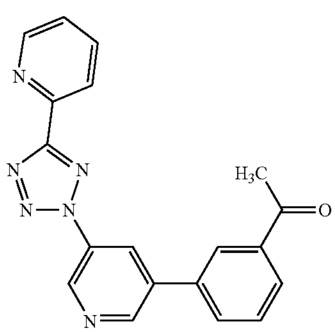 | ND | MS 343 (M + H) |
| 127. | 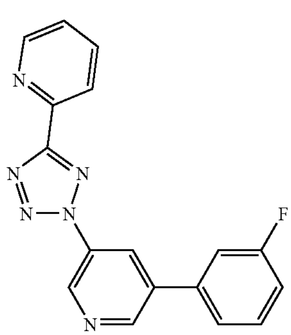 | ND | MS 319 (M + H) |

-continued
| EXAMPLE | Structure | ¹H NMR | MS (ESI) |
|---|---|---|---|
| 128. | 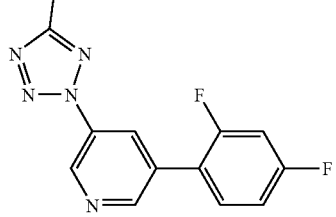 | ND | MS 337 (M + H) |
| 129. | 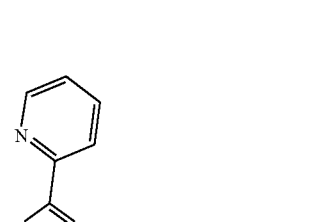 | ND | MS 316 (M + H) |
| 130. | 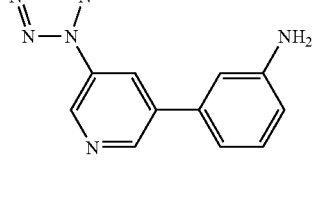 | ND | MS 317 (M + H) |
| 131. | 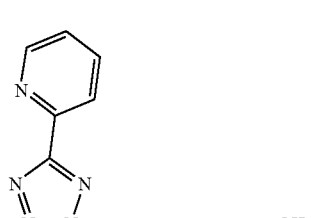 | ND | MS 319 (M + H) |

-continued

| EXAMPLE | Structure | ¹H NMR | MS (ESI) |
|---|---|---|---|
| 132. | 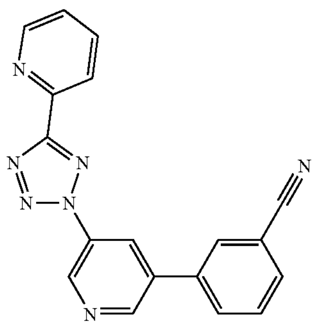 | ND | MS 326 (M + H) |
| 133. | 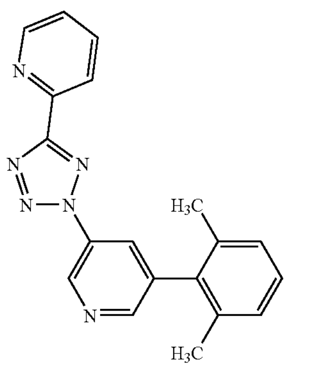 | ND | MS 329 (M + H) |
| 134. | 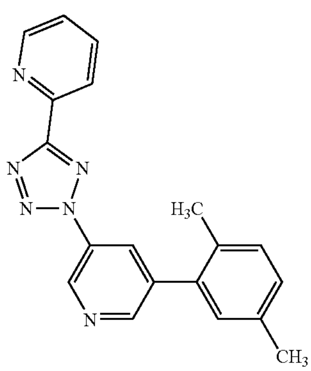 | ND | MS 329 (M + H) |
| 135. | 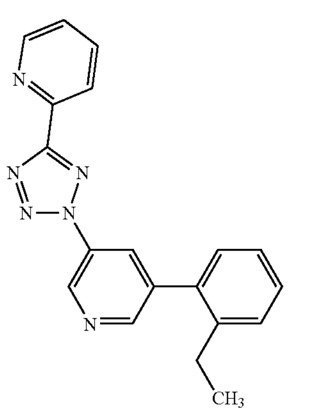 | ND | MS 329 (M + H) |

-continued

| EXAMPLE | Structure | ¹H NMR | MS (ESI) |
|---|---|---|---|
| 136. | 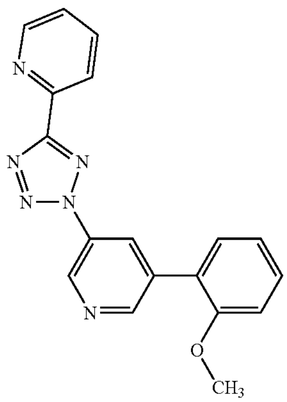 | ND | MS 331 (M + H) |
| 137. | 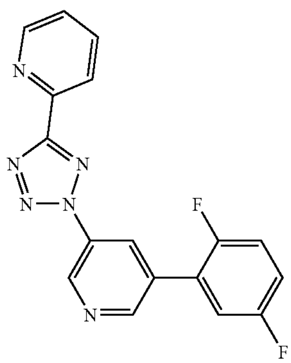 | ND | MS 337 (M + H) |
| 138. | 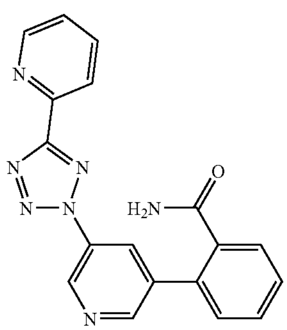 | ND | MS 344 (M + H) |
| 139. | 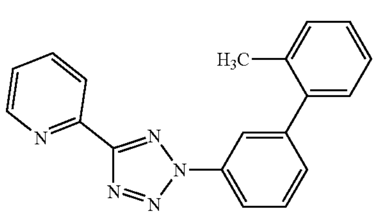 | ND | MS 314 (M⁺ + H) |
| 140. | 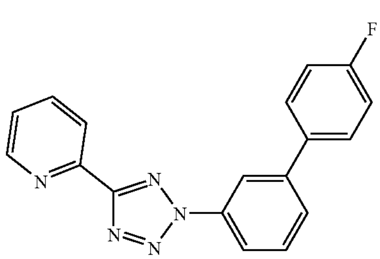 | ND | MS 318 (M⁺ + H) |

-continued

| EXAMPLE | Structure | ¹H NMR | MS (ESI) |
|---|---|---|---|
| 141. | 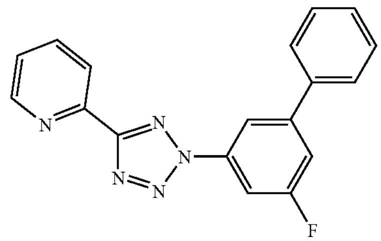 | ND | MS 318 (M⁺ + H) |
| 142. | 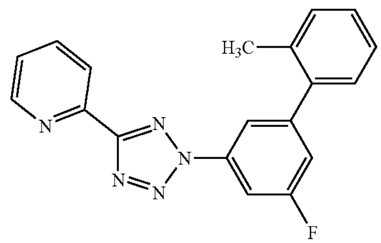 | ND | MS 332 (M⁺ + H) |
| 143. | 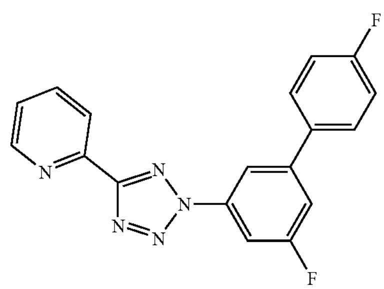 | ND | MS 336 (M⁺ + H) |
| 144. | 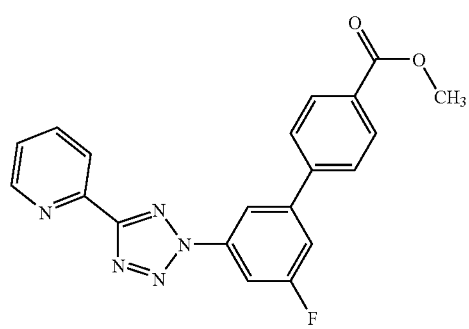 | ND | MS 376 (M⁺ + H) |
| 145. | 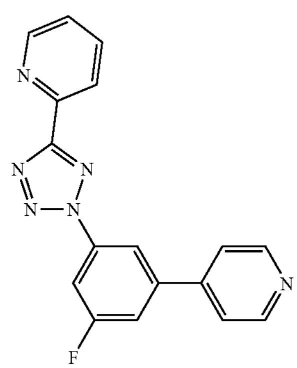 | ND | MS 319 (M⁺ + H) |

| EXAMPLE | Structure | $^1$H NMR | MS (ESI) |
|---|---|---|---|
| 146. | 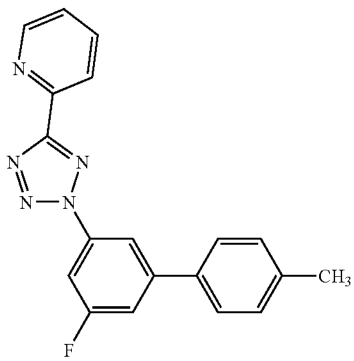 | ND | MS 332 (M$^+$ + H) |
| 147. | 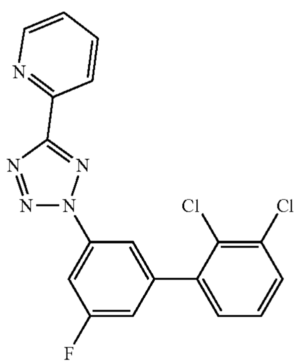 | ND | MS 387 (M$^+$ + H) |
| 148. | 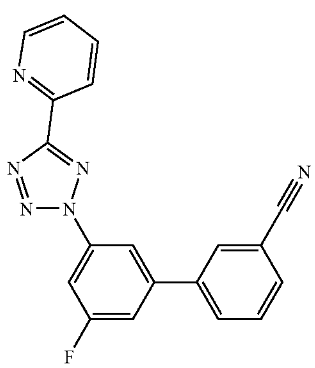 | ND | MS 343 (M$^+$ + H) |
| 149. | 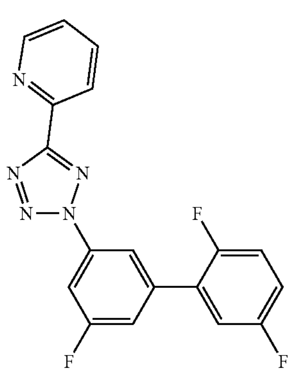 | ND | MS 354 (M$^+$ + H) |

-continued

| EXAMPLE | Structure | ¹H NMR | MS (ESI) |
|---|---|---|---|
| 150. | 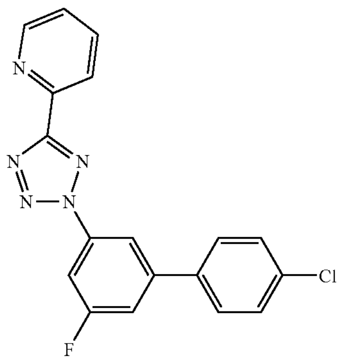 | ND | MS 352 (M⁺ + H) |
| 151. | 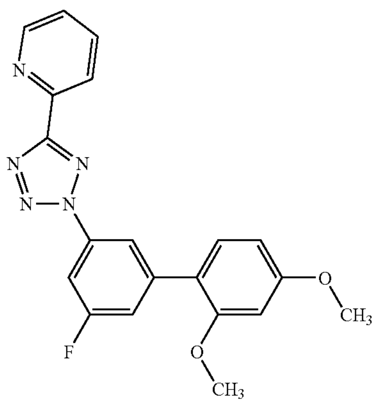 | ND | MS 378 (M⁺ + H) |
| 152. | 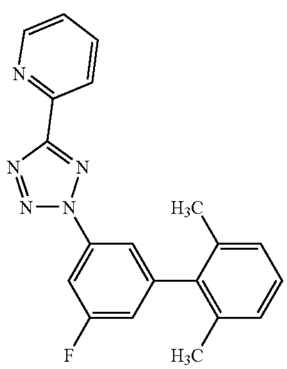 | ND | MS 346 (M⁺ + H) |
| 153. | 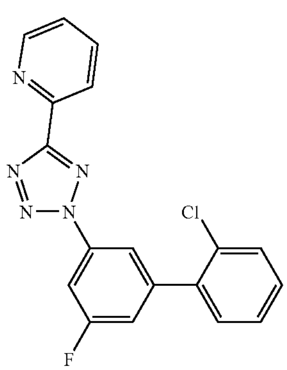 | ND | MS 352 (M⁺ + H) |

-continued

| EXAMPLE | Structure | ¹H NMR | MS (ESI) |
|---|---|---|---|
| 154. | 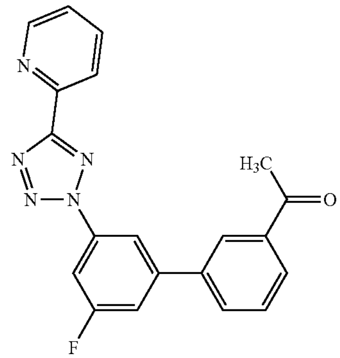 | ND | MS 360 (M⁺ + H) |
| 155. | 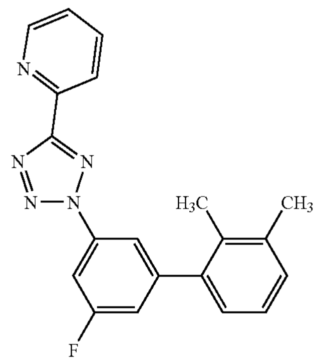 | ND | MS 346 (M⁺ + H) |
| 156. | 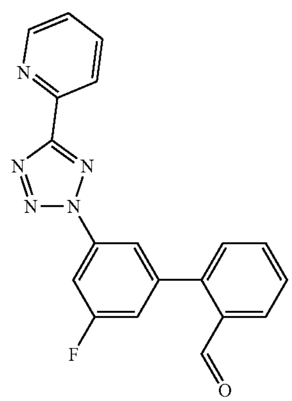 | ND | MS 346 (M⁺ + H) |
| 157. | 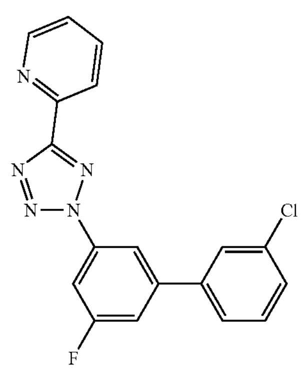 | ND | MS 352 (M⁺ + H) |

-continued

| EXAMPLE | Structure | ¹H NMR | MS (ESI) |
|---|---|---|---|
| 158. | 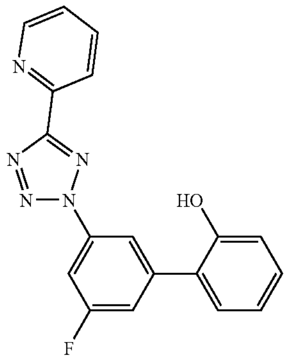 | ND | MS 334 (M⁺ + H) |
| 159. | 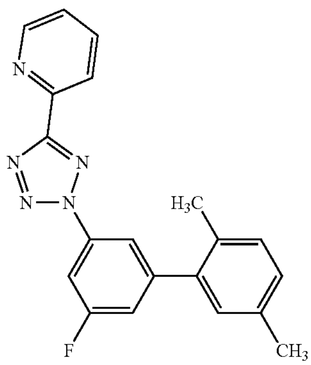 | ND | MS 346 (M⁺ + H) |
| 160. | 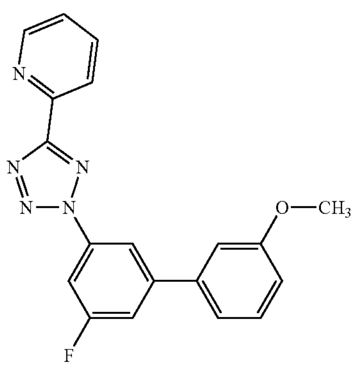 | ND | MS 348 (M⁺ + H) |
| 161. | 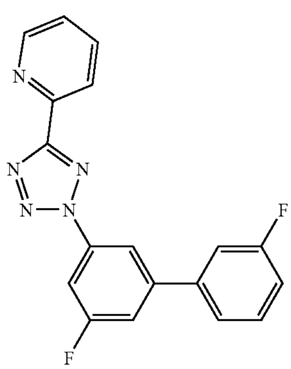 | ND | MS 336 (M⁺ + H) |

-continued

| EXAMPLE | Structure | ¹H NMR | MS (ESI) |
|---|---|---|---|
| 162. | 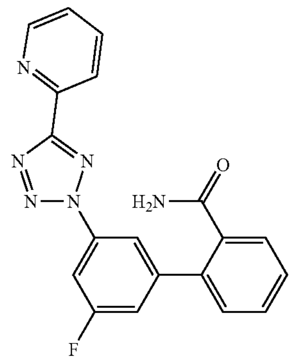 | ND | MS 361 (M⁺ + H) |
| 163. | 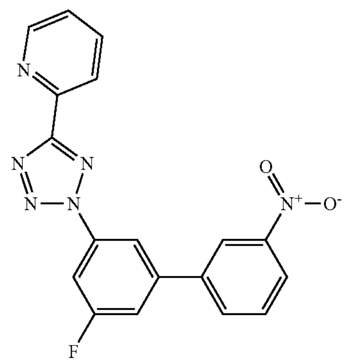 | ND | MS 363 (M⁺ + H) |
| 164. | 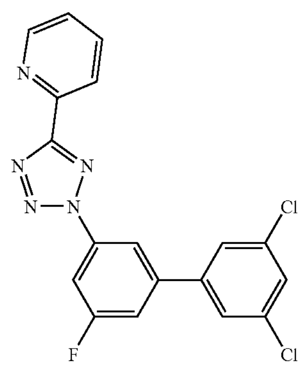 | ND | MS 387 (M⁺ + H) |
| 165. | 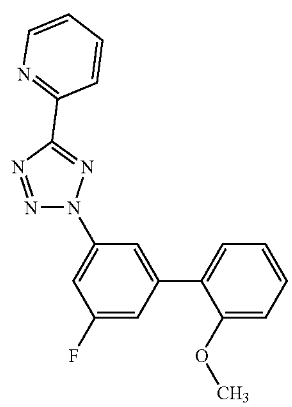 | ND | MS 348 (M⁺ + H) |

-continued
| EXAMPLE | Structure | ¹H NMR | MS (ESI) |
|---|---|---|---|
| 166. | 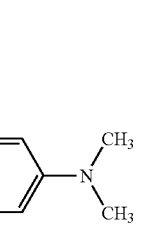 | ND | MS 361 (M⁺ + H) |
| 167. | 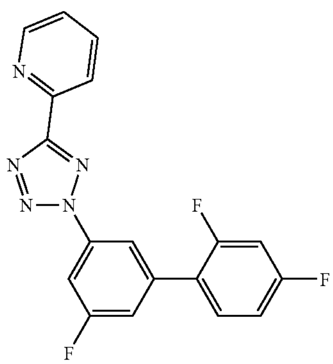 | ND | MS 354 (M⁺ + H) |
| 168. | 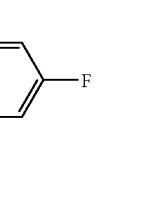 | ND | MS 336 (M⁺ + H) |
| 169. | 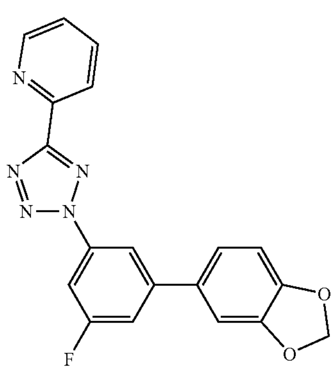 | ND | MS 362 (M⁺ + H) |

-continued

| EXAMPLE | Structure | ¹H NMR | MS (ESI) |
|---|---|---|---|
| 170. | 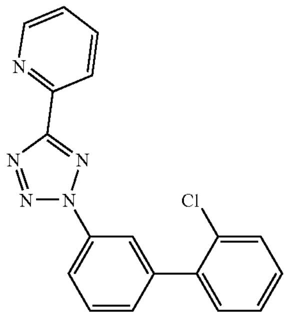 | ND | MS 334 (M⁺ + H) |
| 171. | 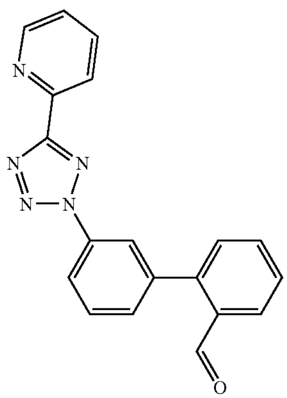 | ND | MS 328 (M⁺ + H) |
| 172. | 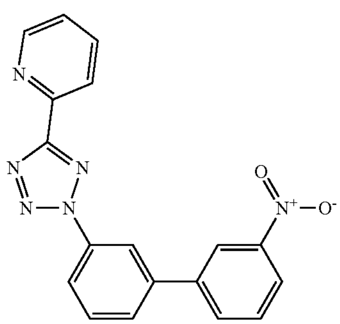 | ND | MS 345 (M⁺ + H) |
| 173. | 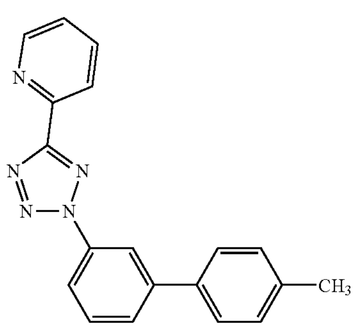 | ND | MS 314 (M⁺ + H) |

-continued
| EXAMPLE | Structure | $^1$H NMR | MS (ESI) |
|---|---|---|---|
| 174. | 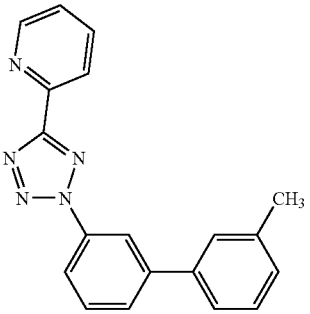 | ND | MS 314 (M$^+$ + H) |
| 175. | 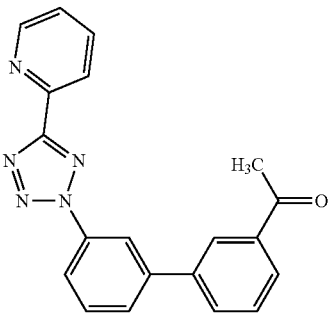 | ND | MS 342 (M$^+$ + H) |
| 176. | 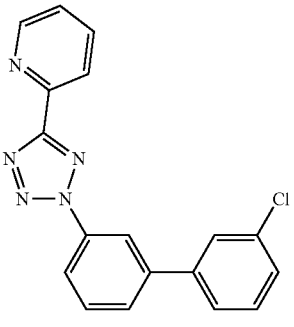 | ND | MS 334 (M$^+$ + H) |
| 177. | 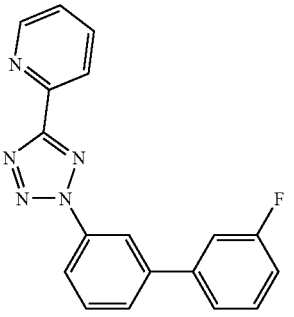 | ND | MS 318 (M$^+$ + H) |

-continued

| EXAMPLE | Structure | ¹H NMR | MS (ESI) |
|---|---|---|---|
| 178. | 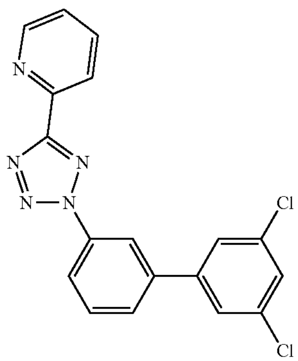 | ND | MS 369 (M⁺ + H) |
| 179. | 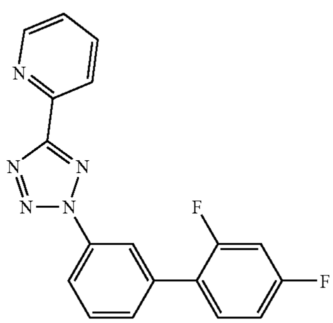 | ND | MS 336 (M⁺ + H) |
| 180. | 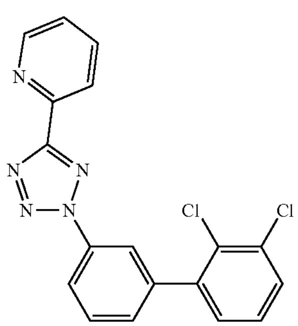 | ND | MS 369 (M⁺ + H) |
| 181. | 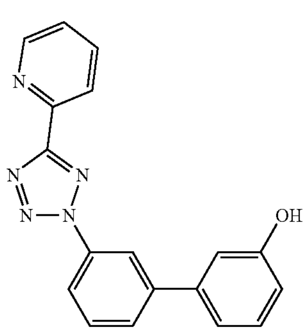 | ND | MS 316 (M⁺ + H) |

-continued

| EXAMPLE | Structure | ¹H NMR | MS (ESI) |
|---|---|---|---|
| 182. | 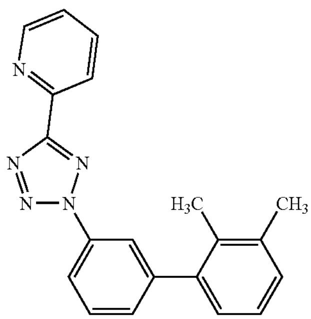 | ND | MS 328 (M⁺ + H) |
| 183. | 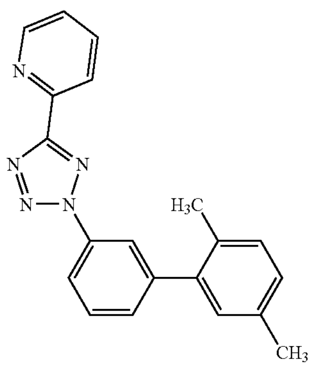 | ND | MS 328 (M⁺ + H) |
| 184. | 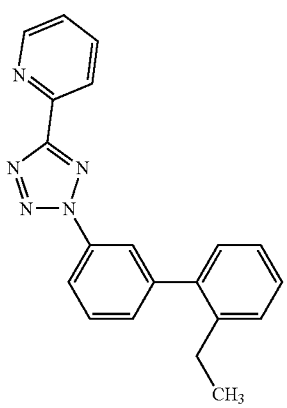 | ND | MS 328 (M⁺ + H) |
| 185. | 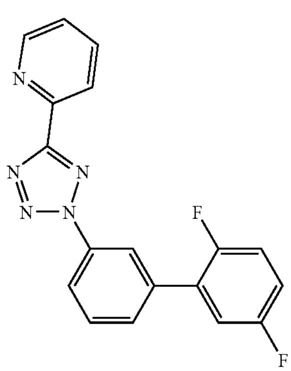 | ND | MS 336 (M⁺ + H) |

-continued

| EXAMPLE | Structure | ¹H NMR | MS (ESI) |
|---|---|---|---|
| 186. | 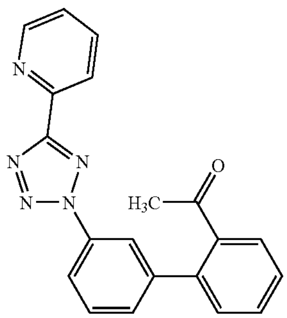 | ND | MS 342 (M⁺ + H) |
| 187. | 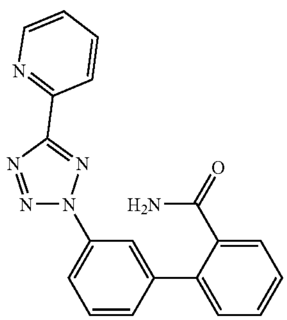 | ND | MS 343 (M⁺ + H) |
| 188. | 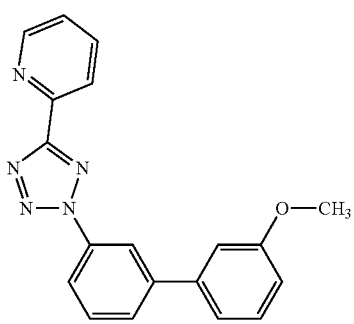 | ND | MS 330 (M⁺ + H) |
| 189. | 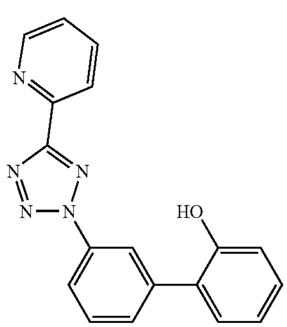 | ND | MS 316 (M⁺ + H) |

-continued

| EXAMPLE | Structure | ¹H NMR | MS (ESI) |
|---|---|---|---|
| 190. | 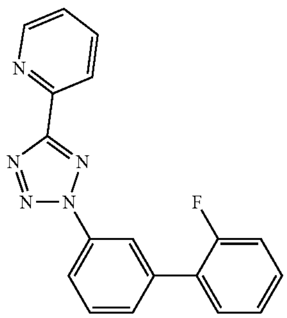 | ND | MS 318 (M⁺ + H) |
| 191. | 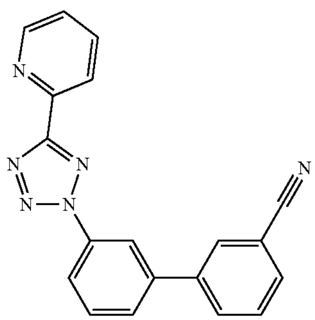 | ND | MS 325 (M⁺ + H) |
| 192. | 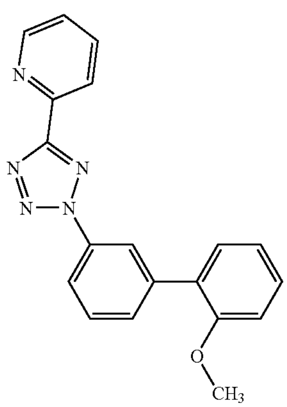 | ND | MS 330 (M⁺ + H) |
| 193. | 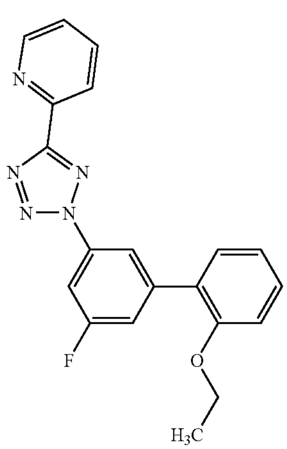 | ND | MS 362 (M⁺ + H) |

-continued

| EXAMPLE | Structure | ¹H NMR | MS (ESI) |
|---|---|---|---|
| 194. | 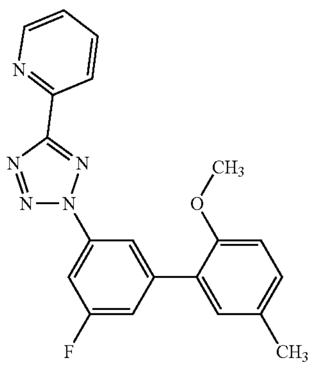 | ND | MS 362 (M⁺ + H) |
| 195. | 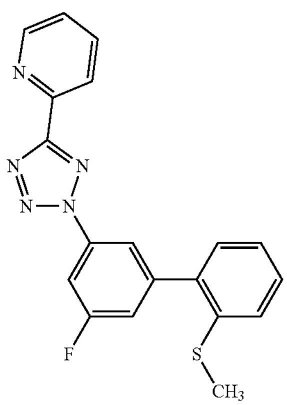 | ND | MS 364 (M⁺ + H) |
| 196. | 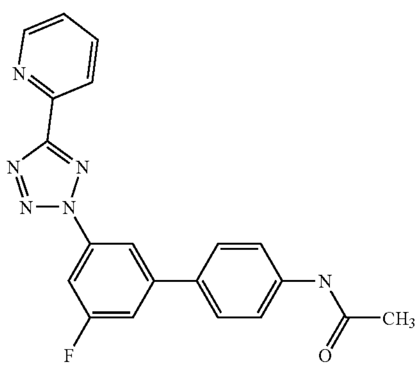 | ND | MS 375 (M⁺ + H) |
| 197. | 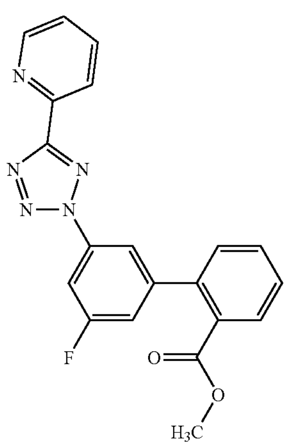 | ND | MS 376 (M⁺ + H) |

| EXAMPLE | Structure | ¹H NMR | MS (ESI) |
|---|---|---|---|
| 198. | 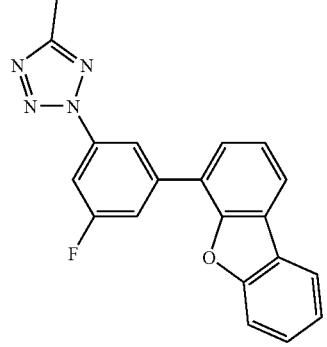 | ND | MS 408 (M⁺ + H) |
| 199. | 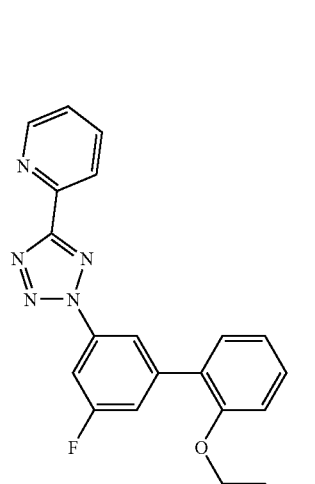 | ND | MS 410 (M⁺ + H) |
| 200. | 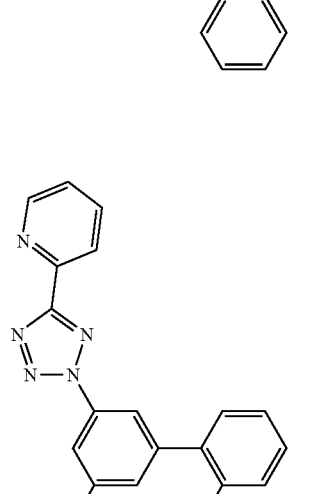 | ND | MS 386 (M⁺ + H) |

-continued

| EXAMPLE | Structure | ¹H NMR | MS (ESI) |
|---|---|---|---|
| 201. | 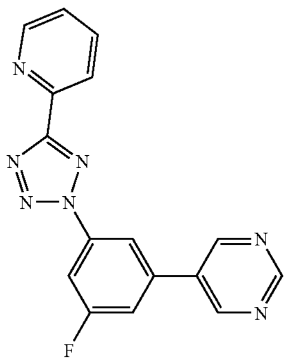 | ND | MS 320 (M⁺ + H) |
| 202. | 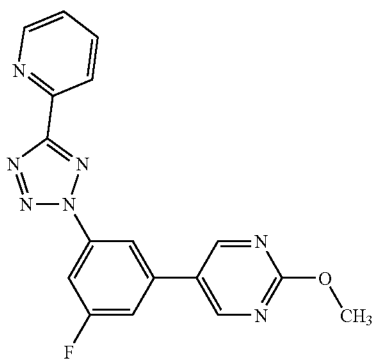 | ND | MS 350 (M⁺ + H) |
| 203. | 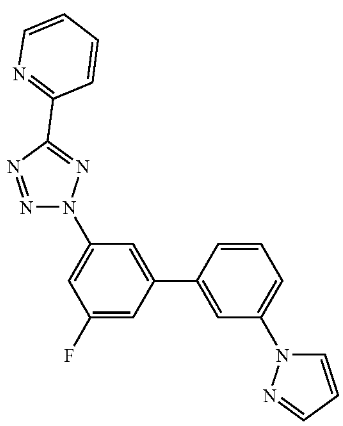 | ND | MS 384 (M⁺ + H) |
| 204. | 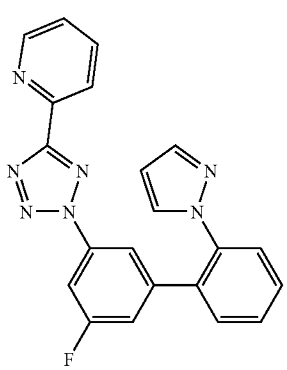 | ND | MS 384 (M⁺ + H) |

-continued

| EXAMPLE | Structure | ¹H NMR | MS (ESI) |
|---|---|---|---|
| 205. | 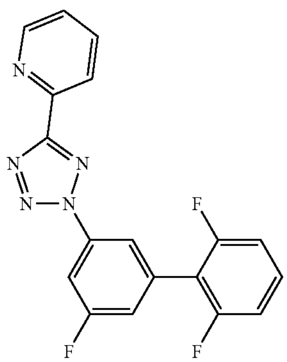 | ND | MS 354 (M⁺ + H) |
| 206. | 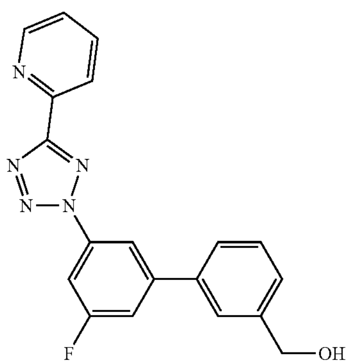 | ND | MS 348 (M⁺ + H) |
| 207. | 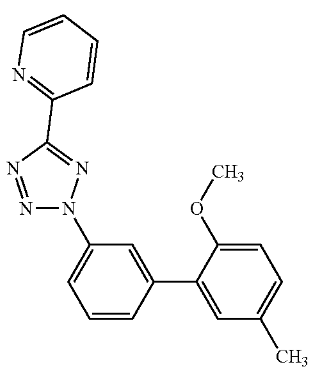 | ND | MS 344 (M⁺ + H) |
| 208. | 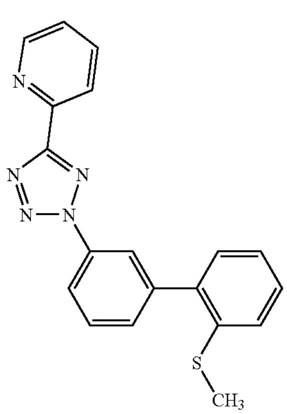 | ND | MS 346 (M⁺ + H) |

-continued

| EXAMPLE | Structure | $^1$H NMR | MS (ESI) |
| --- | --- | --- | --- |
| 209. | 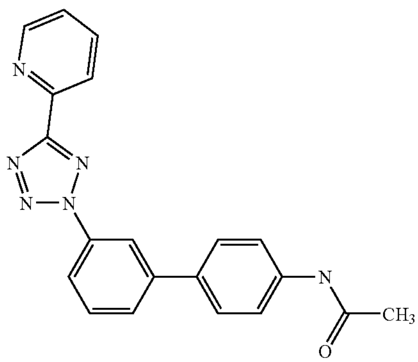 | ND | MS 357 (M$^+$ + H) |
| 210. | 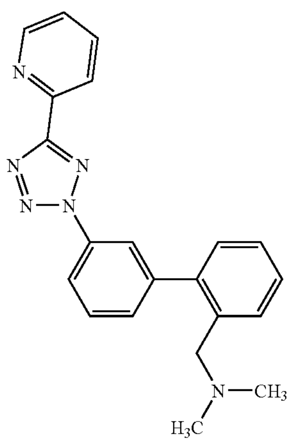 | ND | MS 357 (M$^+$ + H) |
| 211. | 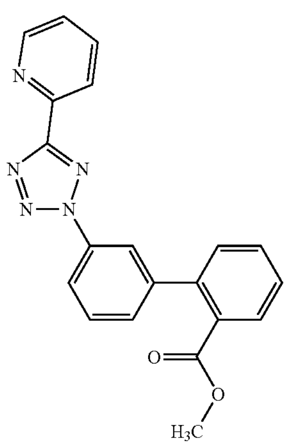 | ND | MS 358 (M$^+$ + H) |

-continued
| EXAMPLE | Structure | ¹H NMR | MS (ESI) |
|---|---|---|---|
| 212. | 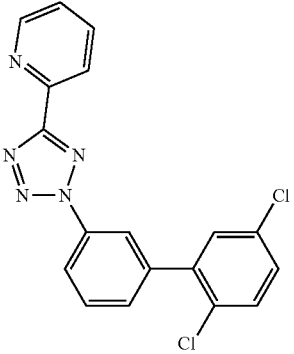 | ND | MS 369 (M⁺ + H) |
| 213. | 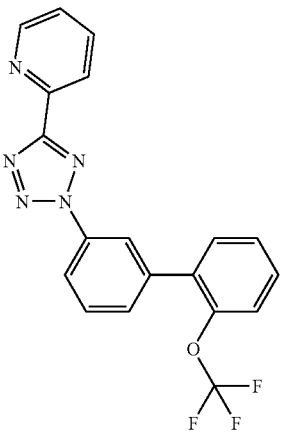 | ND | MS 384 (M⁺ + H) |
| 214. | 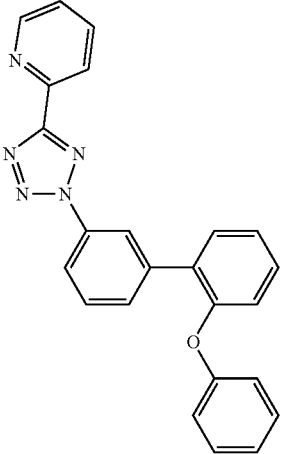 | ND | MS 392 (M⁺ + H) |

-continued

| EXAMPLE | Structure | ¹H NMR | MS (ESI) |
|---|---|---|---|
| 215. | 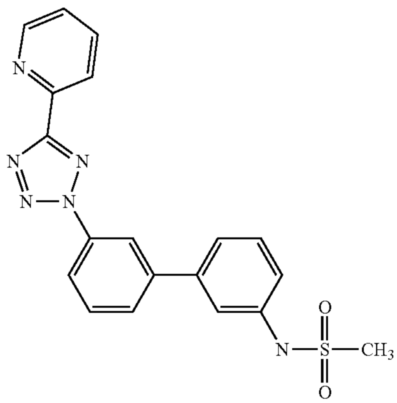 | ND | MS 393 (M⁺ + H) |
| 216. | 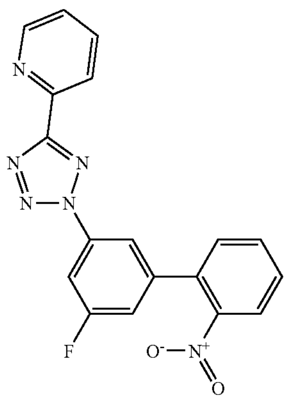 | ND | MS 363 (M⁺ + H) |
| 217. | 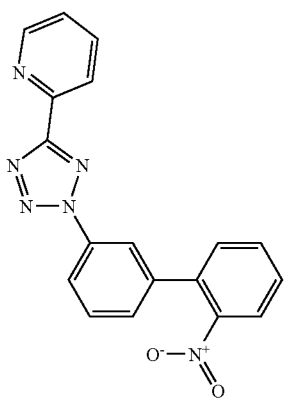 | ND | MS 345 (M⁺ + H) |
| 218. | 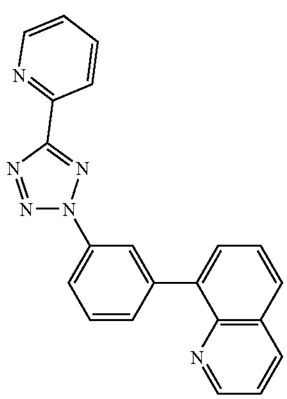 | ND | MS 351 (M⁺ + H) |

-continued

| EXAMPLE | Structure | ¹H NMR | MS (ESI) |
|---|---|---|---|
| 219. | 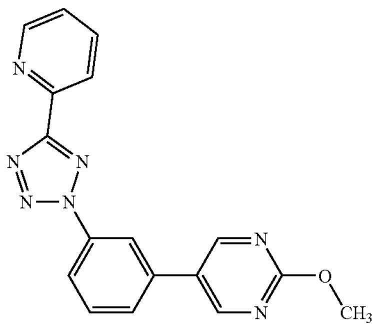 | ND | MS 332 (M⁺ + H) |
| 220. | 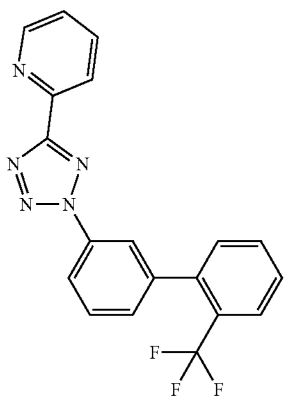 | ND | MS 368 (M⁺ + H) |
| 221. | 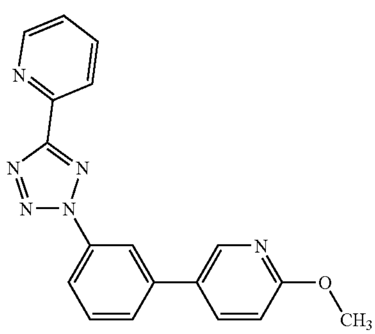 | ND | MS 331 (M⁺ + H) |
| 222. | 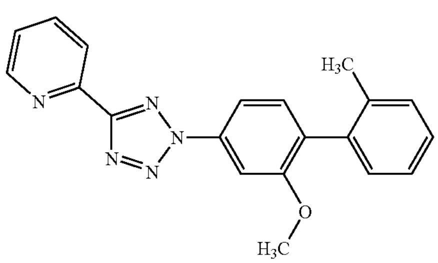 | ND | MS 344 (M⁺ + H) |

-continued

| EXAMPLE | Structure | ¹H NMR | MS (ESI) |
|---|---|---|---|
| 223. | 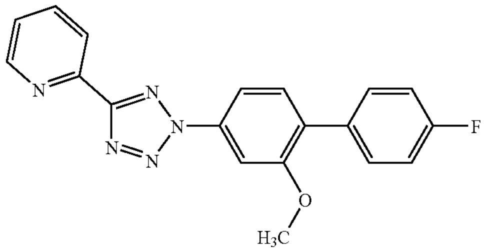 | ND | MS 348 (M⁺ + H) |
| 224. | 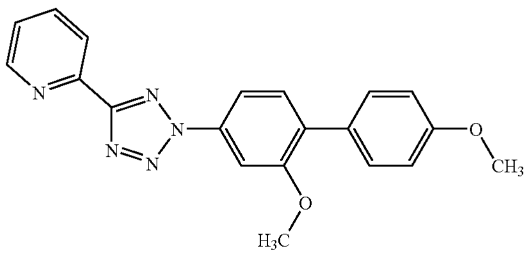 | ND | MS 360 (M⁺ + H) |
| 225. | 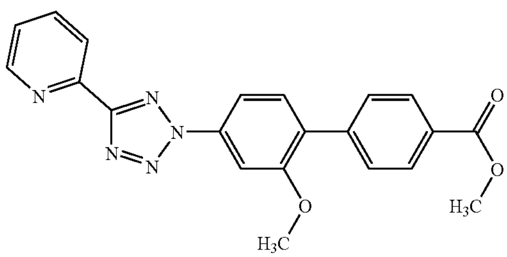 | ND | MS 388 (M⁺ + H) |
| 226. | 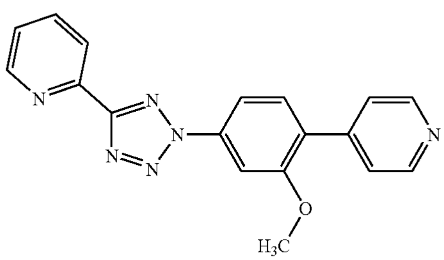 | ND | MS 331 (M⁺ + H) |
| 227. | 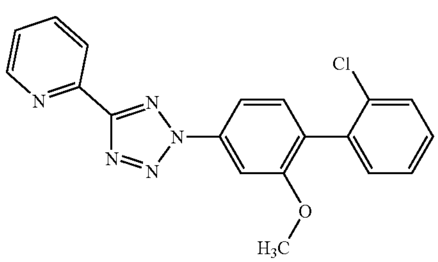 | ND | MS 364 (M⁺ + H) |
| 228. | 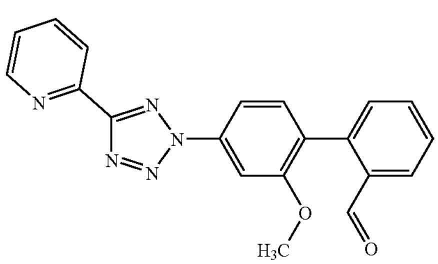 | ND | MS 358 (M⁺ + H) |

-continued
| EXAMPLE | Structure | ¹H NMR | MS (ESI) |
| --- | --- | --- | --- |
| 229. | 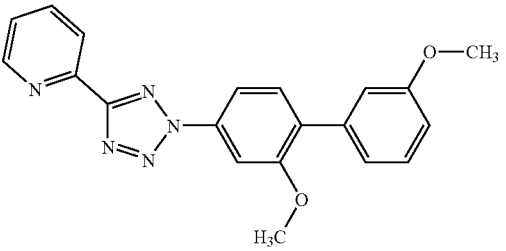 | ND | MS 360 (M⁺ + H) |
| 230. | 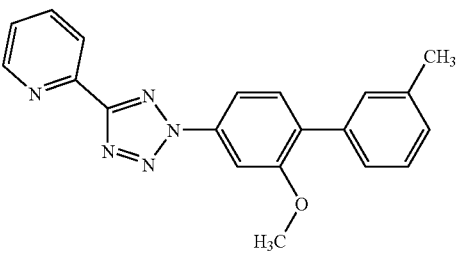 | ND | MS 344 (M⁺ + H) |
| 231. | 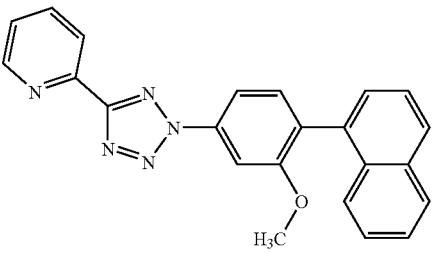 | ND | MS 380 (M⁺ + H) |
| 232. | 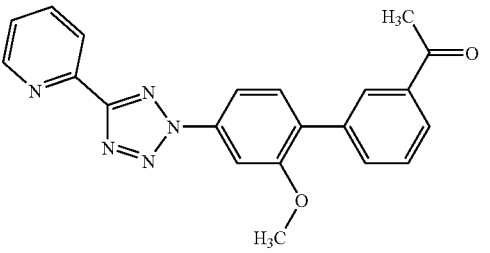 | ND | MS 372 (M⁺ + H) |
| 233. | 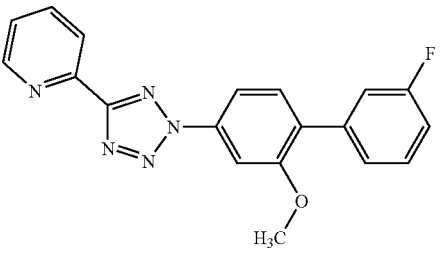 | ND | MS 348 (M⁺ + H) |
| 234. | 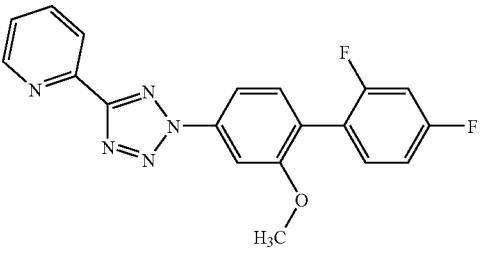 | ND | MS 366 (M⁺ + H) |

-continued
| EXAMPLE | Structure | ¹H NMR | MS (ESI) |
|---|---|---|---|
| 235. | 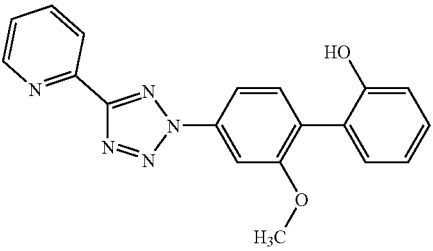 | ND | MS 346 (M⁺ + H) |
| 236. | 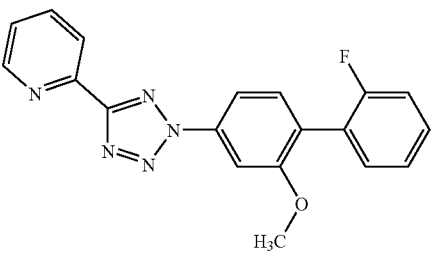 | ND | MS 348 (M⁺ + H) |
| 237. | 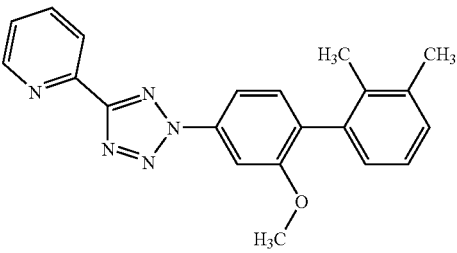 | ND | MS 358 (M⁺ + H) |
| 238. | 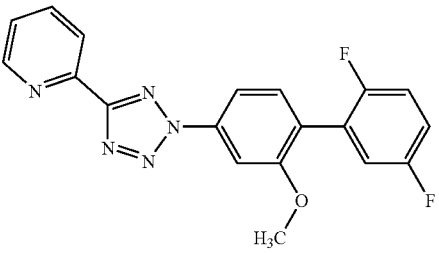 | ND | MS 366 (M⁺ + H) |
| 239. | 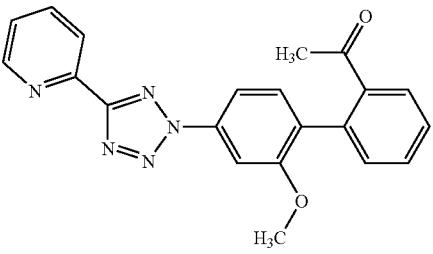 | ND | MS 372 (M⁺ + H) |
| 240. | 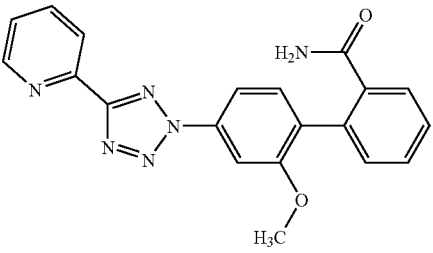 | ND | MS 373 (M⁺ + H) |

| EXAMPLE | Structure | ¹H NMR | MS (ESI) |
|---|---|---|---|
| 241. | 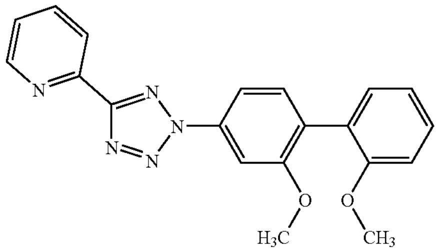 | ND | MS 360 (M⁺ + H) |
| 242. | 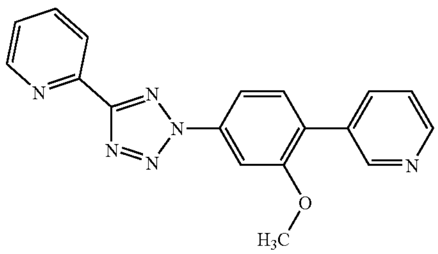 | ND | MS 331 (M⁺ + H) |
| 243. | 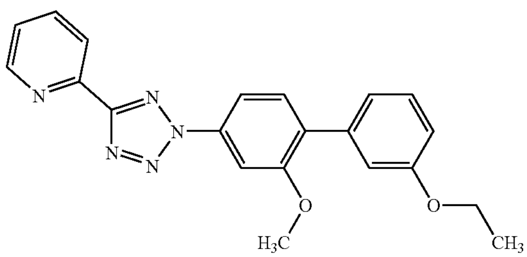 | ND | MS 374 (M⁺ + H) |
| 244. | 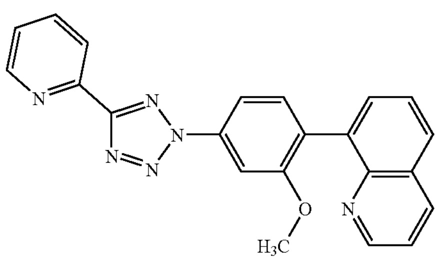 | ND | MS 381 (M⁺ + H) |
| 245. | 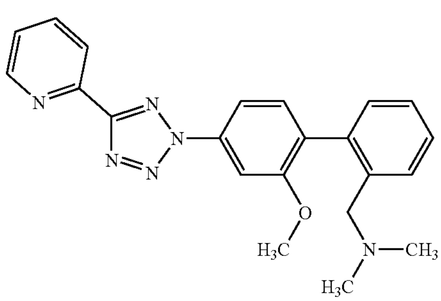 | ND | MS 387 (M⁺ + H) |

-continued
| EXAMPLE | Structure | ¹H NMR | MS (ESI) |
|---|---|---|---|
| 246. | 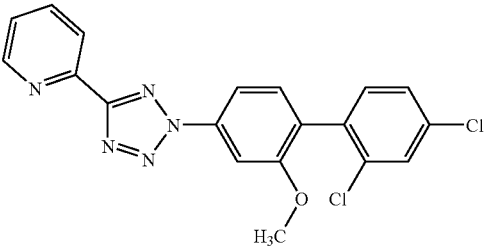 | ND | MS 399 (M⁺ + H) |
| 247. | 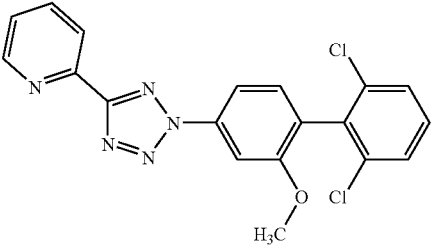 | ND | MS 399 (M⁺ + H) |
| 248. | 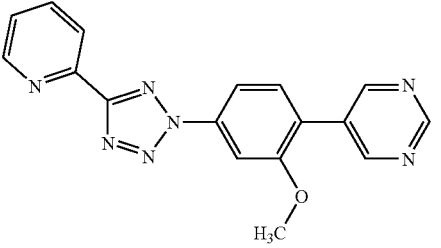 | ND | MS 332 (M⁺ + H) |
| 249. | 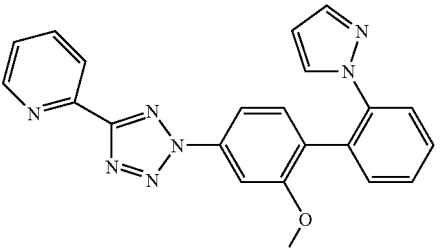 | ND | MS 396 (M⁺ + H) |
| 250. | 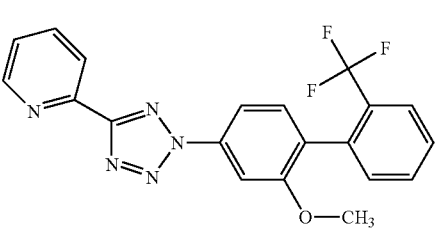 | ND | MS 398 (M⁺ + H) |
| 251. | 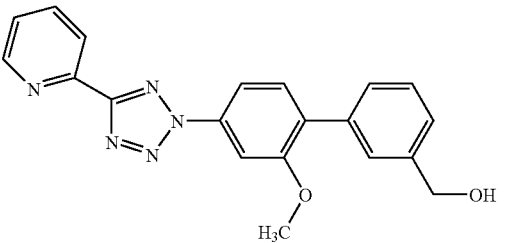 | ND | MS 360 (M⁺ + H) |

Examples 252-281 have mGluR5 inhibitory activity greater than 1 μM in the calcium flux assay:
| EXAMPLE | Structure | ¹H NMR | MS (ESI) |
|---|---|---|---|
| 252. | 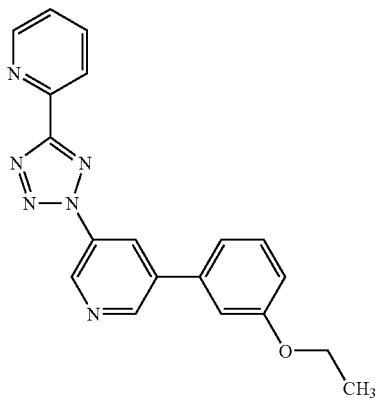 | ND | MS 345 (M + H) |
| 253. | 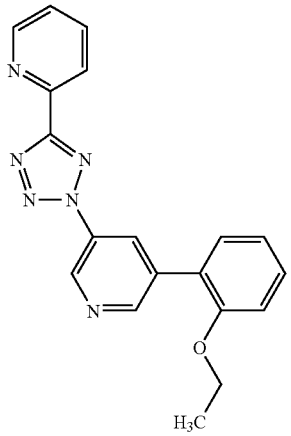 | ND | MS 345 (M + H) |
| 254. | 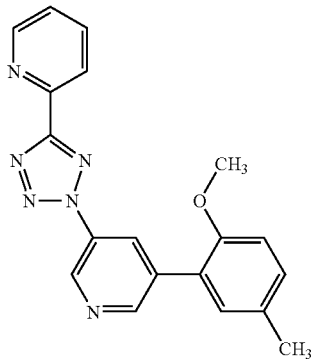 | ND | MS 345 (M + H) |

-continued
| EXAMPLE | Structure | ¹H NMR | MS (ESI) |
|---|---|---|---|
| 255. | 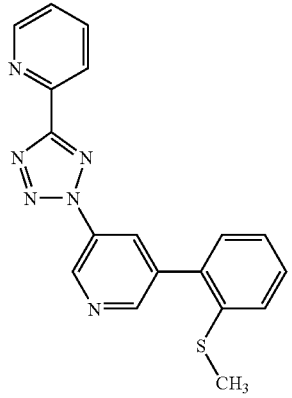 | ND | MS 347 (M + H) |
| 256. | 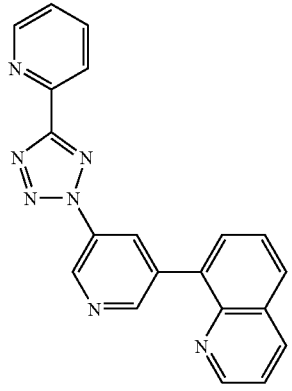 | ND | MS 352 (M + H) |
| 257. | 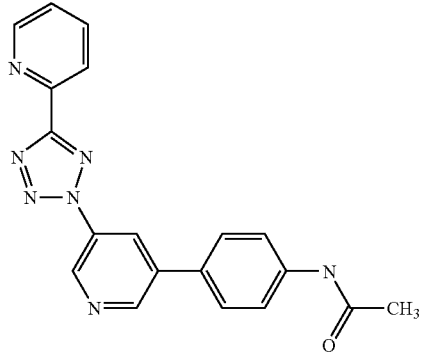 | ND | MS 358 (M + H) |
| 258. | 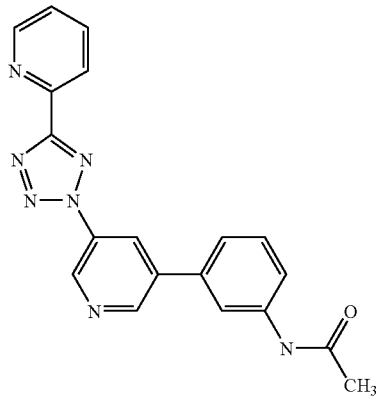 | ND | MS 358 (M + H) |

-continued
| EXAMPLE | Structure | ¹H NMR | MS (ESI) |
|---|---|---|---|
| 259. | 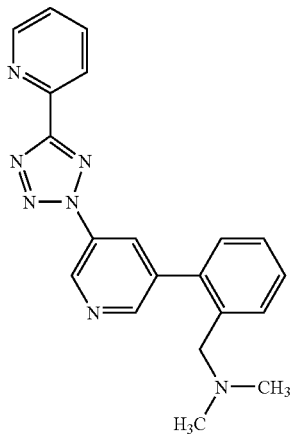 | ND | MS 358 (M + H) |
| 260. | 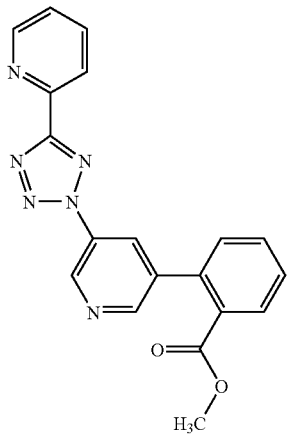 | ND | MS 359 (M + H) |
| 261. | 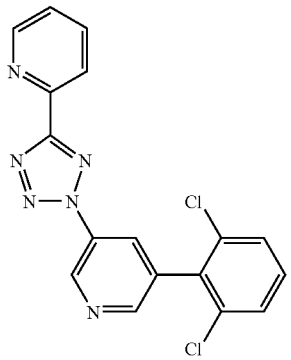 | ND | MS 370 (M + H) |

-continued
| EXAMPLE | Structure | $^1$H NMR | MS (ESI) |
|---|---|---|---|
| 262. | 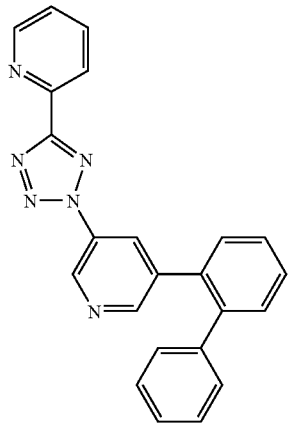 | ND | MS 377 (M + H) |
| 263. | 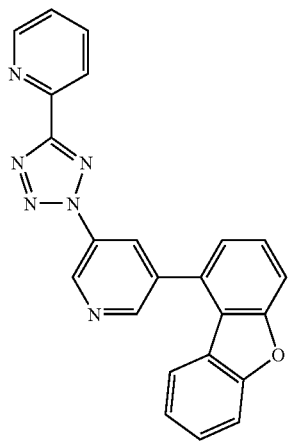 | ND | MS 391 (M + H) |
| 264. | 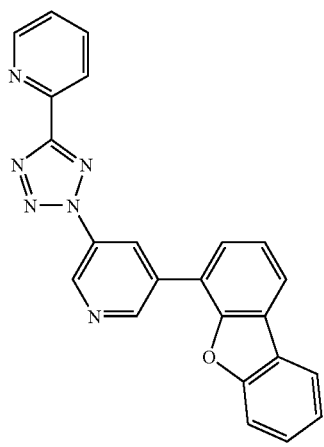 | ND | MS 391 (M + H) |

| EXAMPLE | Structure | ¹H NMR | MS (ESI) |
|---|---|---|---|
| 265. | 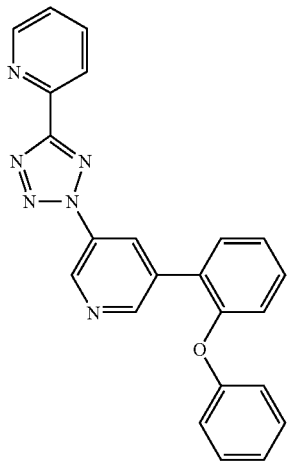 | ND | MS 393 (M + H) |
| 266. | 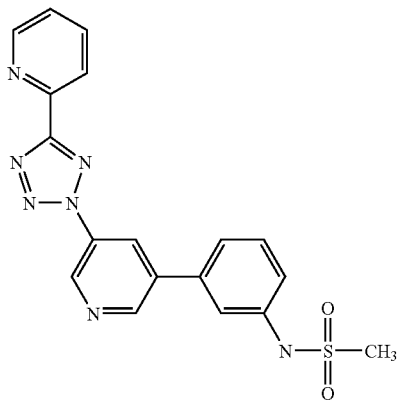 | ND | MS 394 (M + H) |
| 267. | 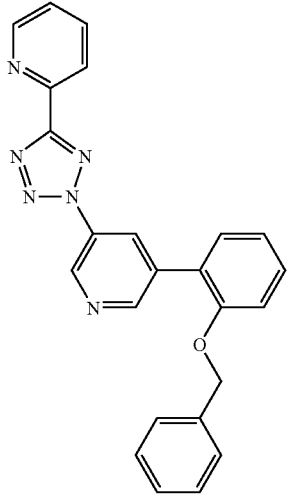 | ND | MS 407 (M + H) |

-continued
| EXAMPLE | Structure | ¹H NMR | MS (ESI) |
|---|---|---|---|
| 268. | 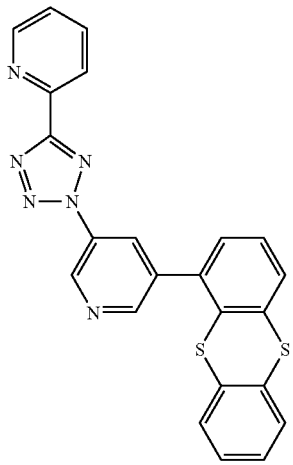 | ND | MS 439 (M + H) |
| 269. | 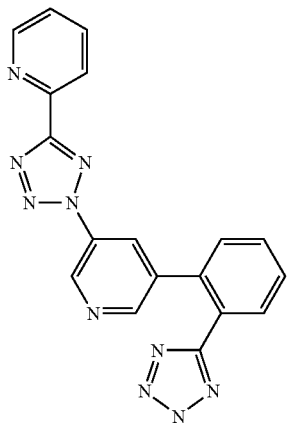 | ND | MS 369 (M + H) |
| 270. | 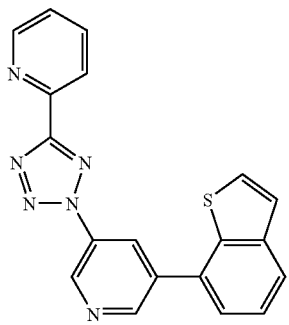 | ND | MS 357 (M + H) |

-continued

| EXAMPLE | Structure | ¹H NMR | MS (ESI) |
|---|---|---|---|
| 271. | 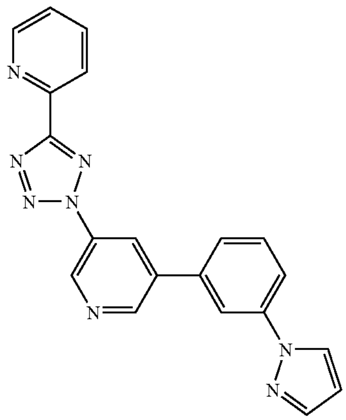 | ND | MS 367 (M + H) |
| 272. | 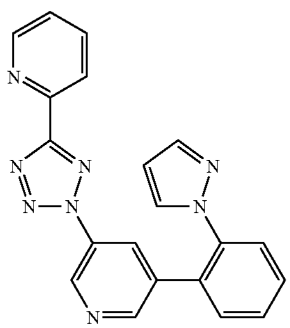 | ND | MS 367 (M + H) |
| 273. | 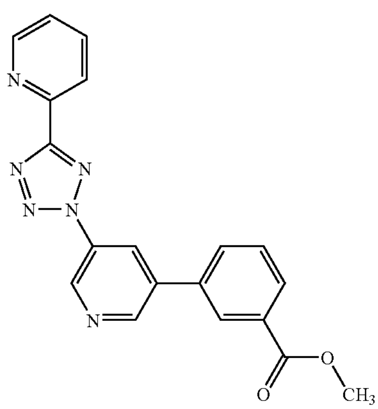 | ND | MS 359 (M + H) |
| 274. | 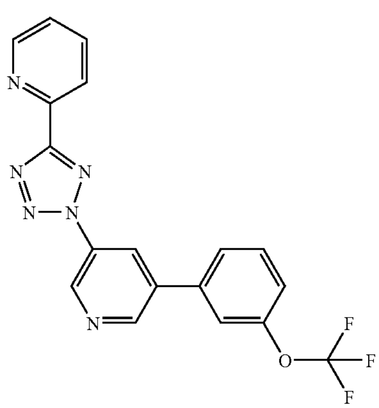 | ND | MS 385 (M + H) |

-continued
| EXAMPLE | Structure | ¹H NMR | MS (ESI) |
|---|---|---|---|
| 275. | 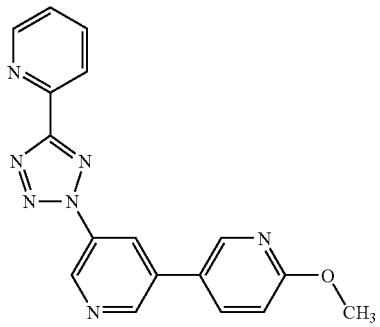 | ND | MS 332 (M + H) |
| 276. | 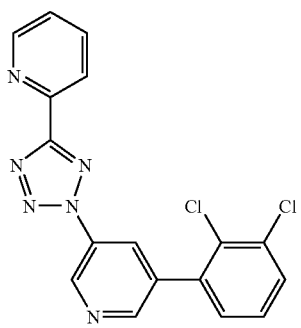 | ND | MS 370 (M + H) |
| 277. | 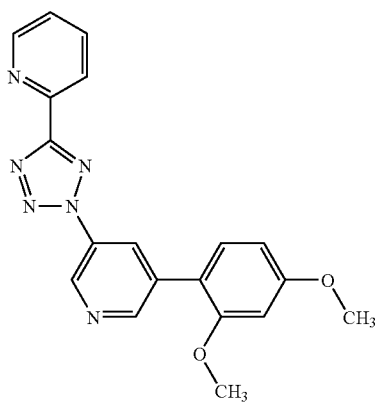 | ND | MS 361 (M + H) |
| 278. | 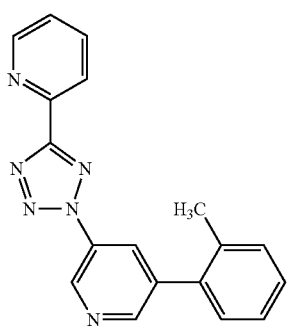 | ND | MS 315 (M + H) |

-continued
| EXAMPLE | Structure | ¹H NMR | MS (ESI) |
|---|---|---|---|
| 279. | 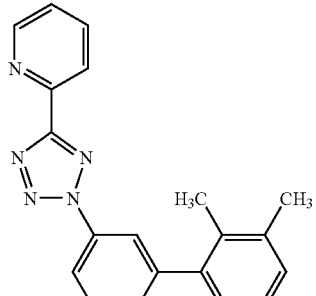 | ND | MS 329 (M + H) |
| 280. | 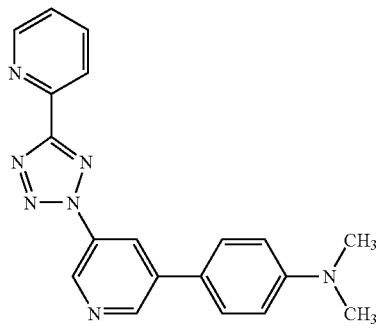 | ND | MS 344 (M + H) |
| 281. | 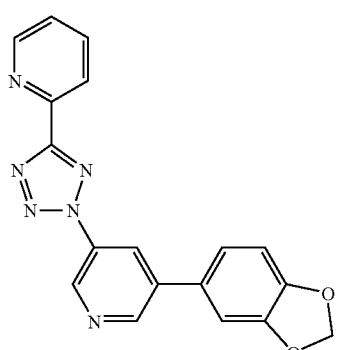 | ND | MS 345 (M + H) |
Examples 282-347 have mGluR5 inhibitory activity greater than 3 μM in the calcium flux assay:
| EXAMPLE | Structure | ¹H NMR | MS (ESI) |
|---|---|---|---|
| 282. | 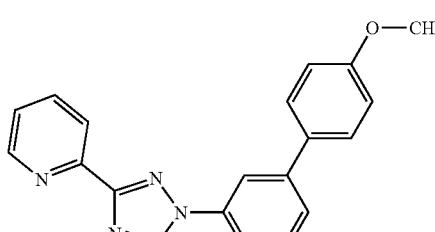 | ND | MS 330 (M + H) |

-continued
| EXAMPLE | Structure | ¹H NMR | MS (ESI) |
|---|---|---|---|
| 283. | 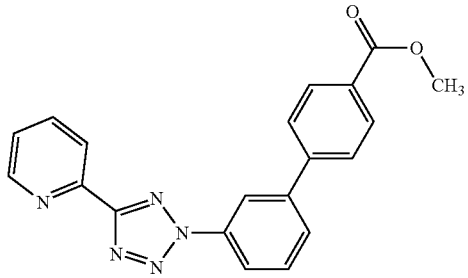 | ND | MS 358 (M + H) |
| 284. | 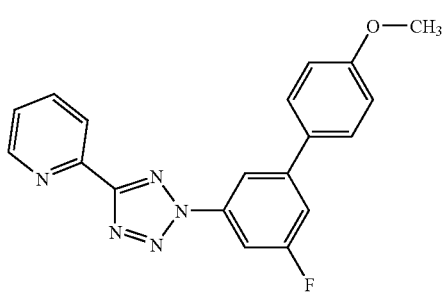 | ND | MS 348 (M + H) |
| 285. | 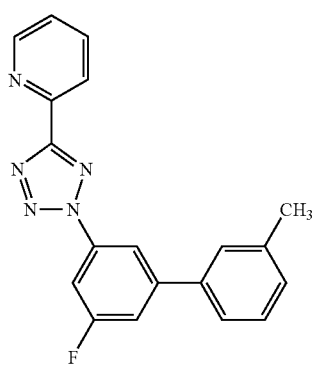 | ND | MS 332 (M + H) |
| 286. | 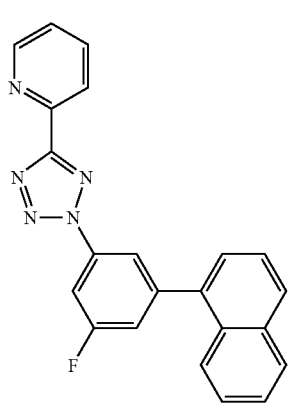 | ND | MS 368 (M + H) |

-continued

| EXAMPLE | Structure | ¹H NMR | MS (ESI) |
|---|---|---|---|
| 287. | 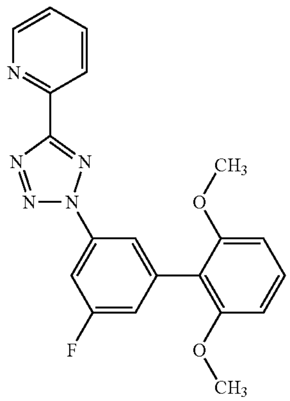 | ND | MS 378 (M + H) |
| 288. | 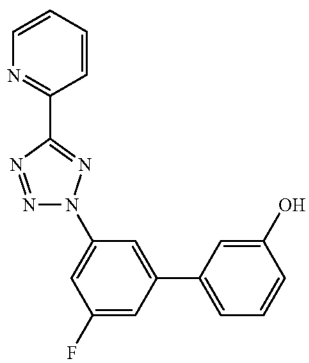 | ND | MS 334 (M + H) |
| 289. | 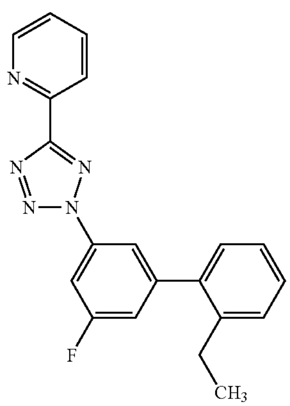 | ND | MS 346 (M + H) |
| 290. | 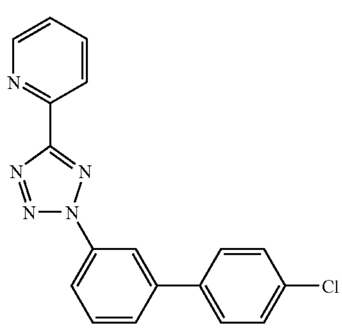 | ND | MS 334 (M + H) |

| EXAMPLE | Structure | ¹H NMR | MS (ESI) |
|---|---|---|---|
| 291. | 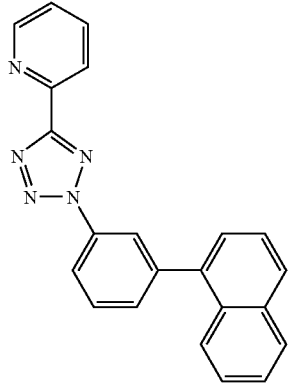 | ND | MS 350 (M + H) |
| 292. | 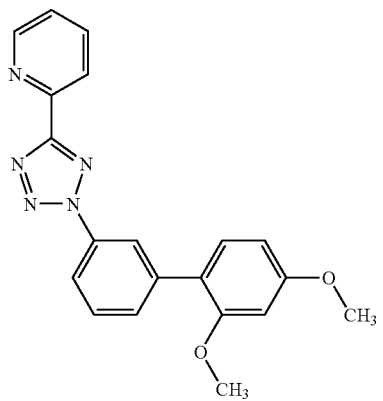 | ND | MS 360 (M + H) |
| 293. | 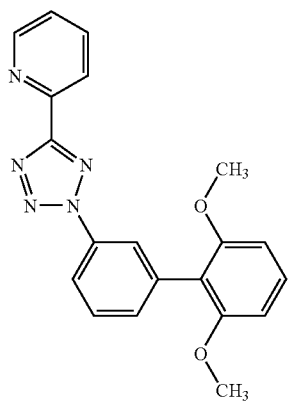 | ND | MS 360 (M + H) |
| 294. | 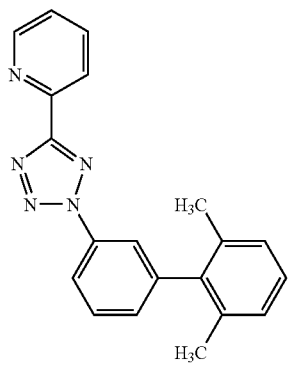 | ND | MS 328 (M + H) |

-continued

| EXAMPLE | Structure | ¹H NMR | MS (ESI) |
|---|---|---|---|
| 295. | 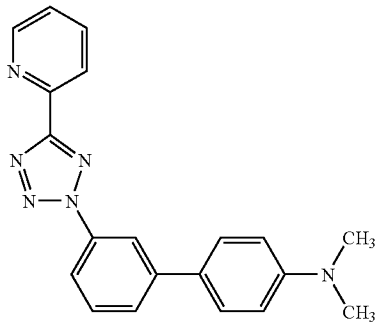 | ND | MS 343 (M + H) |
| 296. | 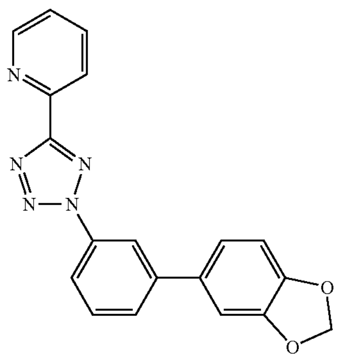 | ND | MS 344 (M + H) |
| 297. | 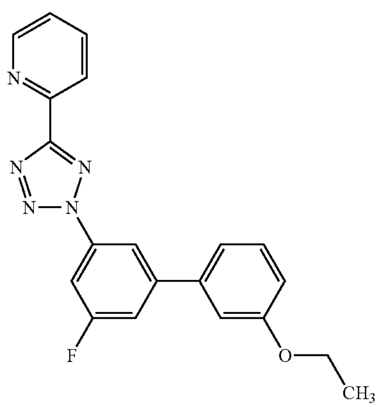 | ND | MS 362 (M + H) |
| 298. | 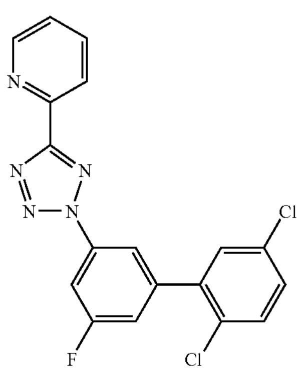 | ND | MS 387 (M + H) |

-continued
| EXAMPLE | Structure | ¹H NMR | MS (ESI) |
|---|---|---|---|
| 299. | 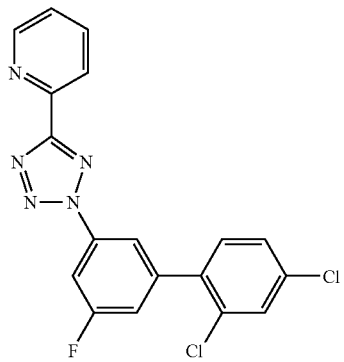 | ND | MS 387 (M + H) |
| 300. | 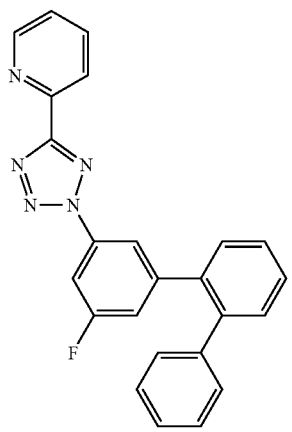 | ND | MS 394 (M + H) |
| 301. | 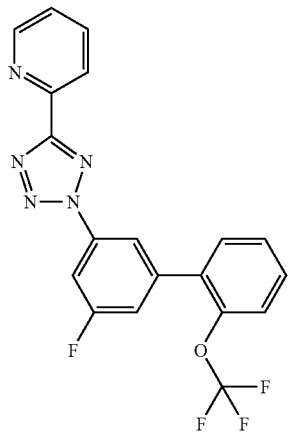 | ND | MS 402 (M + H) |

-continued

| EXAMPLE | Structure | $^1$H NMR | MS (ESI) |
|---|---|---|---|
| 302. | 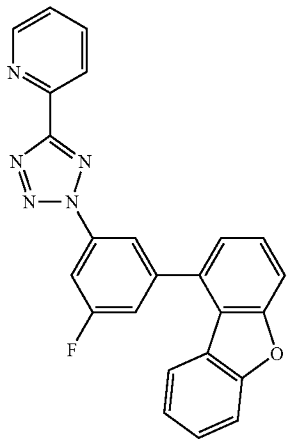 | ND | MS 408 (M + H) |
| 303. | 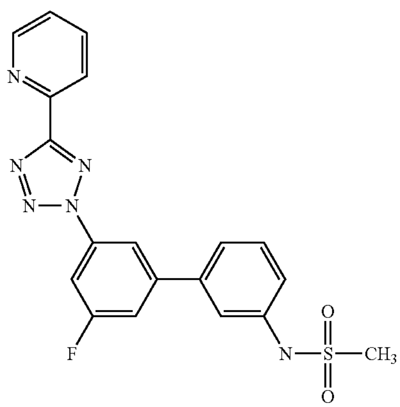 | ND | MS 411 (M + H) |
| 304. | 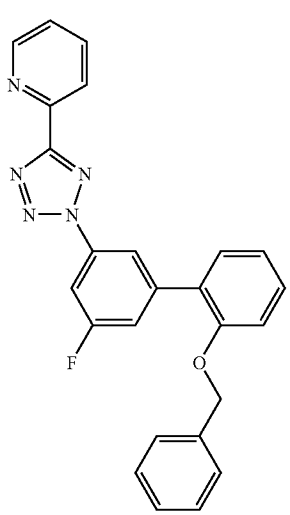 | ND | MS 424 (M + H) |

-continued

| EXAMPLE | Structure | ¹H NMR | MS (ESI) |
|---|---|---|---|
| 305. | 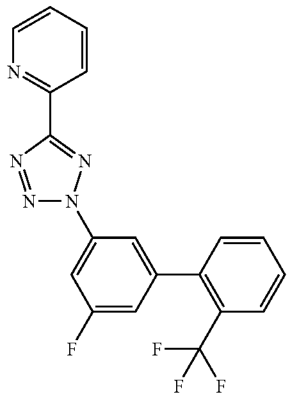 | ND | MS 386 (M + H) |
| 306. | 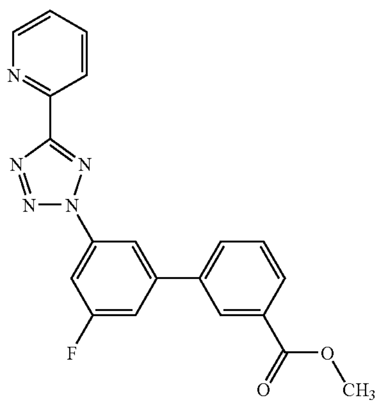 | ND | MS 376 (M + H) |
| 307. | 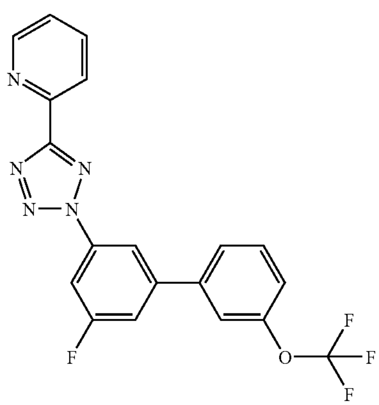 | ND | MS 402 (M + H) |
| 308. | 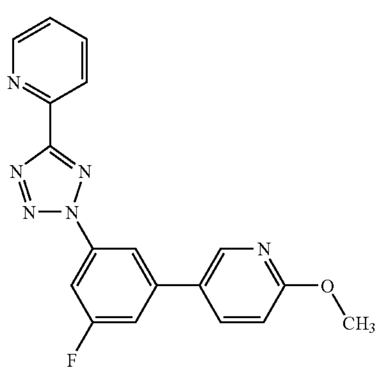 | ND | MS 349 (M + H) |

-continued
| EXAMPLE | Structure | ¹H NMR | MS (ESI) |
|---|---|---|---|
| 309. | 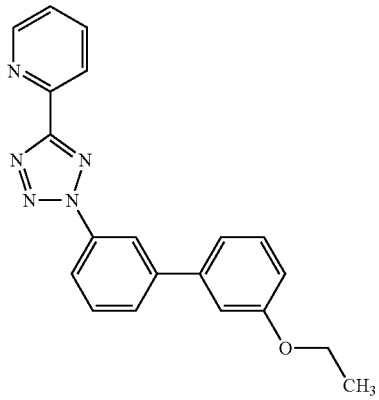 | ND | MS 344 (M + H) |
| 310. | 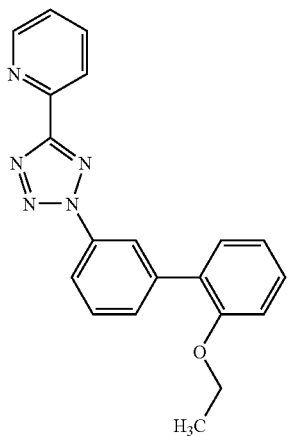 | ND | MS 344 (M + H) |
| 311. | 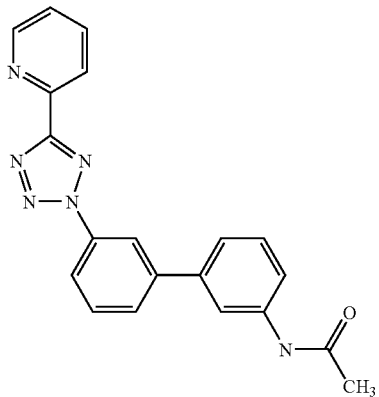 | ND | MS 357 (M + H) |

-continued
| EXAMPLE | Structure | ¹H NMR | MS (ESI) |
| --- | --- | --- | --- |
| 312. | 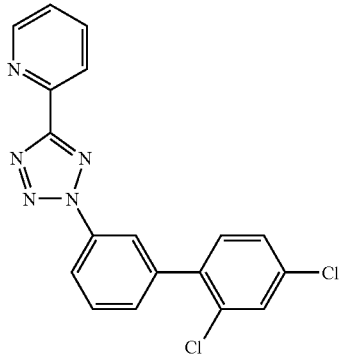 | ND | MS 369 (M + H) |
| 313. | 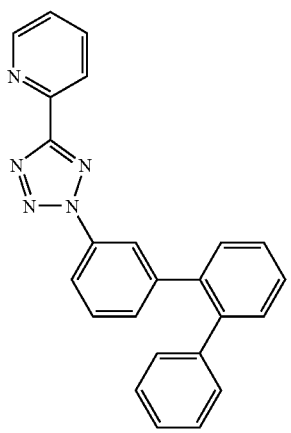 | ND | MS 376 (M + H) |
| 314. | 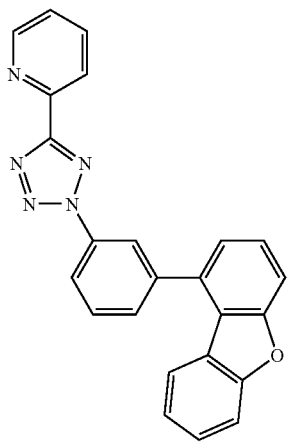 | ND | MS 390 (M + H) |

-continued

| EXAMPLE | Structure | ¹H NMR | MS (ESI) |
|---|---|---|---|
| 315. | 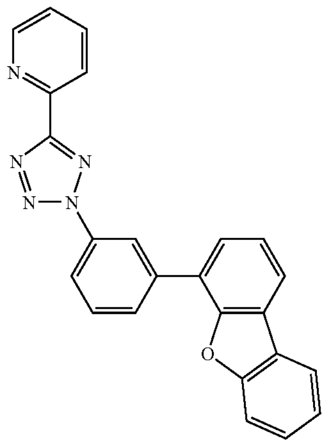 | ND | MS 390 (M + H) |
| 316. | 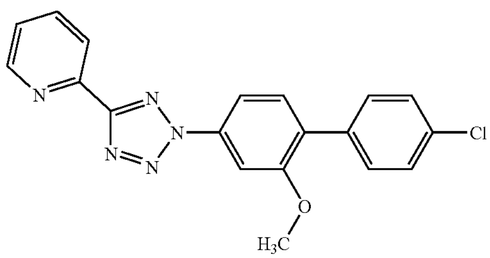 | ND | MS 364 (M + H) |
| 317. | 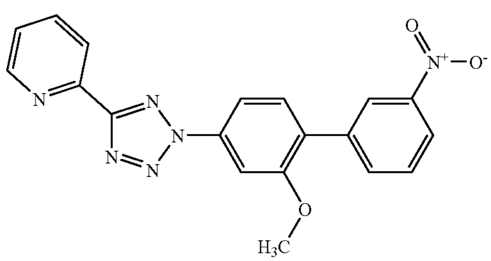 | ND | MS 375 (M + H) |
| 318. | 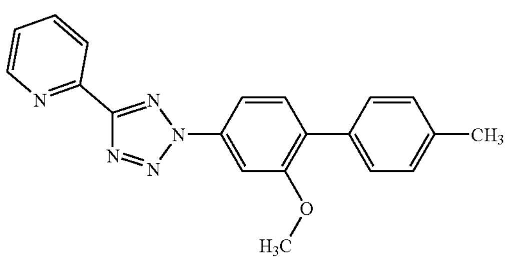 | ND | MS 344 (M + H) |
| 319. | 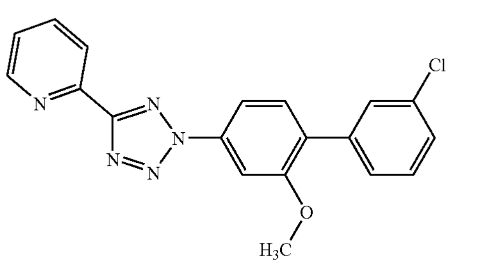 | ND | MS 364 (M + H) |

-continued

| EXAMPLE | Structure | ¹H NMR | MS (ESI) |
|---|---|---|---|
| 320. | 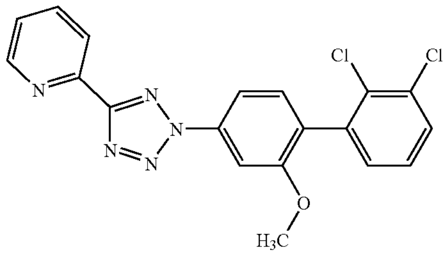 | ND | MS 399 (M + H) |
| 321. | 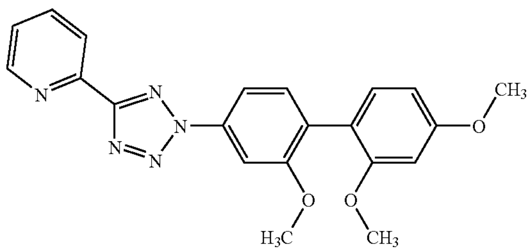 | ND | MS 390 (M + H) |
| 322. | 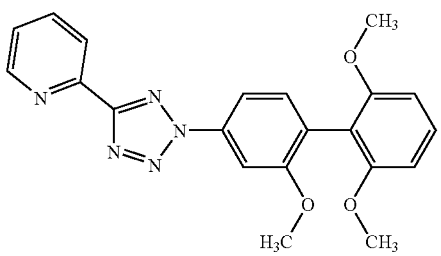 | ND | MS 390 (M + H) |
| 323. | 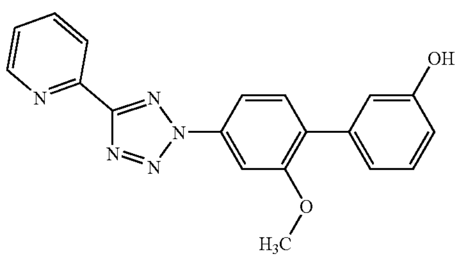 | ND | MS 346 (M + H) |
| 324. | 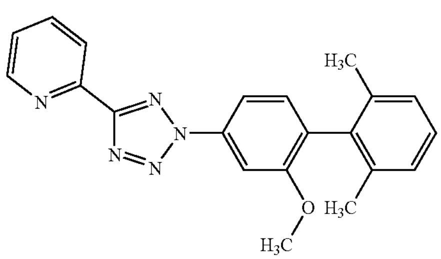 | ND | MS 358 (M + H) |
| 325. | 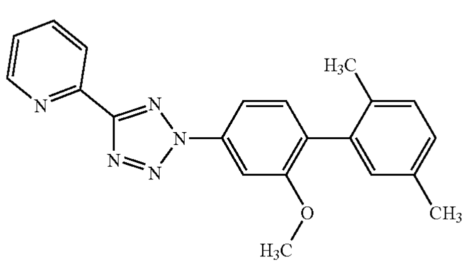 | ND | MS 358 (M + H) |

-continued

| EXAMPLE | Structure | ¹H NMR | MS (ESI) |
| --- | --- | --- | --- |
| 326. | 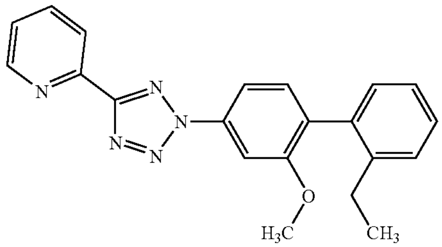 | ND | MS 358 (M + H) |
| 327. | 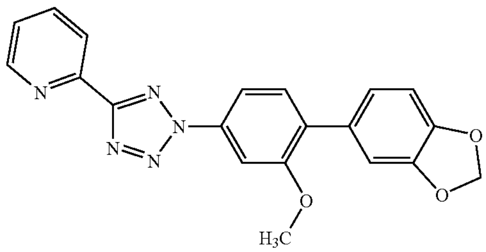 | ND | MS 374 (M + H) |
| 328. | 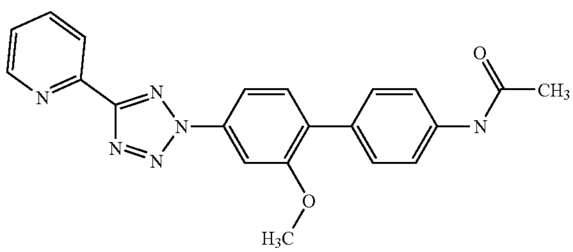 | ND | MS 387 (M + H) |
| 329. | 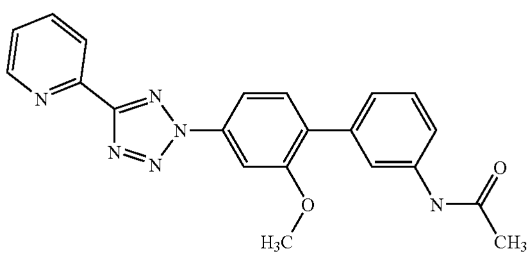 | ND | MS 387 (M + H) |
| 330. | 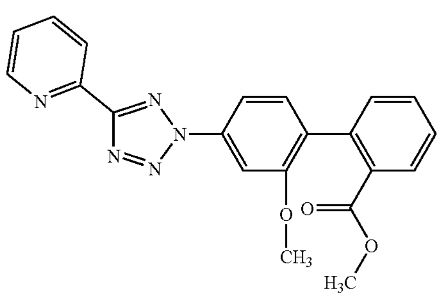 | ND | MS 388 (M + H) |
| 331. | 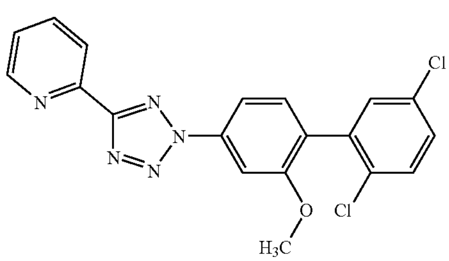 | ND | MS 399 (M + H) |

-continued

| EXAMPLE | Structure | ¹H NMR | MS (ESI) |
|---|---|---|---|
| 332. | 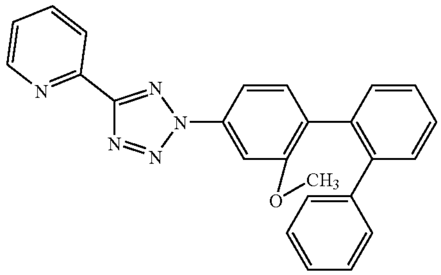 | ND | MS 406 (M + H) |
| 333. | 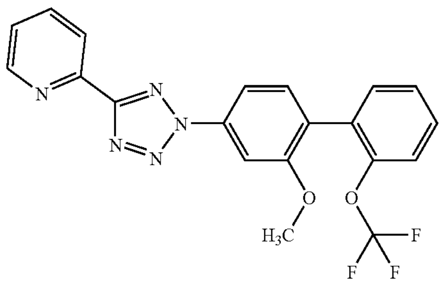 | ND | MS 414 (M + H) |
| 334. | 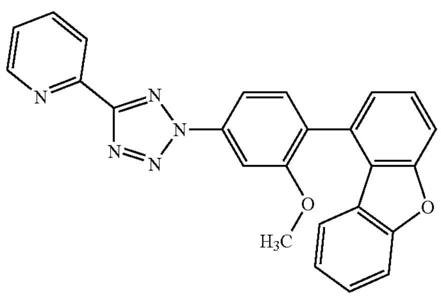 | ND | MS 420 (M + H) |
| 335. | 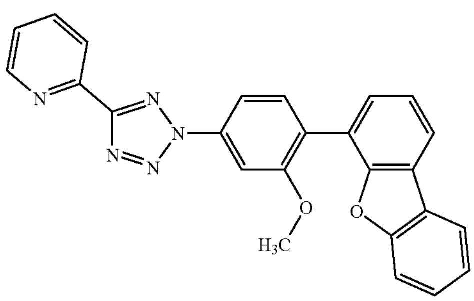 | ND | MS 420 (M + H) |
| 336. | 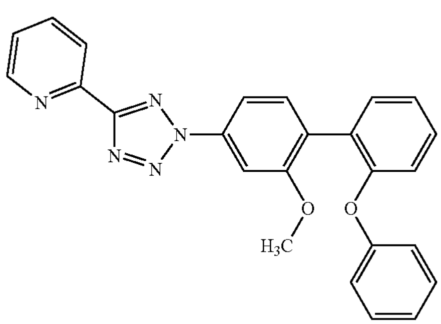 | ND | MS 422 (M + H) |

-continued

| EXAMPLE | Structure | ¹H NMR | MS (ESI) |
|---|---|---|---|
| 337. | 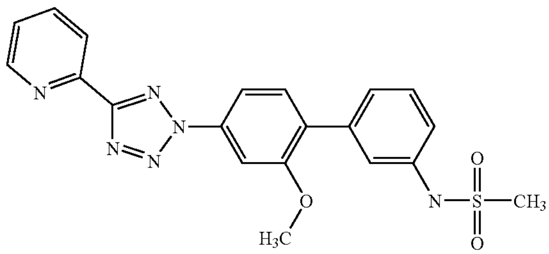 | ND | MS 423 (M + H) |
| 338. | 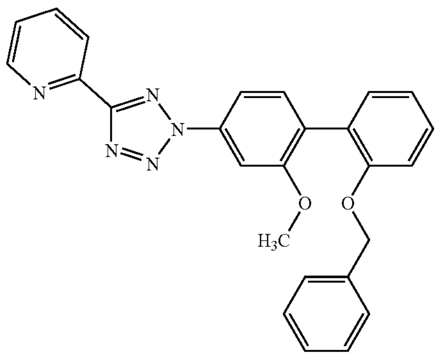 | ND | MS 436 (M + H) |
| 339. | 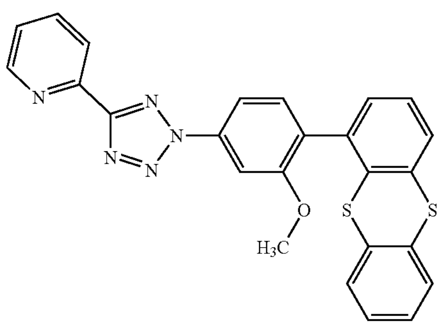 | ND | MS 468 (M + H) |
| 340. | 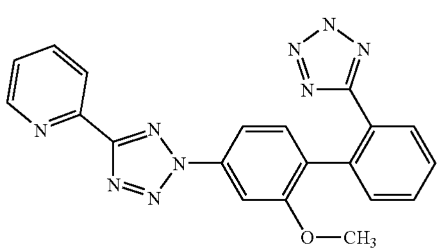 | ND | MS 398 (M + H) |
| 341. | 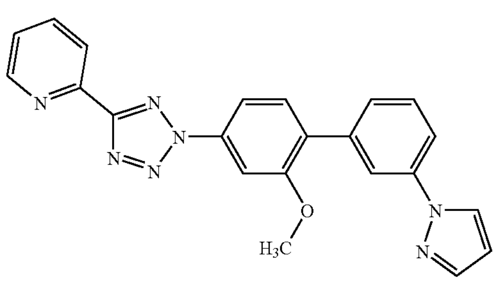 | ND | MS 396 (M + H) |

-continued
| EXAMPLE | Structure | ¹H NMR | MS (ESI) |
|---|---|---|---|
| 342. | 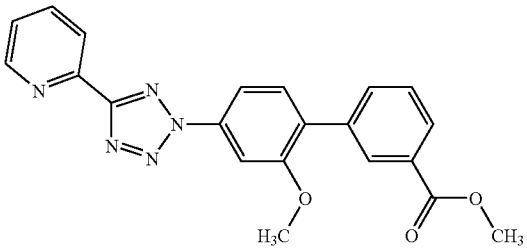 | ND | MS 388 (M + H) |
| 343. | 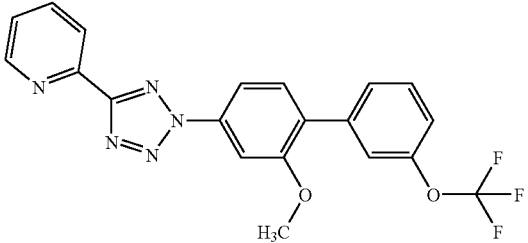 | ND | MS 414 (M + H) |
| 344. | 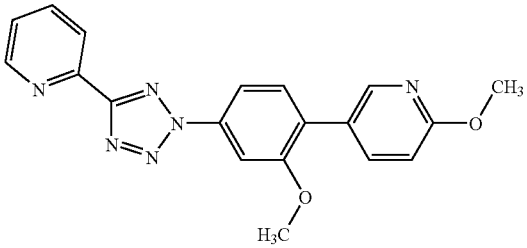 | ND | MS 361 (M + H) |
| 345. | 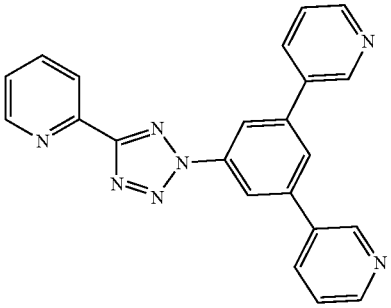 | 8.91-8.92(d, 2H), 8.75-8.79 (m, 2H), 8.27-8.29 (d, 2H), 7.97-8.06 (m, 2H), 7.58-7.60 (dd, 1H), 7.46-7.49 (m, 2H). | MS 378 (M⁺ + H) |
| 346. | 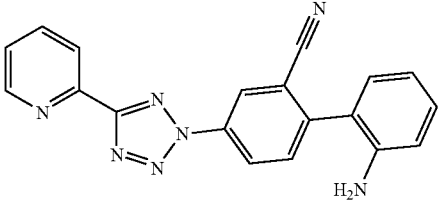 | 8.2 (s, 1R), 8.98-9.00 (d, J=6, 1H), 8.84-8.85(d, J=3, 1H), 8.55-8.59 (m, 2H), 8.33-8.35 (d, J=6, 1H), 8.10-8.12 (t, 1H), 8.64-8.66 (t, 1H), 7.58 (s, 2H), 7.39 (s, 1H), 7.33-7.38 (m, 2H). | MS 340.1 (M⁺ + H) |
| 347. | 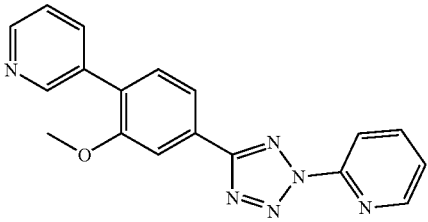 | 8.85 (br s, 1H), 8.74 (d, 1H), 8.6 (d, 1H), 8.3 (d, 1H), 8.1-8.05 (m, 2H), 7.95 (s, 1H), 7.92 (d, 1H), 7.6-7.55 (m, 1H), 7.5 (d, 1H), 7.4-7.37 (m, 1H), 3.98 (s, 3H). | MS 331.8 (M⁺ + H). |

Other variations or modifications, which will be obvious to those skilled in the art, are within the scope and teachings of this invention. This invention is not to be limited except as set forth in the following claims.

What is claimed is:

1. A compound of the Formula (I):

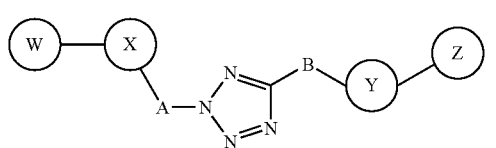

wherein:
X is phenyl;
Y is 2-pyridyl;
A is $C_0$ alkyl,
B is $C_0$ alkyl,
X is optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —$O(aryl)$, —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups;
A is $C_0$alkyl, B is —$C_0$alkyl,
Y is optionally substituted with 1-7 independent halogen, —CN, $NO_2$, —$C_{1-6}$alkyl, —$C_{1-6}$alkenyl, —$C_{1-6}$alkynyl, —$OR^5$, —$NR^5R^6$, —$C(=NR^5)NR^6R^7$, —$N(=NR^5)NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —$C(=NR^5)R^6$, or —$C(=NOR^5)R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —$O(aryl)$, —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups;
W is —$C_{3-7}$cycloalkyl, -hetero$C_{3-7}$cycloalkyl, —$C_{0-6}$alkylaryl, or —$C_{0-6}$alkylheteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents;
Z is —$C_{3-7}$cycloalkyl, -hetero$C_{3-7}$cycloalkyl, —$C_{0-6}$alkylaryl, or —$C_{0-6}$alkylheteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents;
one of W and Z is optionally absent;
$R^1$, $R^2$, and $R^3$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —$O(C_{0-6}$alkyl), —$O(C_{3-7}$cycloalkyl), —$O(aryl)$, —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;
$R^4$ is —$C_{1-6}$alkyl, —$C_{3-7}$cycloalkyl, heteroaryl, or aryl; optionally substituted with 1-5 independent halogen, —CN, —$C_{1-6}$alkyl, —$O(C_{0-6}$alkyl), —$O(C_{3-7}$cycloalkyl), —$O(aryl)$,—$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;
$R^5$, $R^6$, and $R^7$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —$O(C_{0-6}$alkyl), —$O(C_{3-7}$cycloalkyl), —$O(aryl)$, —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;
$R^8$ is —$C_{1-6}$alkyl, —$C_{3-7}$cycloalkyl, heteroaryl, or aryl; optionally substituted with 1-5 independent halogen, —CN, —$C_{1-6}$alkyl, —$O(C_{0-6}$alkyl), —$O(C_{3-7}$cycloalkyl), —$O(aryl)$, —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;
$R^9$ and $R^{10}$ each independently is —$C_{0-6}$alkyl, —$C_{3-7}$cycloalkyl, heteroaryl, or aryl; any of which is optionally substituted with 1-5 independent halogen, —CN, —$C_{1-6}$alkyl, —$O(C_{0-6}$alkyl), —$O(C_{3-7}$cycloalkyl), —$O(aryl)$, —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents; and
any N may be an N-oxide;
or a pharmaceutically acceptable salt thereof.

2. The compound according to claim 1 wherein:
X is phenyl, which is optionally substituted with 1-5 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —$O(aryl)$, —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups.

3. The compound according to claim 1 wherein:
Y is 2-pyridyl, which is optionally substituted with 1-4 independent halogen, —CN, $NO_2$, —$C_{1-6}$alkyl, —$C_1$alkenyl, —$C_{1-6}$alkynyl, —$OR^5$, —$NR^5R^6$, —$C(=NR^5)NR^6R^7$, —$N(=NR^5)NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —$C(=NR^5)R^6$, or —$C(=NOR^5)R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups.

4. The compound according to claim 1 wherein:
W is —$C_{0-6}$alkylaryl, or —$C_{0-6}$alkylheteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents.

5. A compound which is selected from the group consisting of:
  1-methyl-3-[3-(5-pyridin-2-yl-2H-tetrazol-2-yl)phenyl]imidazolidin-2-one;
  2-[2-(4-pyridin-2-ylphenyl)-2H-tetrazol-5-yl]pyridine;
  2-[2-(4-pyridin-4-ylphenyl)-2H-tetrazol-5-yl]pyridine;
  2-{2-[3-(1H-imidazol-1-yl)phenyl]-2H-tetrazol-5-yl}pyridine;
  2-[2-(2-pyrazin-3-ylphenyl)-2H-tetrazol-5-yl]pyridine;
  2-[2-(4-morpholin-3-ylphenyl)-2H-tetrazol-5-yl]pyridine;
  2-{2-[3-(2H-tetrazol-5-yl)phenyl]-2H-tetrazol--yl}pyridine; and
  2-pyridin-2-yl-5-(5-pyridin-2-yl-2H-tetrazol-2-yl)benzonitrile;
or a pharmaceutically acceptable salt thereof.

6. A compound which selected from the group consisting of:

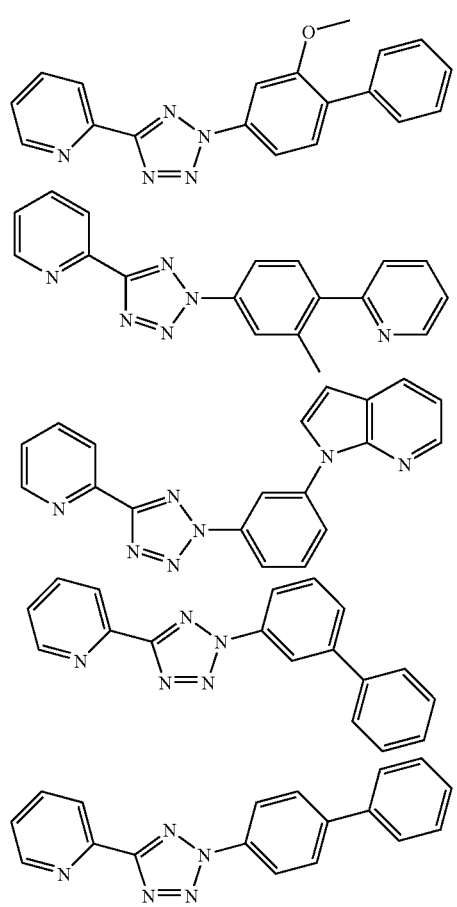

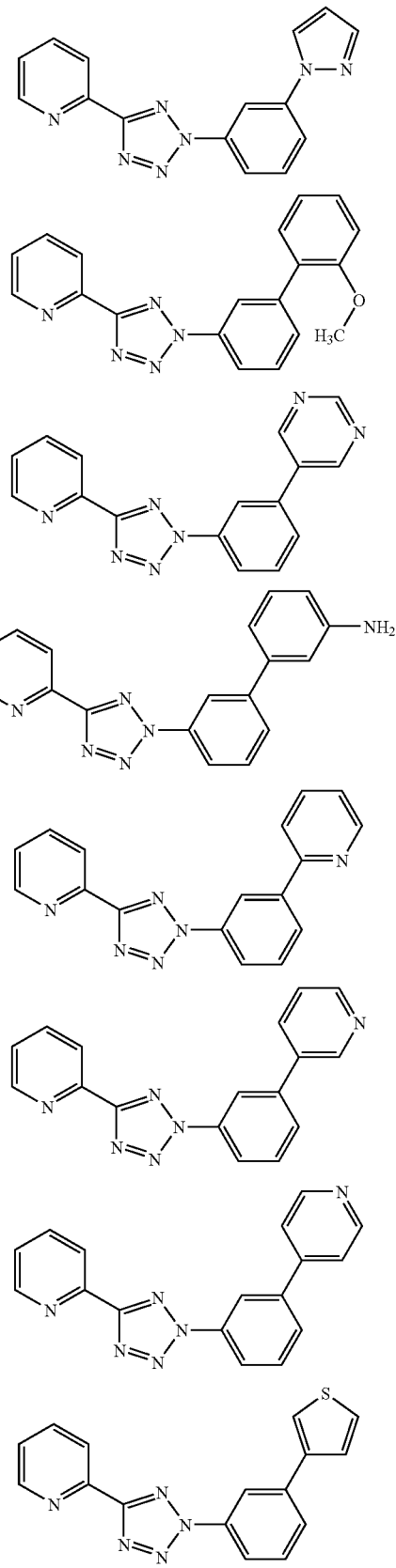

-continued
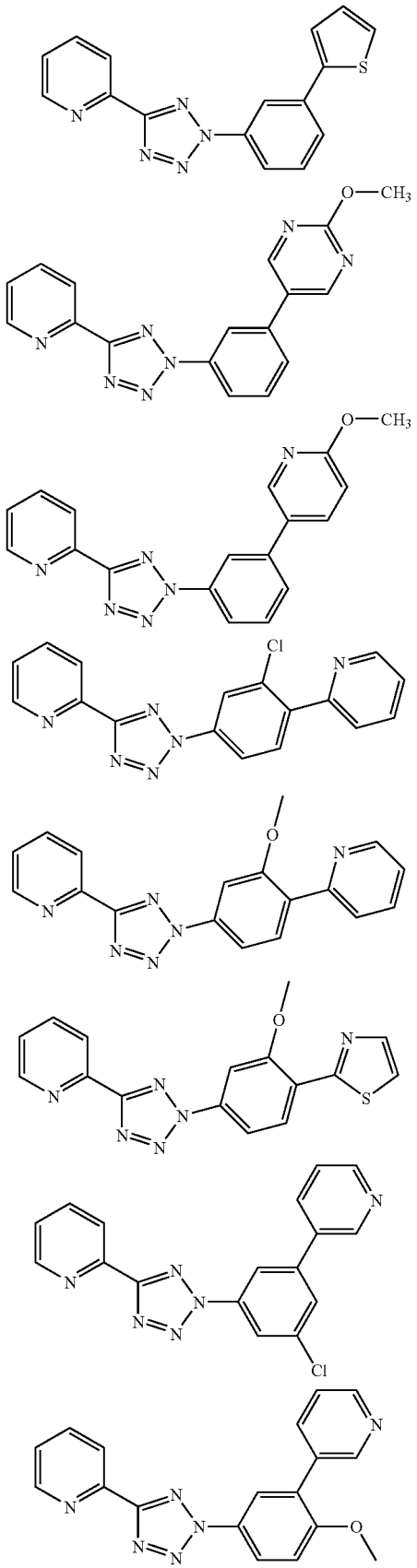
-continued
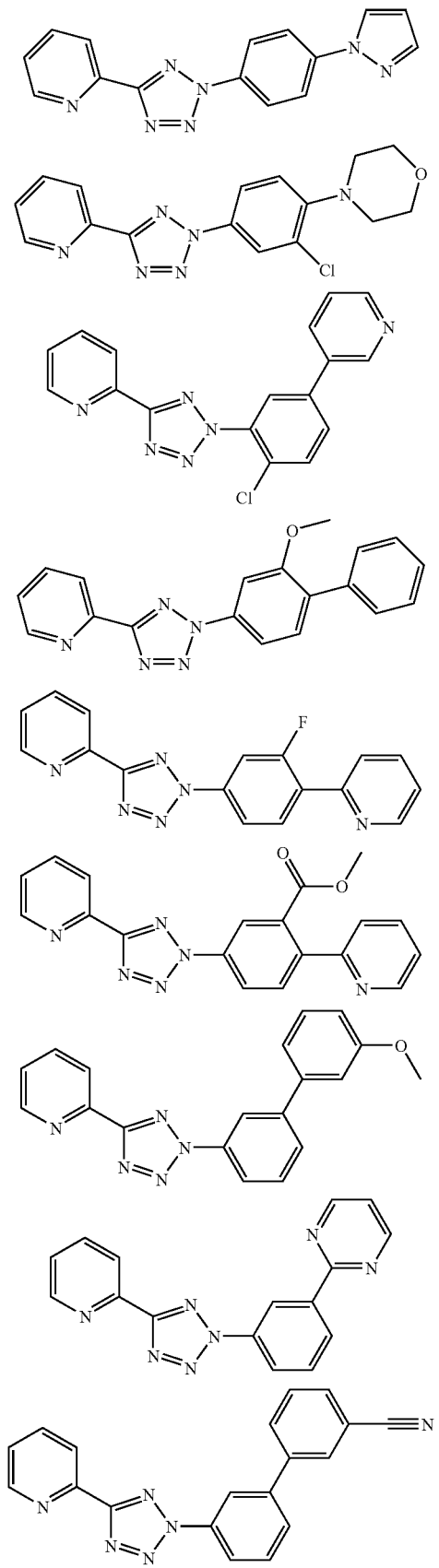

-continued
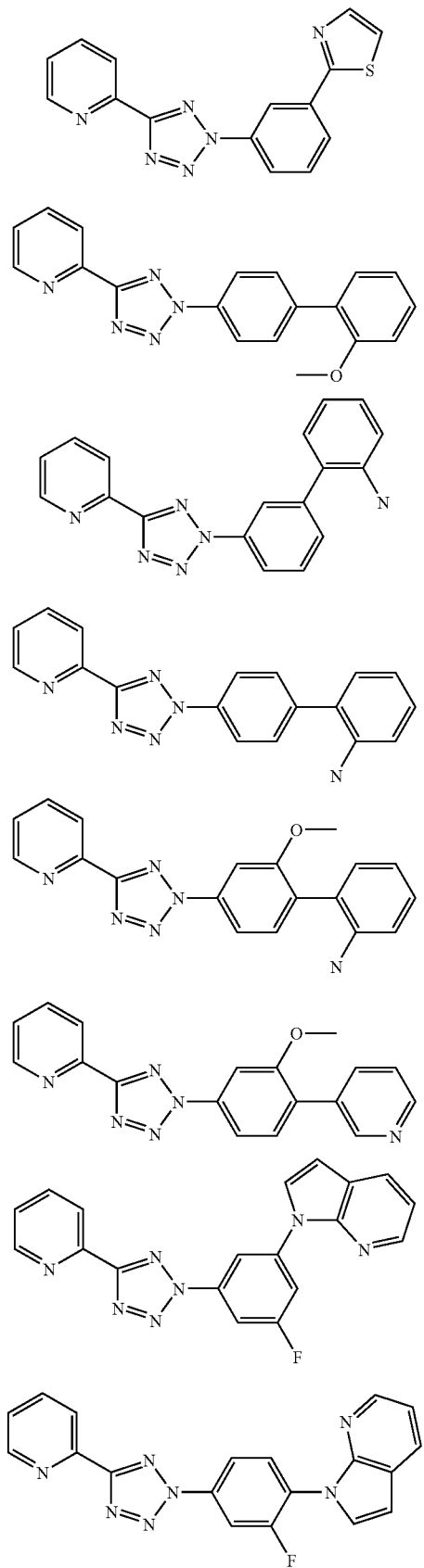
-continued
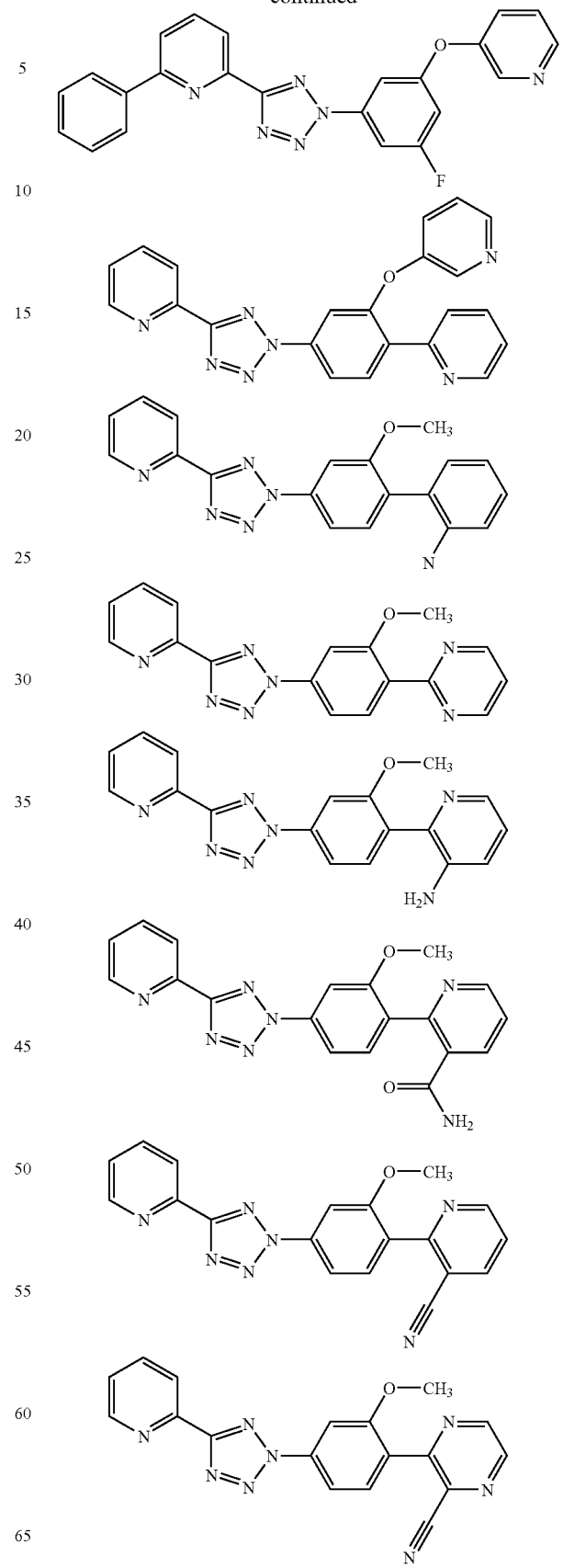

-continued
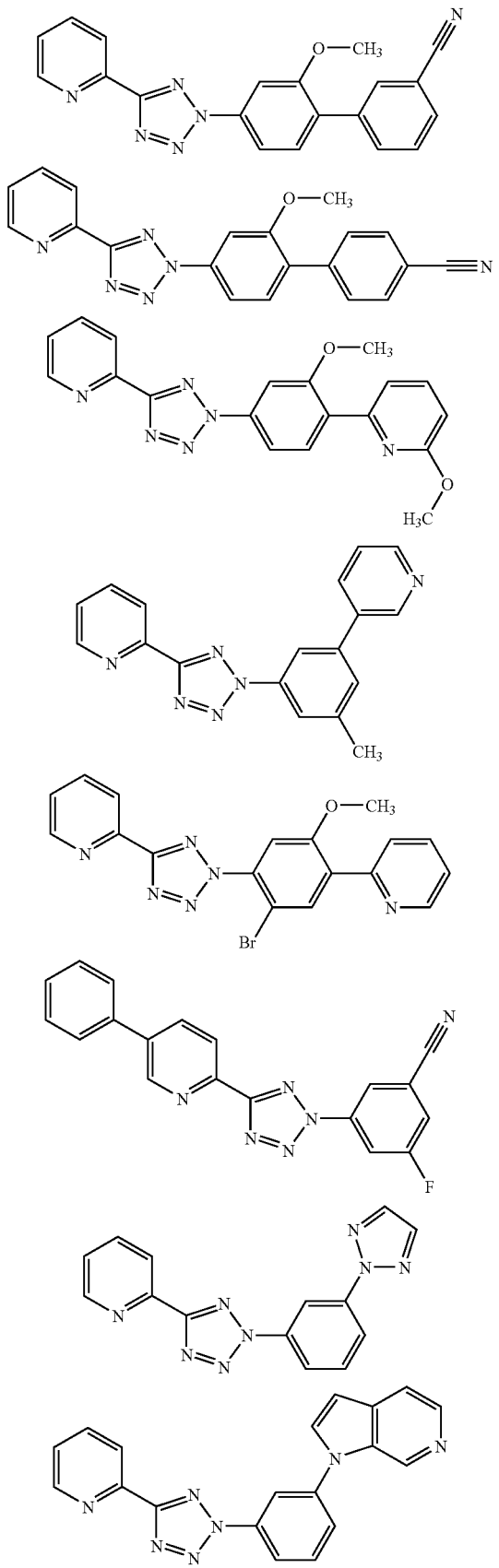
-continued
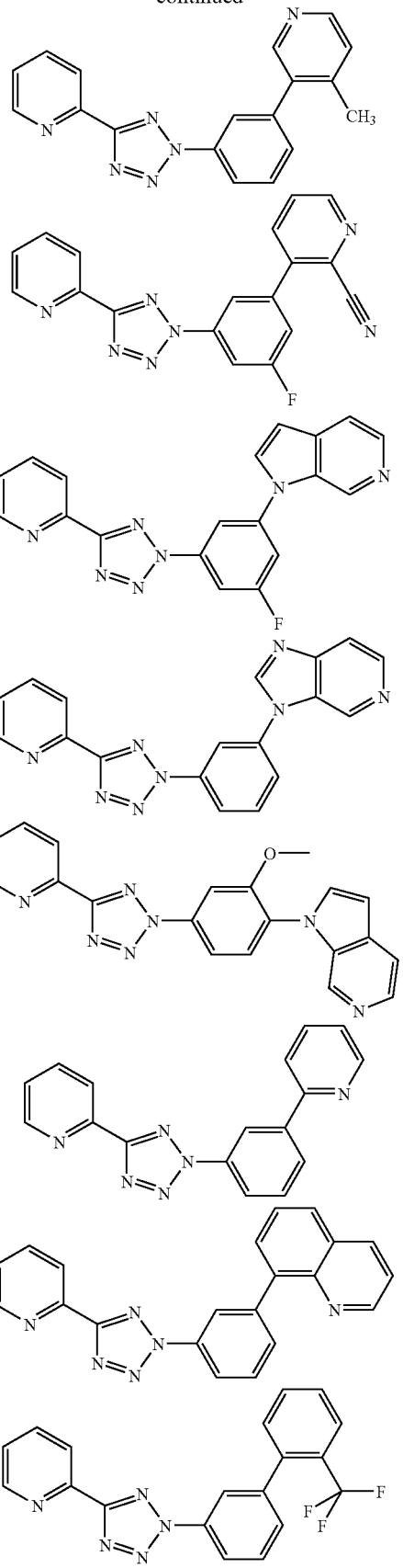

-continued
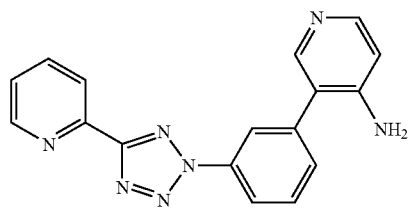
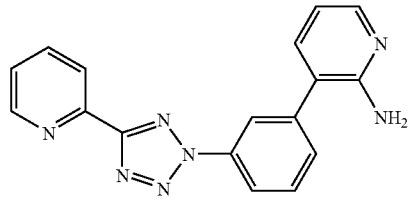
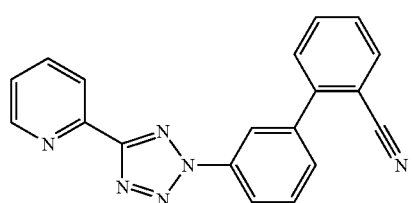
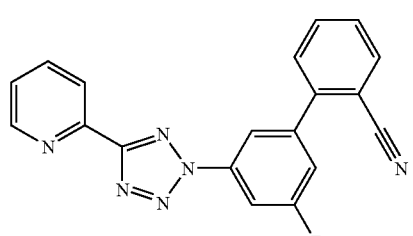
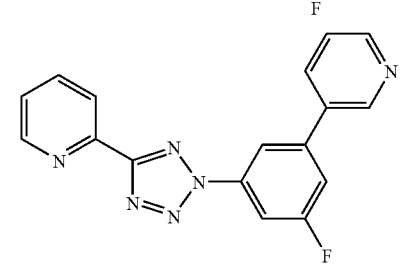
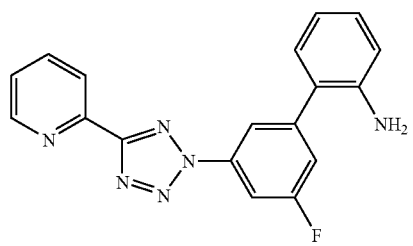
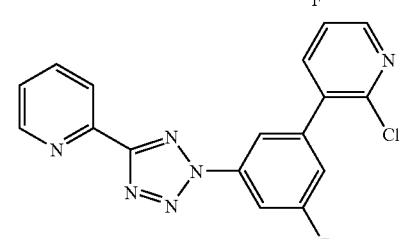
-continued
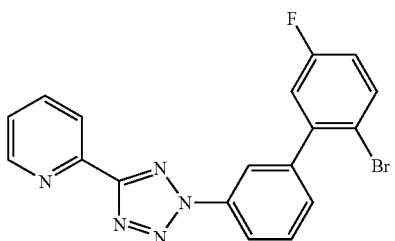
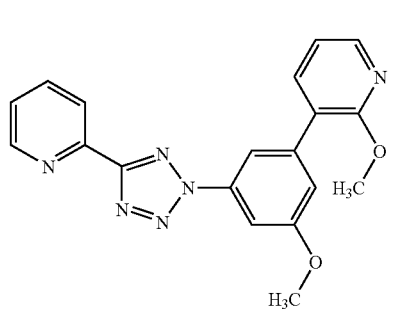
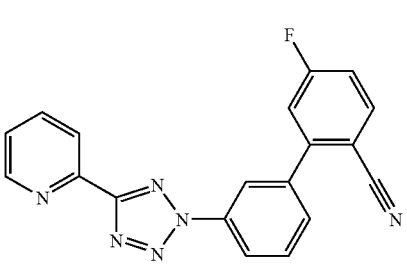
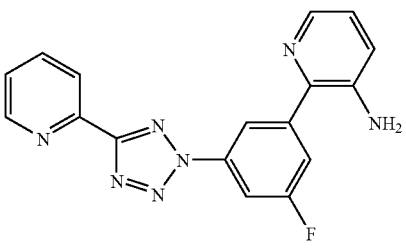
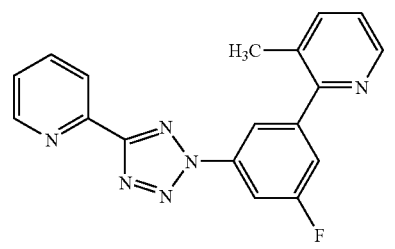
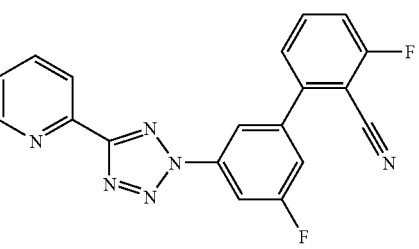

-continued
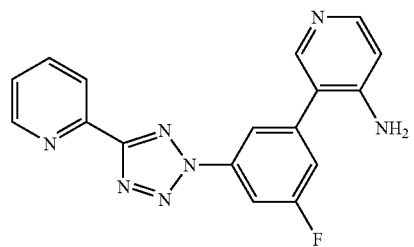
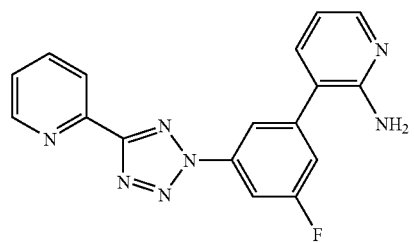
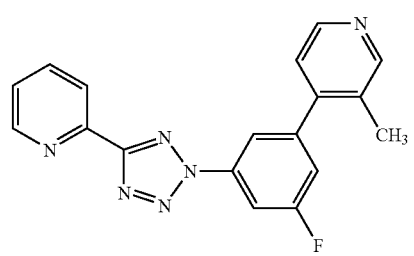
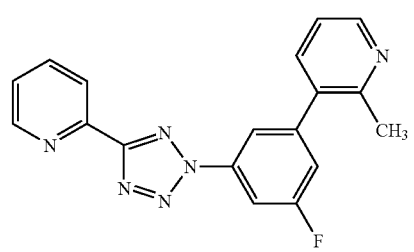
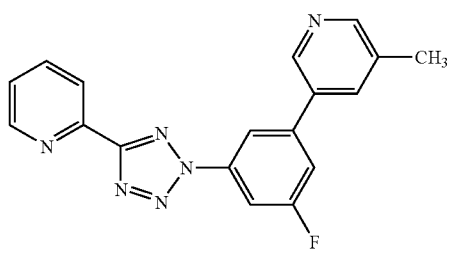
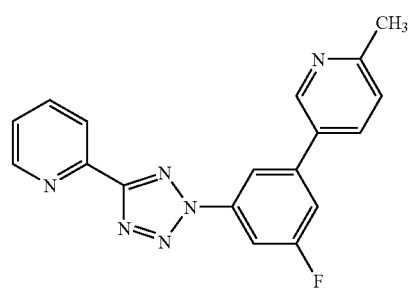
-continued
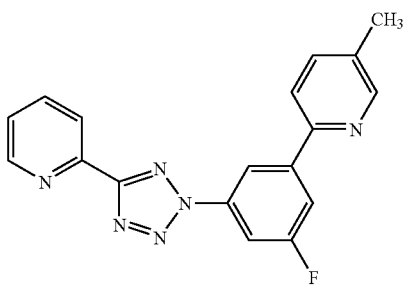
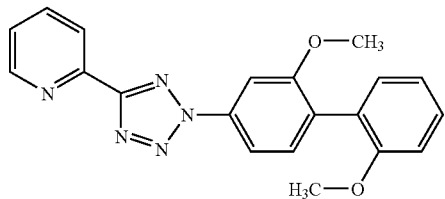
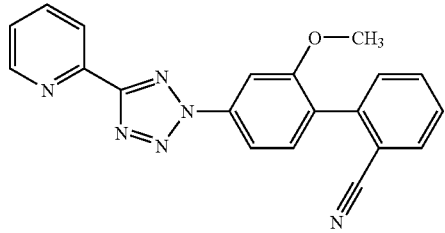
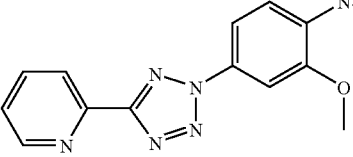
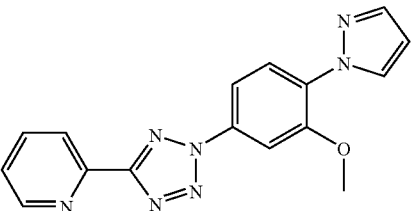
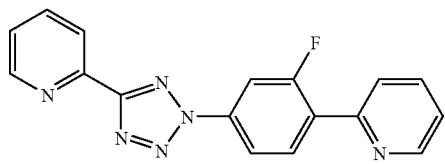
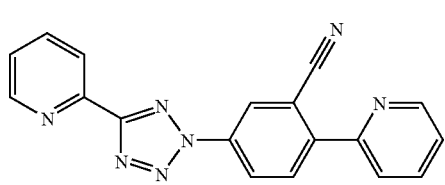

-continued
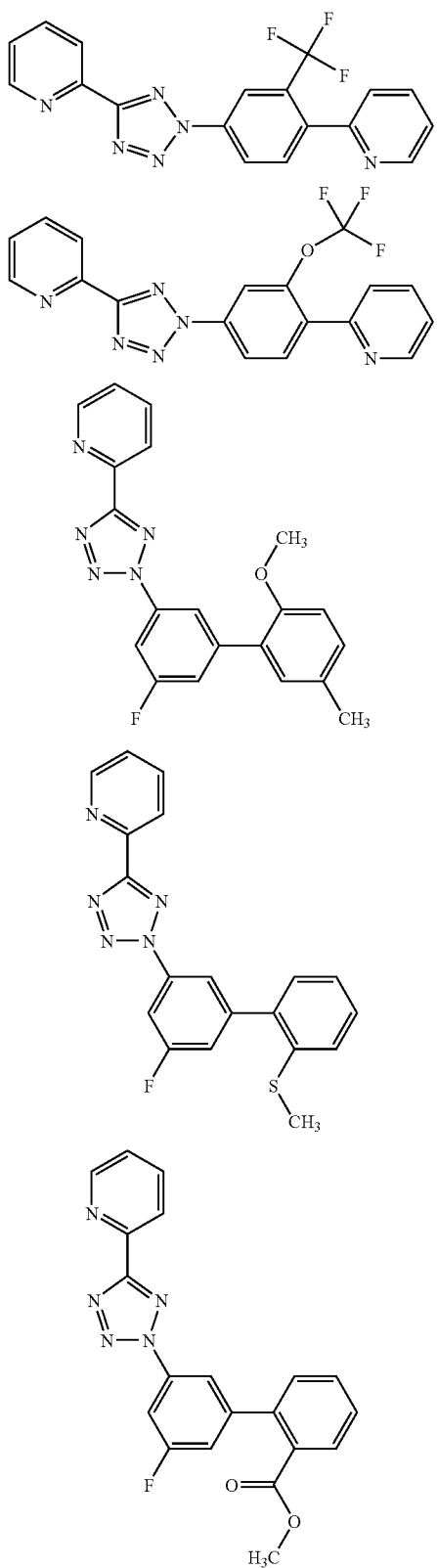
-continued
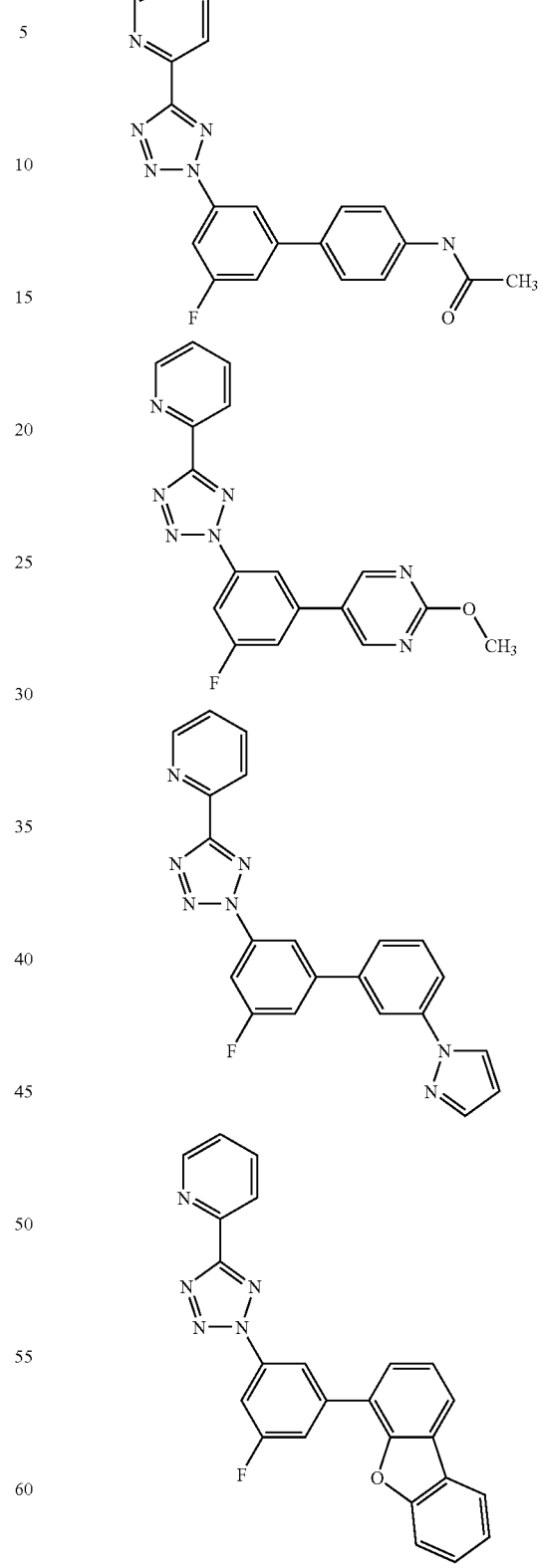

-continued
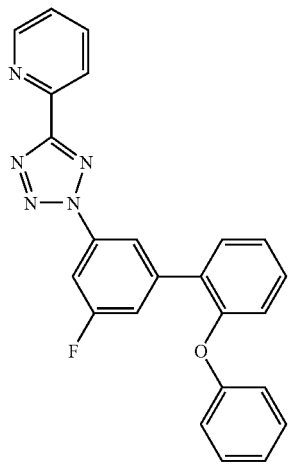
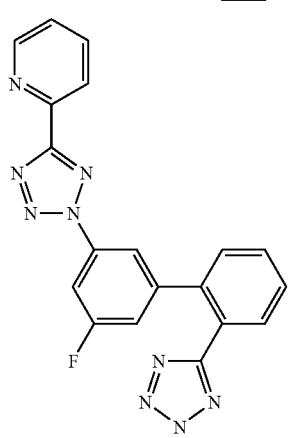
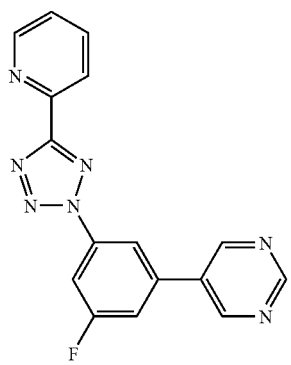
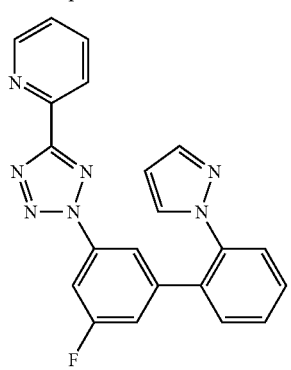
-continued
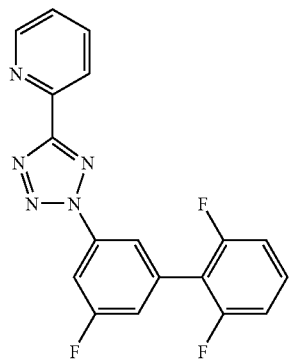
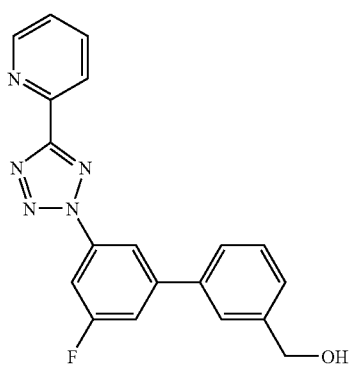
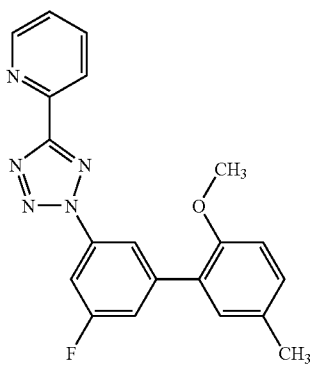
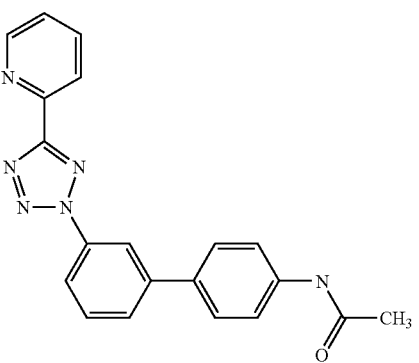

201
-continued
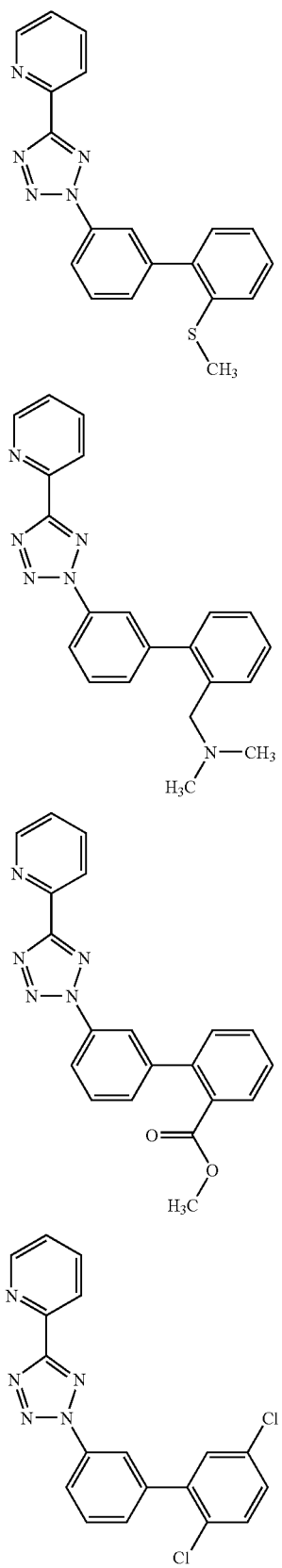
202
-continued
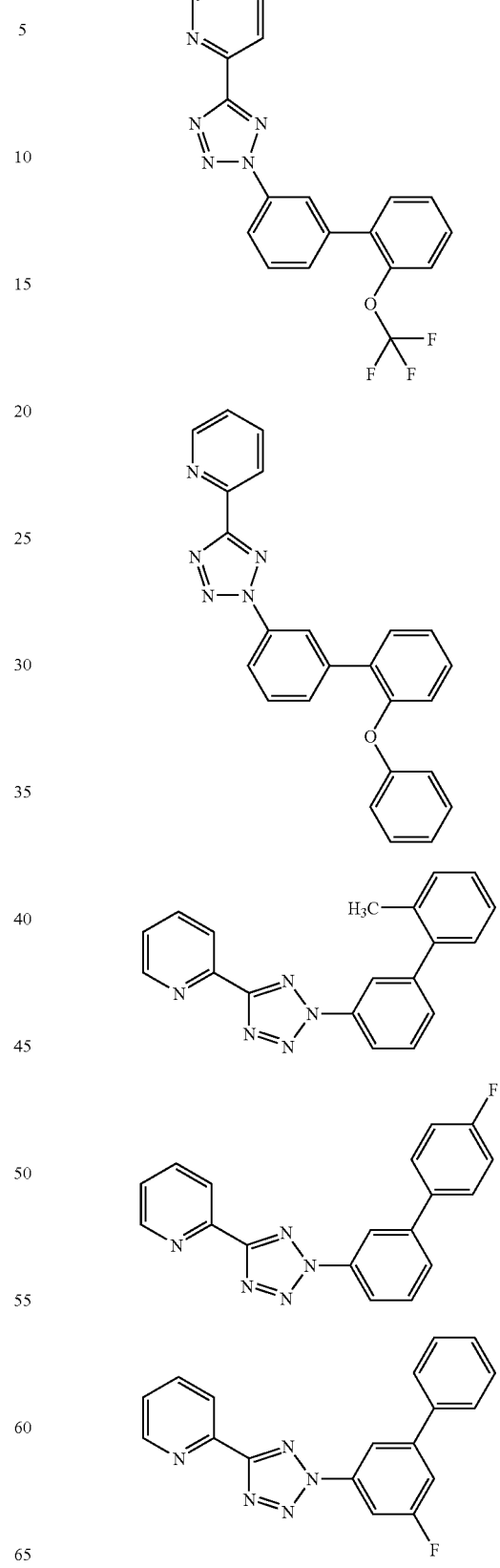

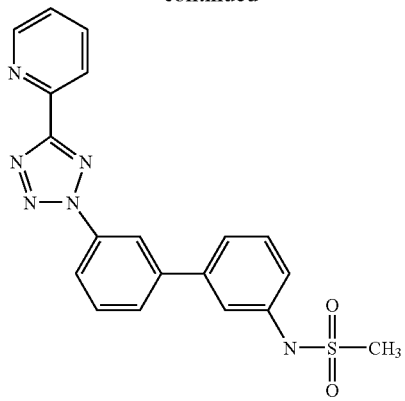
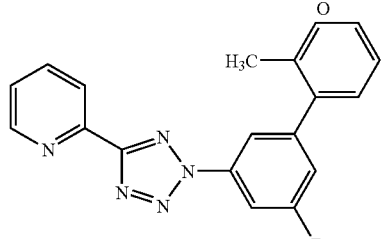
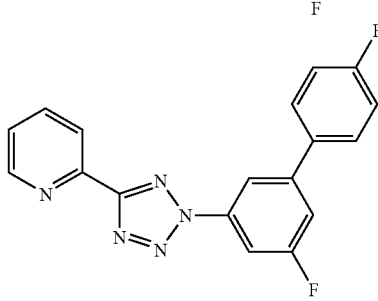
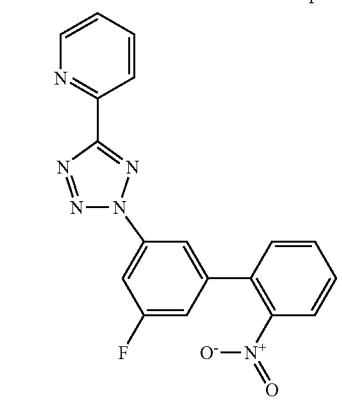
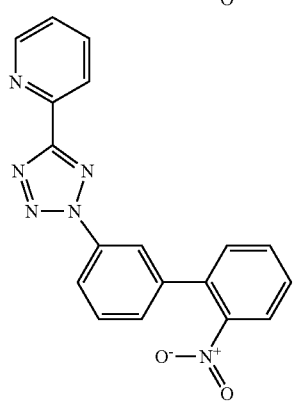
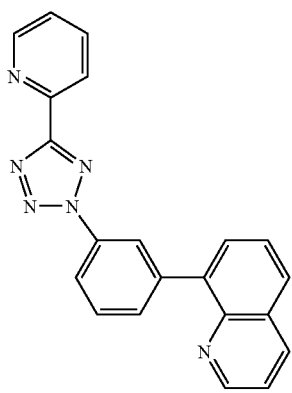
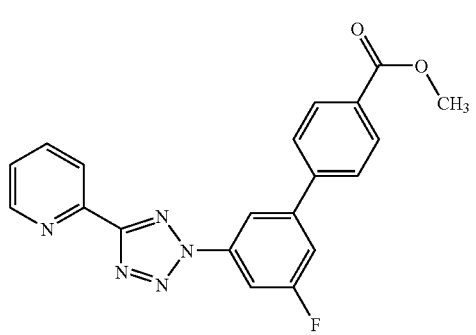
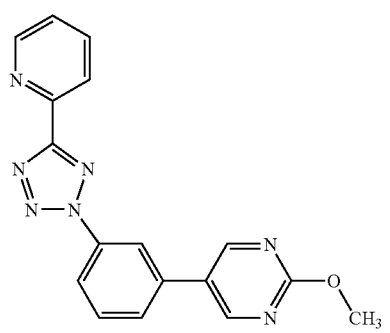
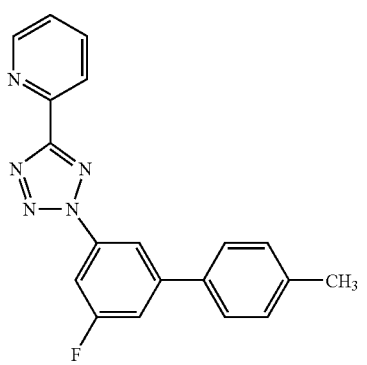

-continued
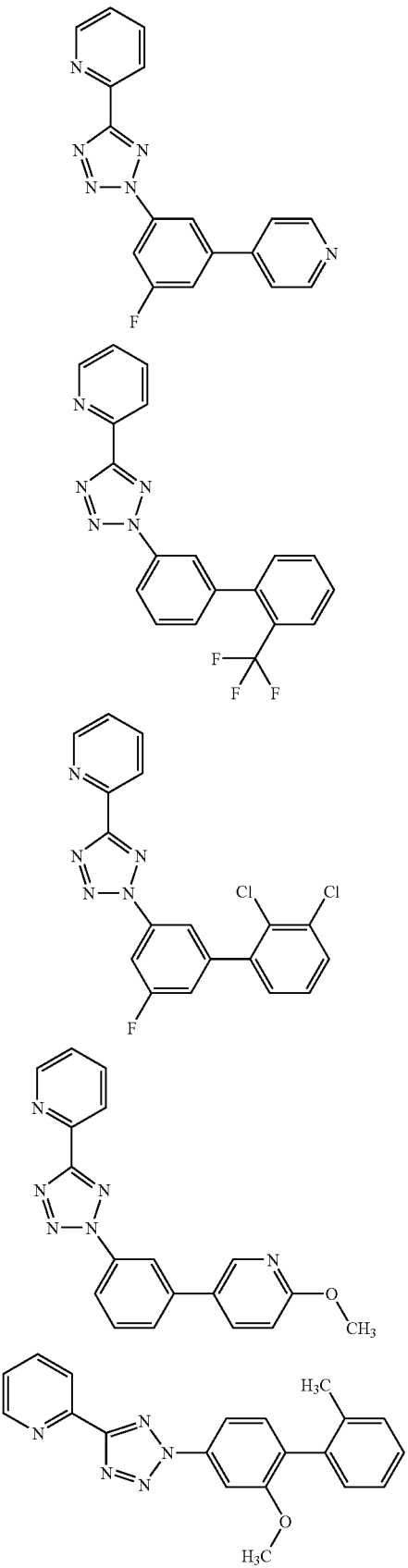
-continued
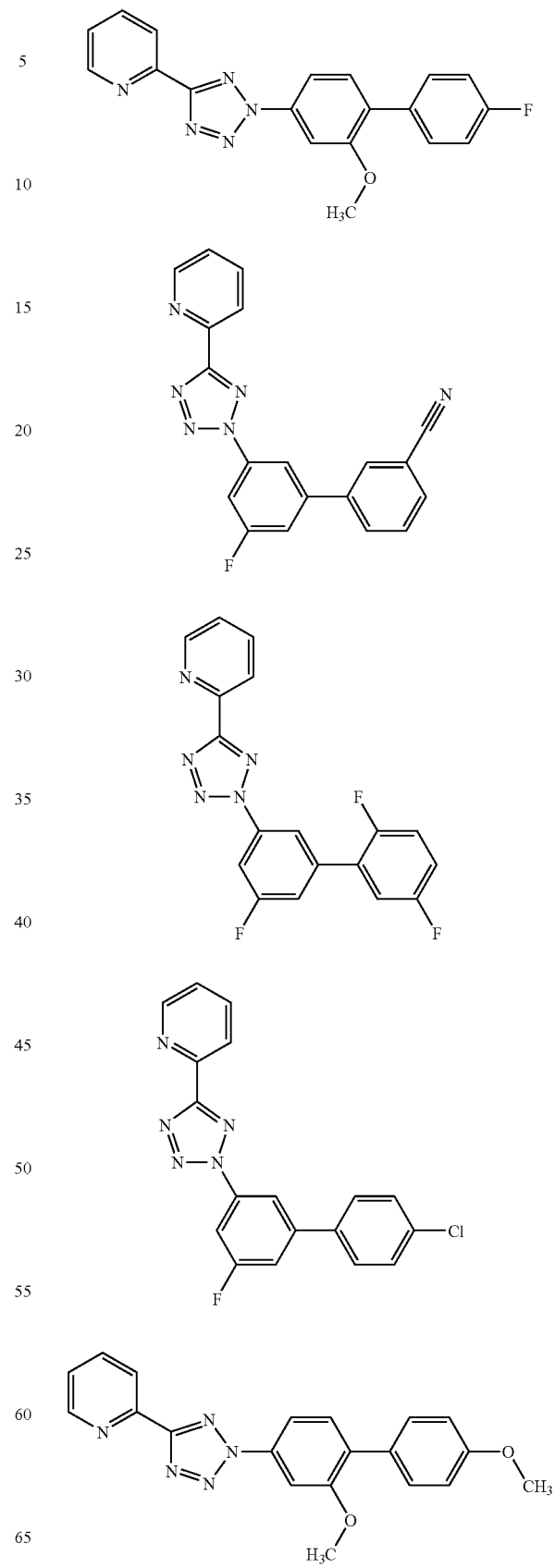

-continued
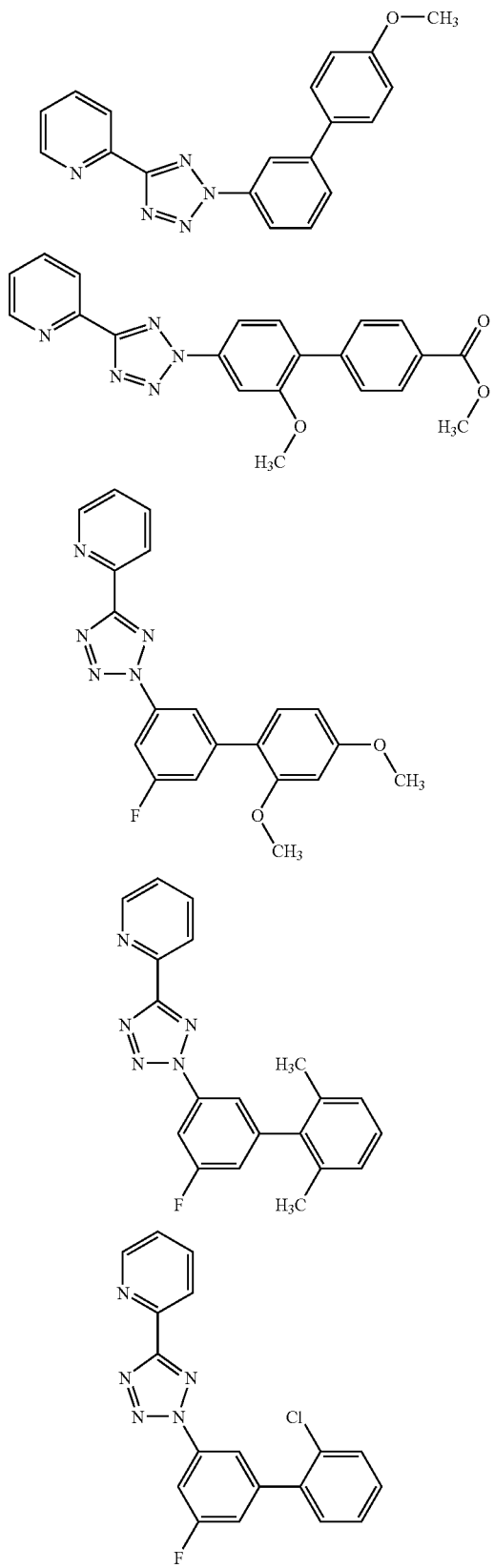
-continued
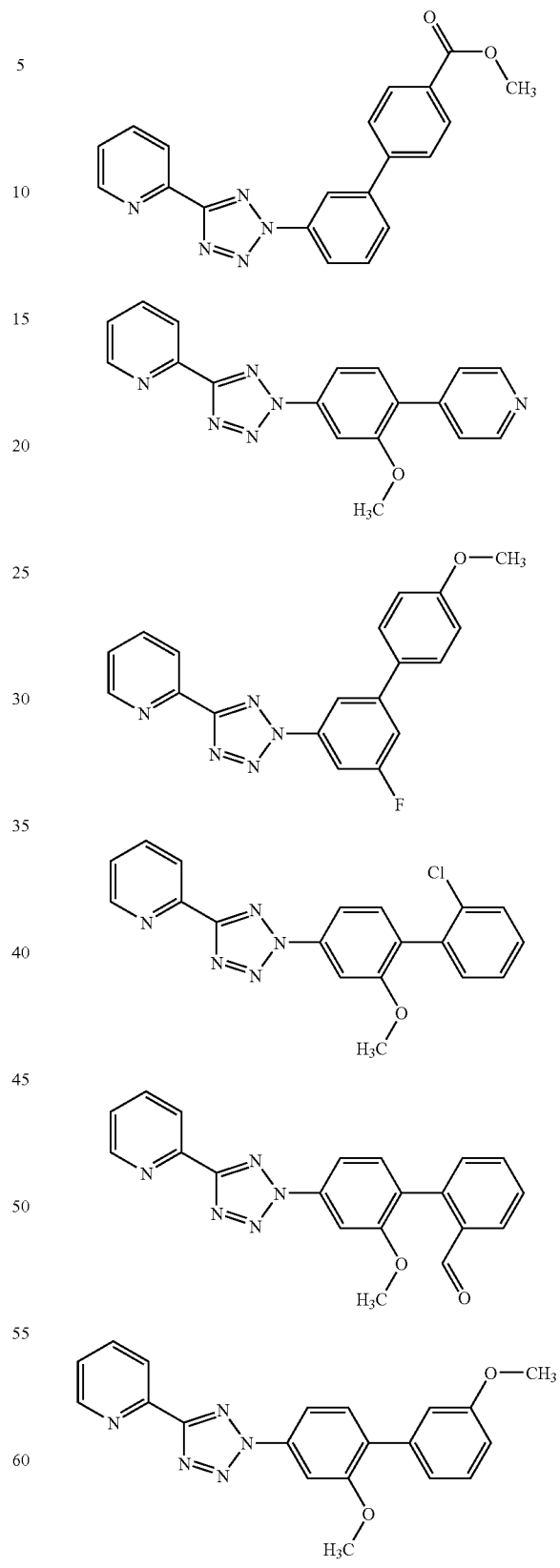

-continued
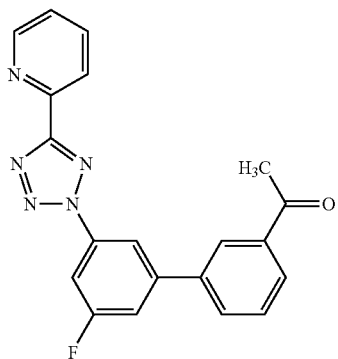
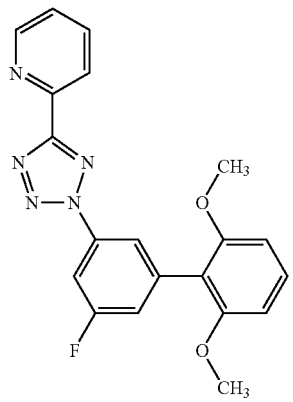
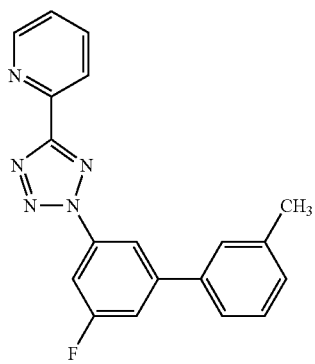
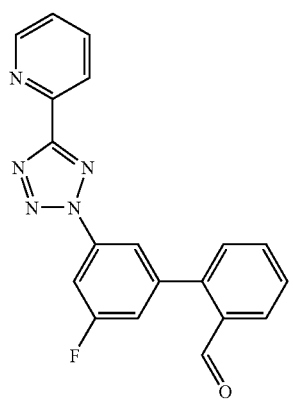
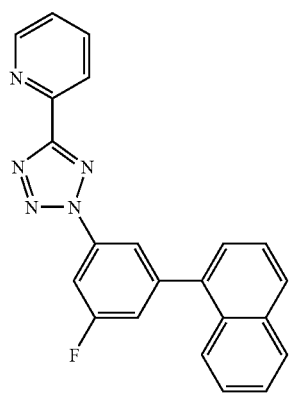
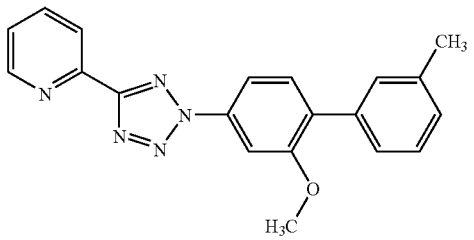
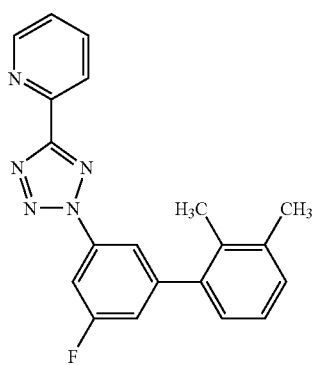
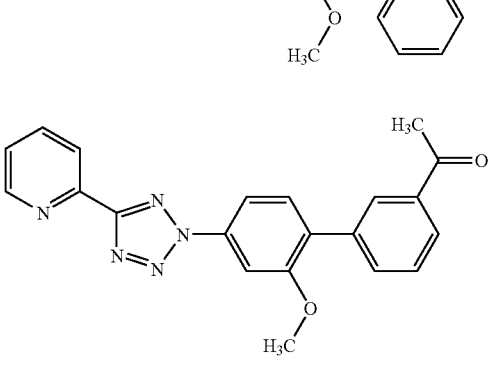

211
-continued
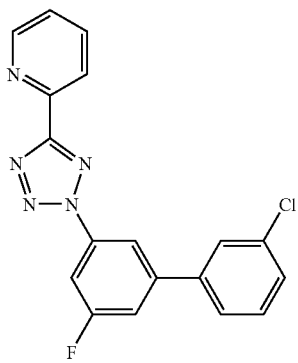
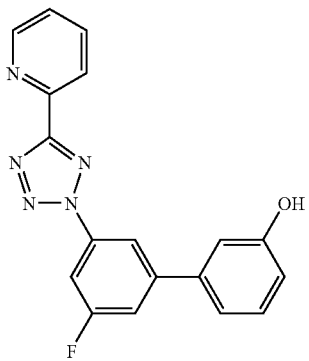
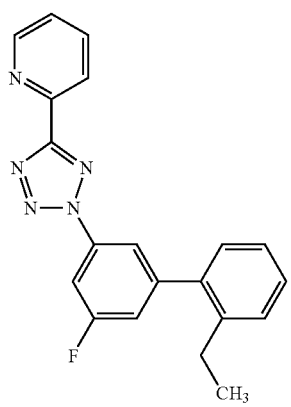
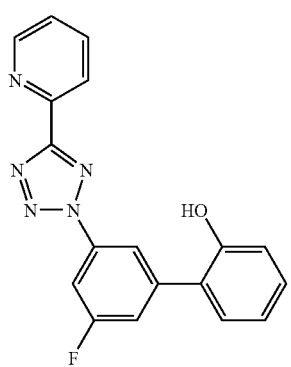
212
-continued
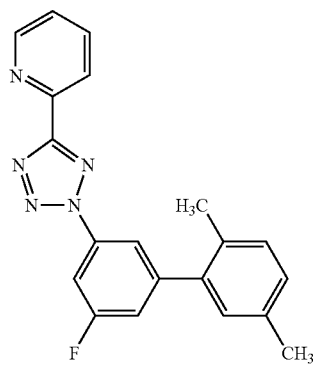
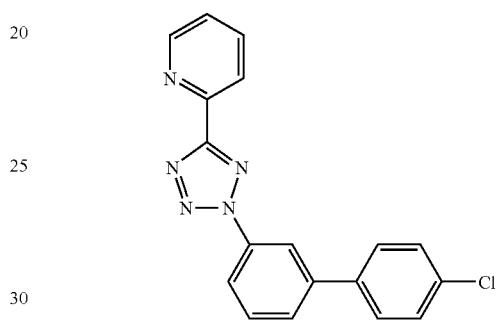
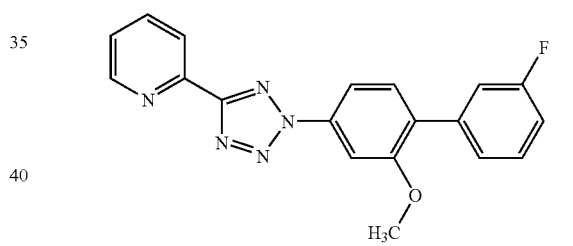
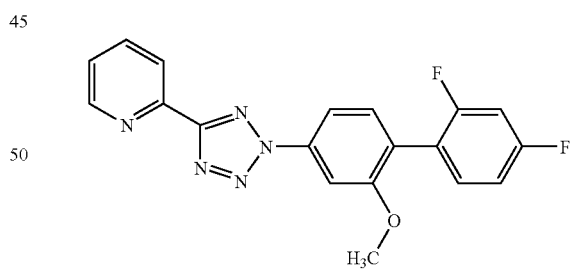
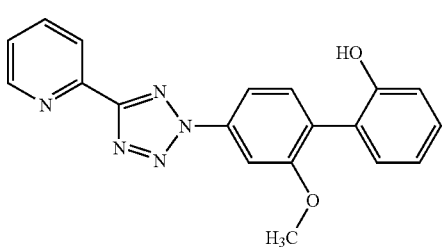

-continued
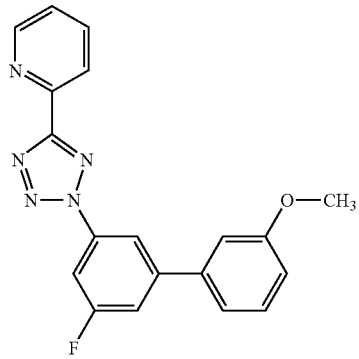
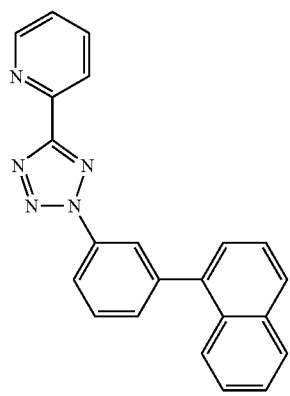
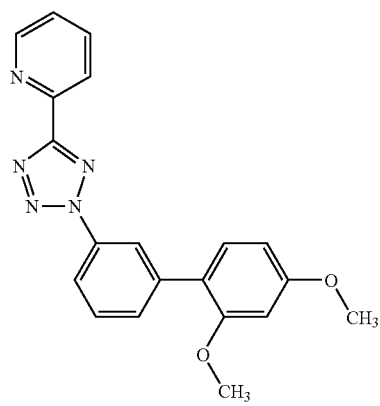
-continued
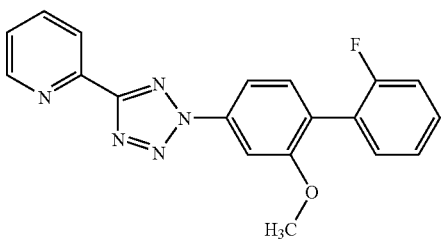
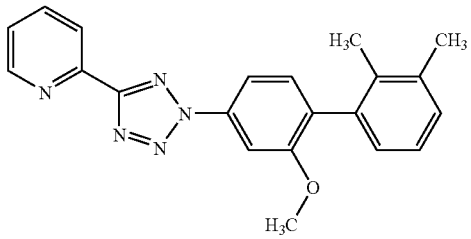
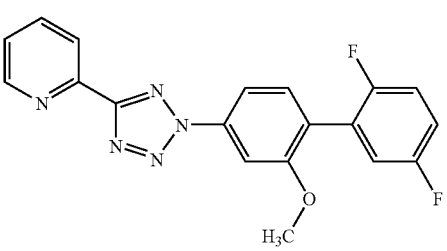

-continued
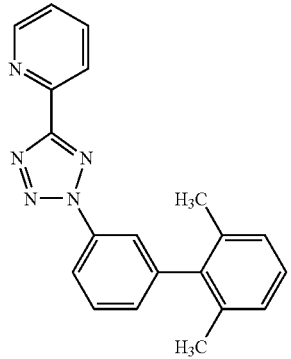
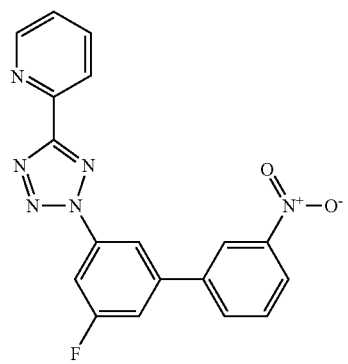
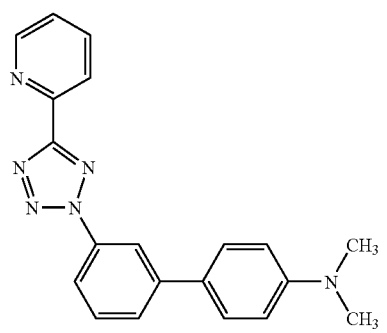
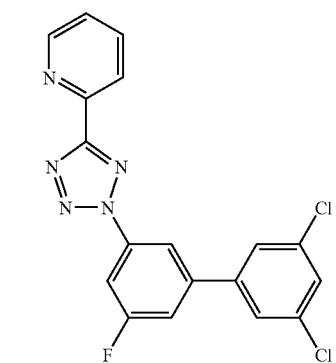
-continued
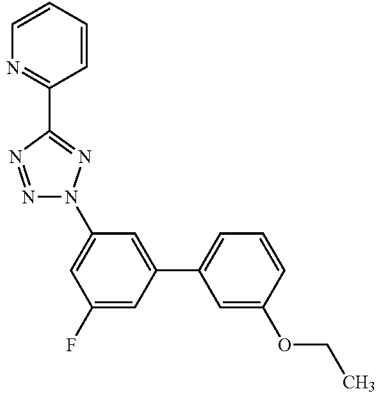
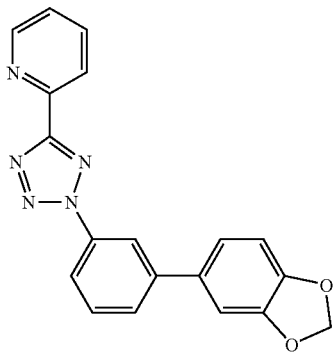
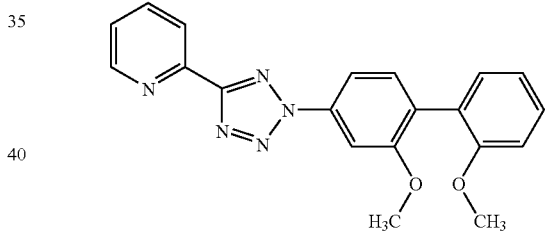
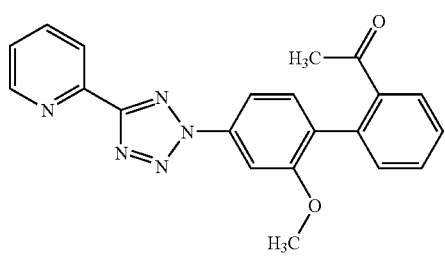
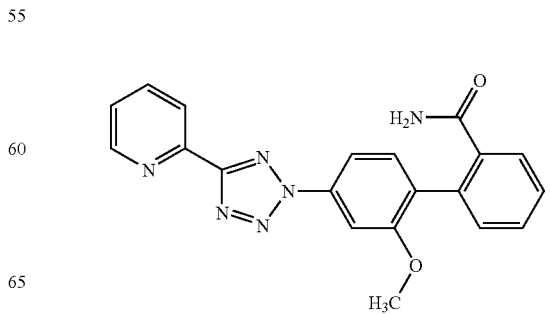

217
-continued
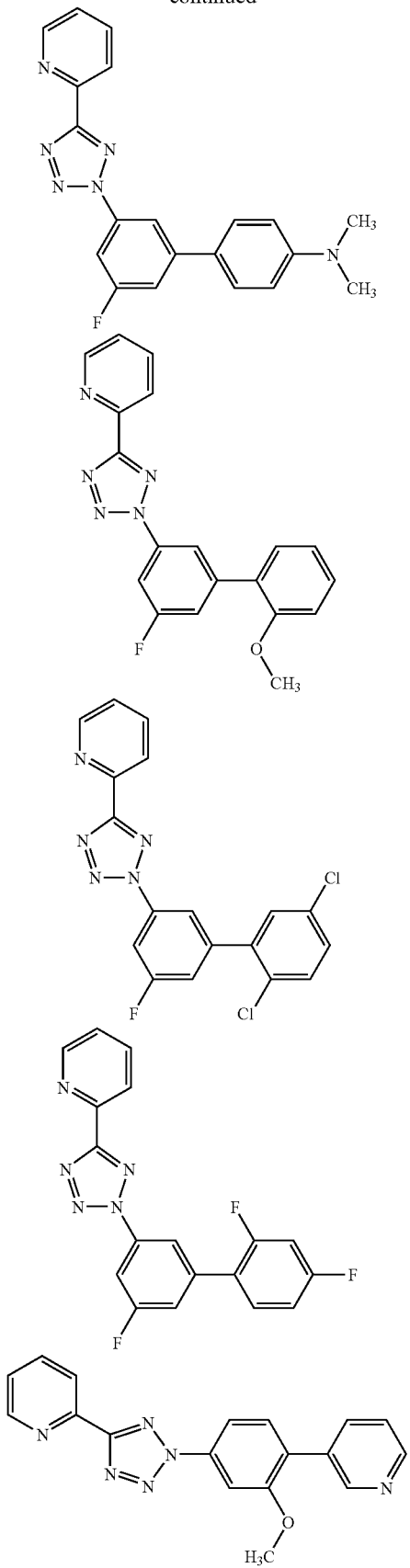
218
-continued
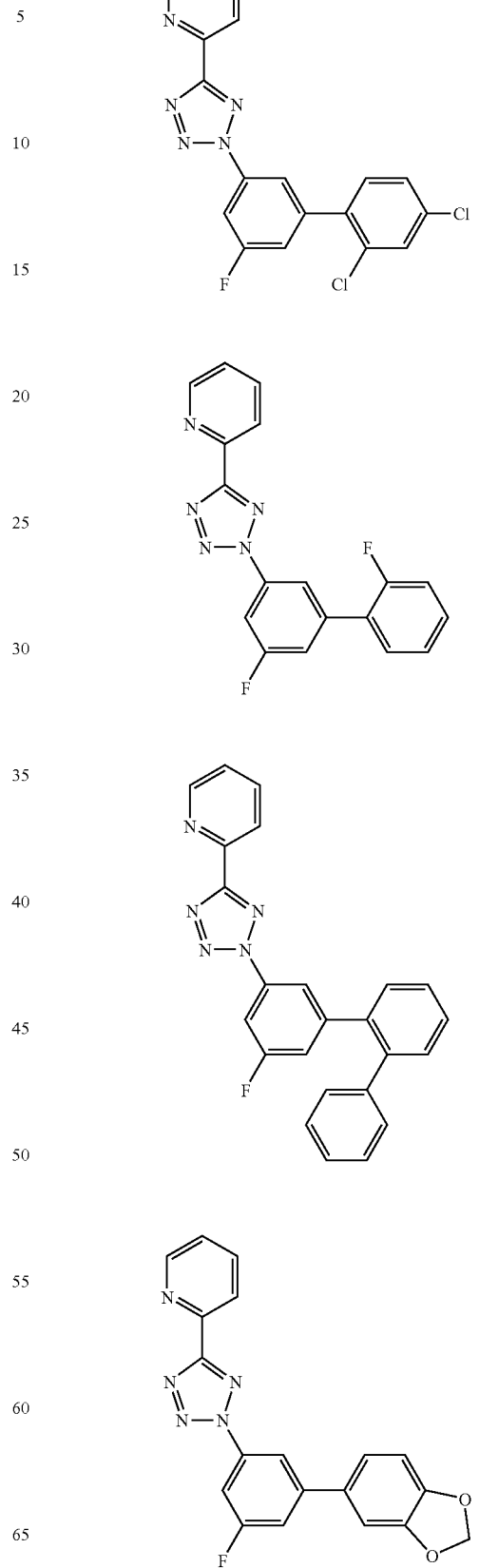

219
-continued
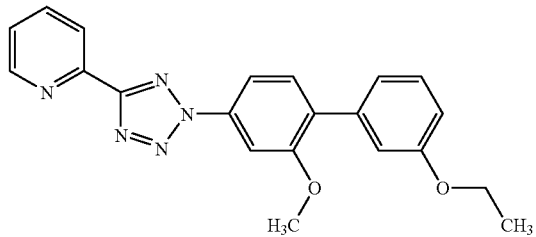
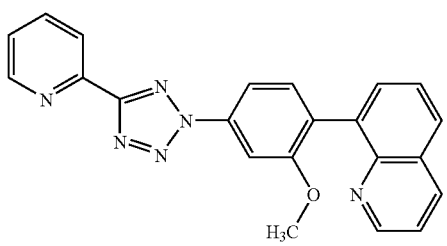
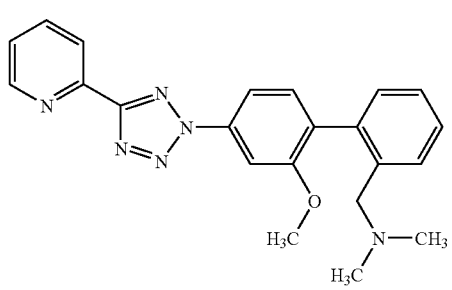
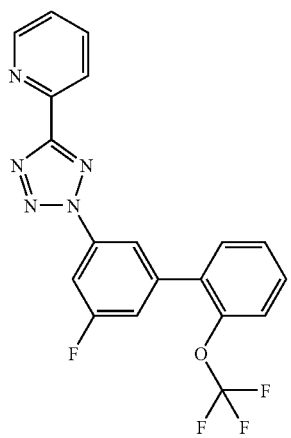
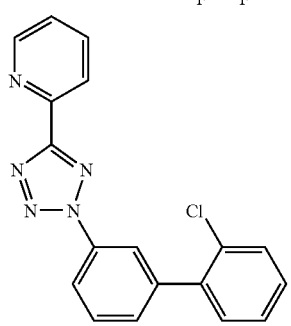
220
-continued
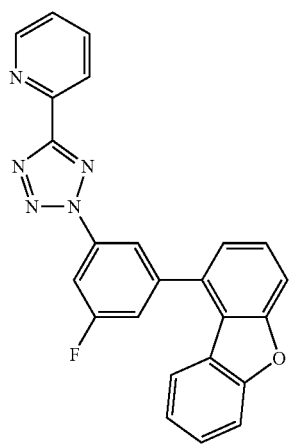
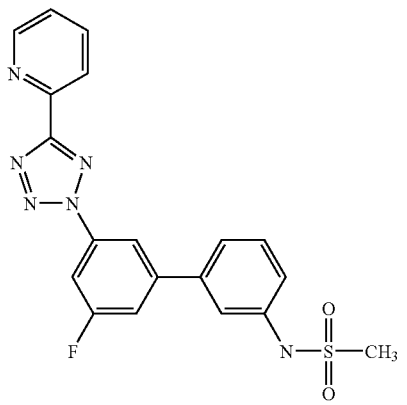
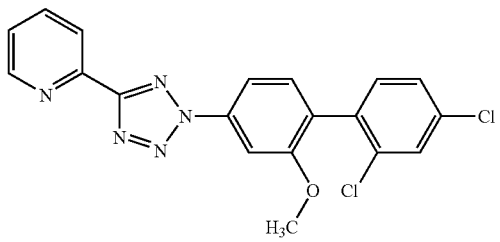
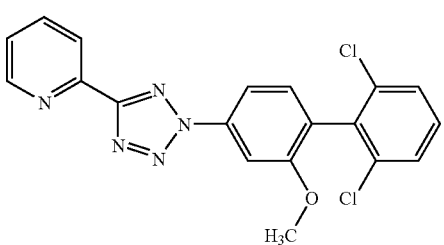

221
-continued
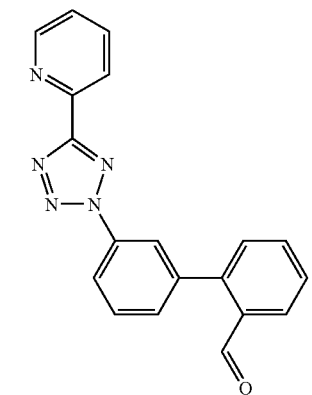
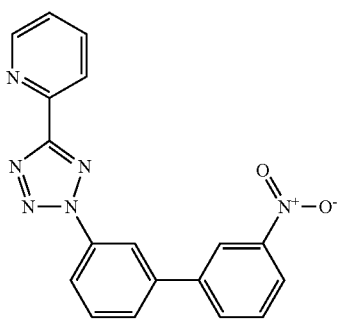
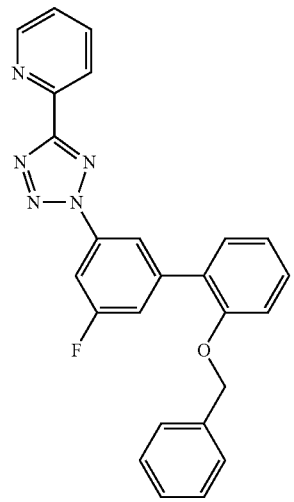
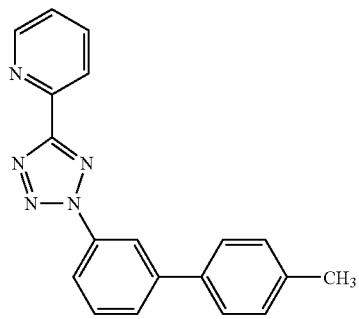
222
-continued
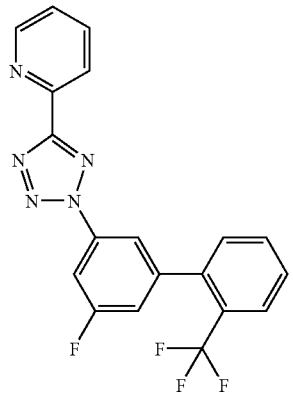
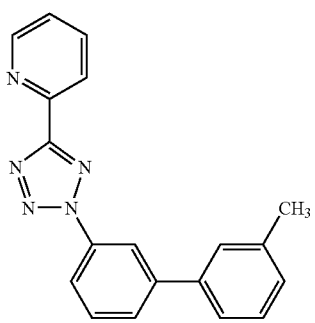
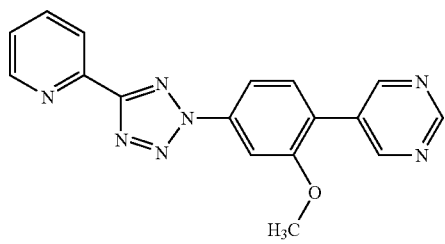
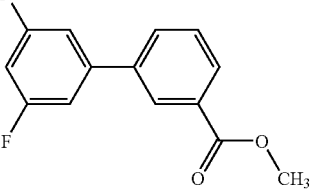
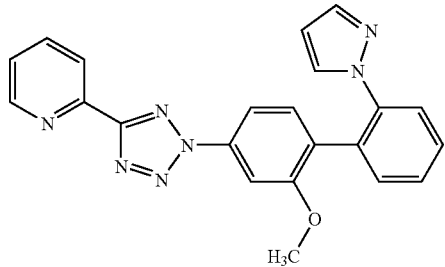

223
-continued
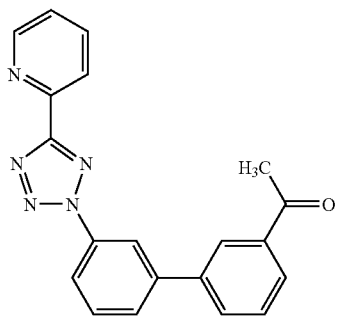
224
-continued
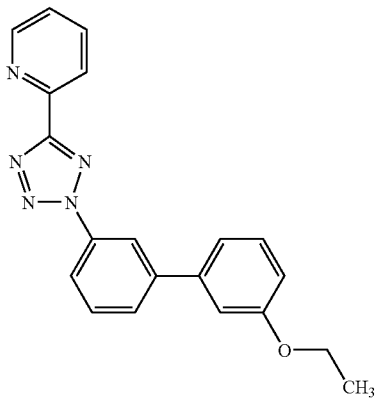
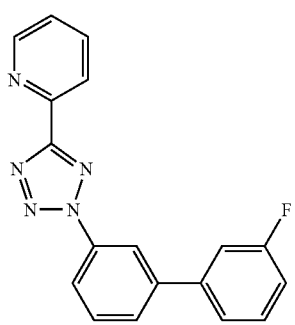
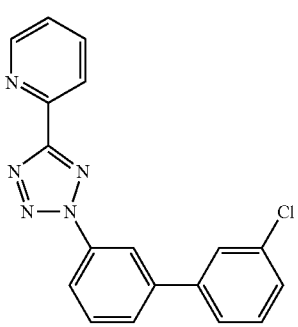
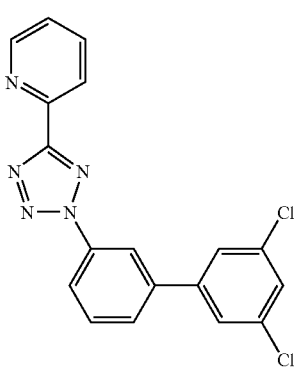

-continued
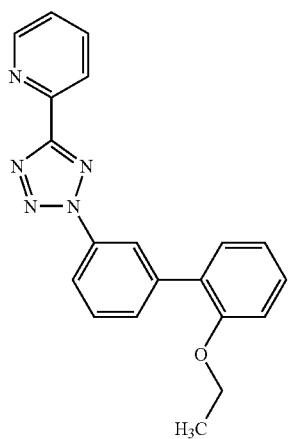
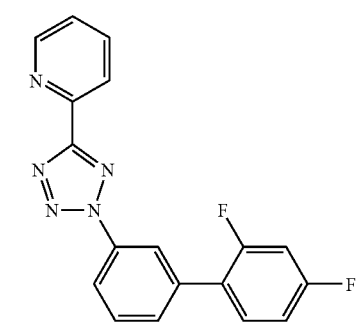
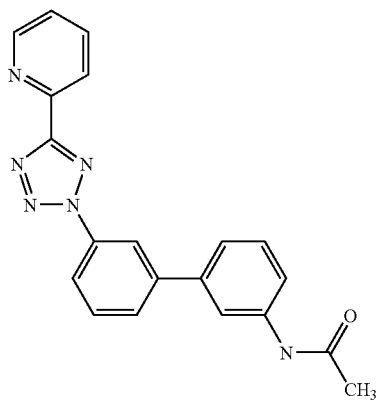
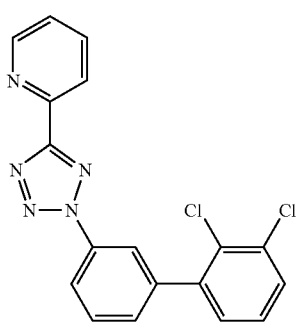
-continued
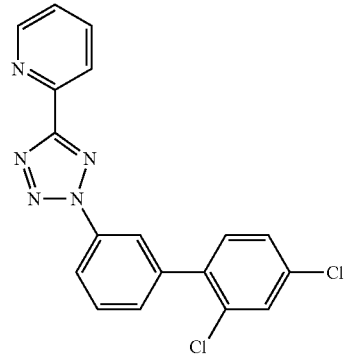
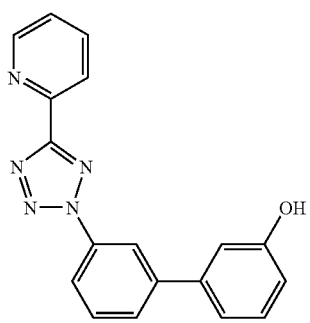
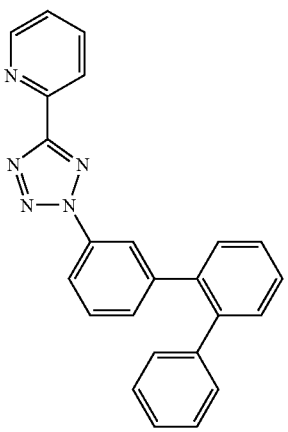
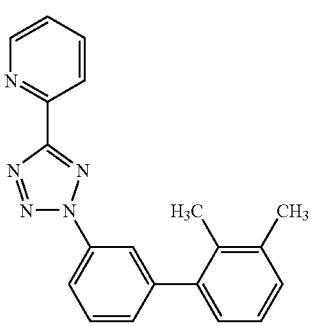

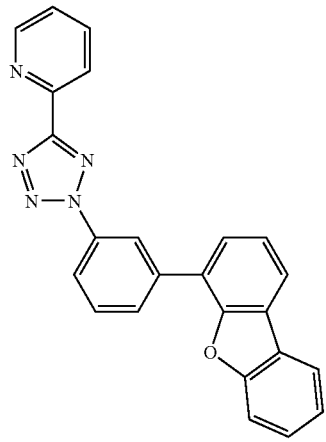
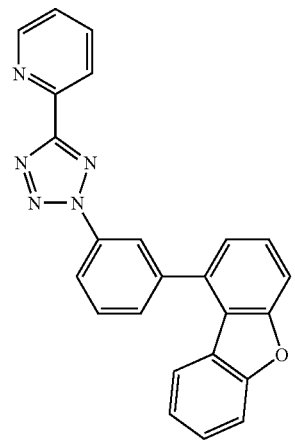
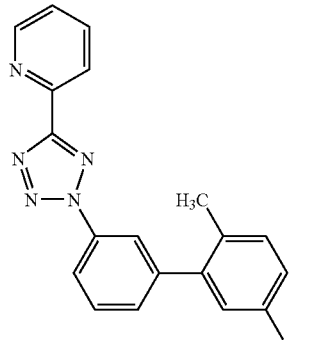
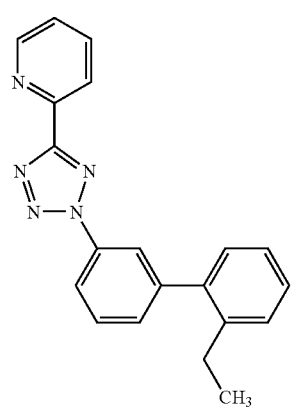
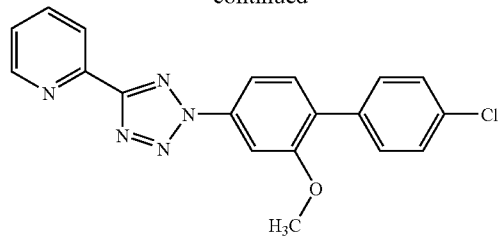
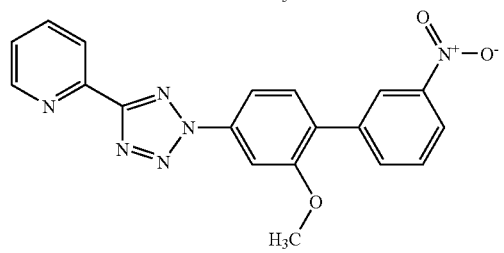
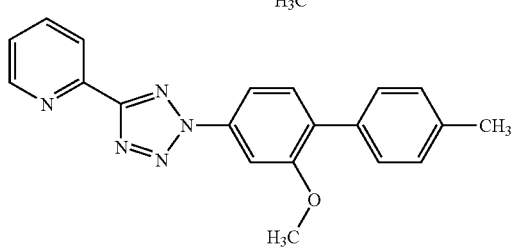
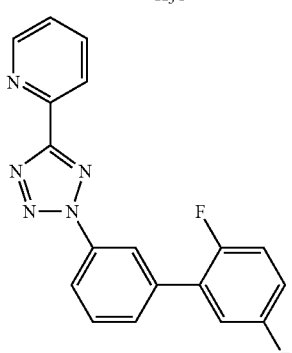
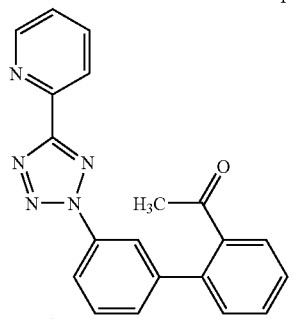
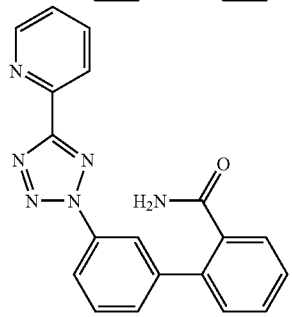

-continued
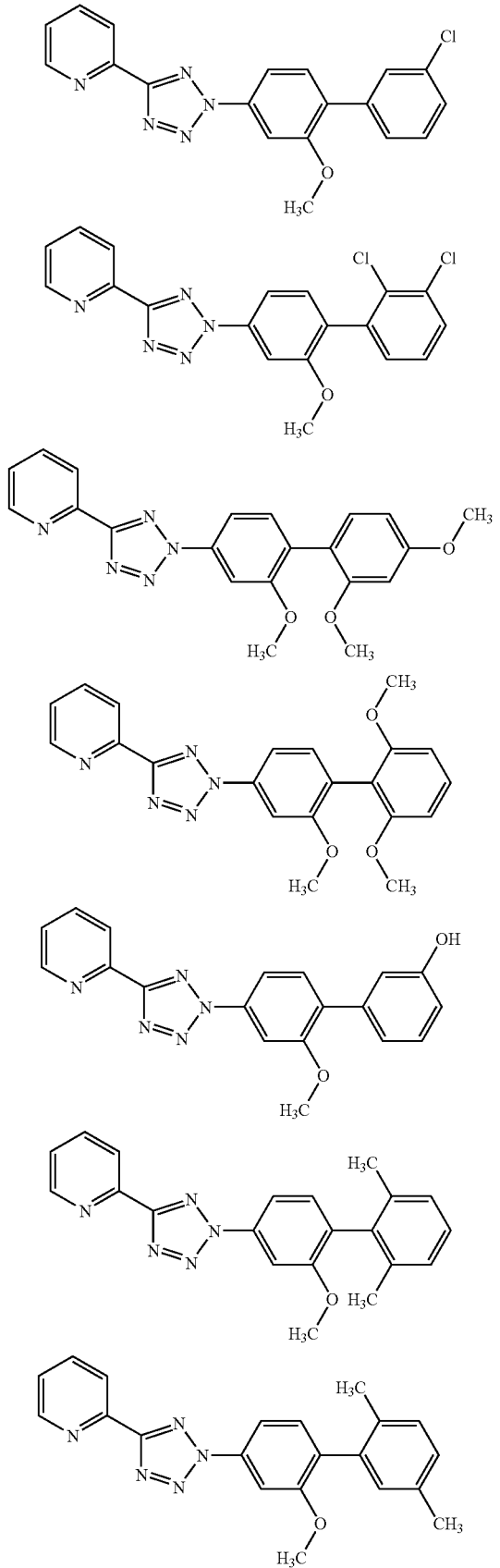
-continued
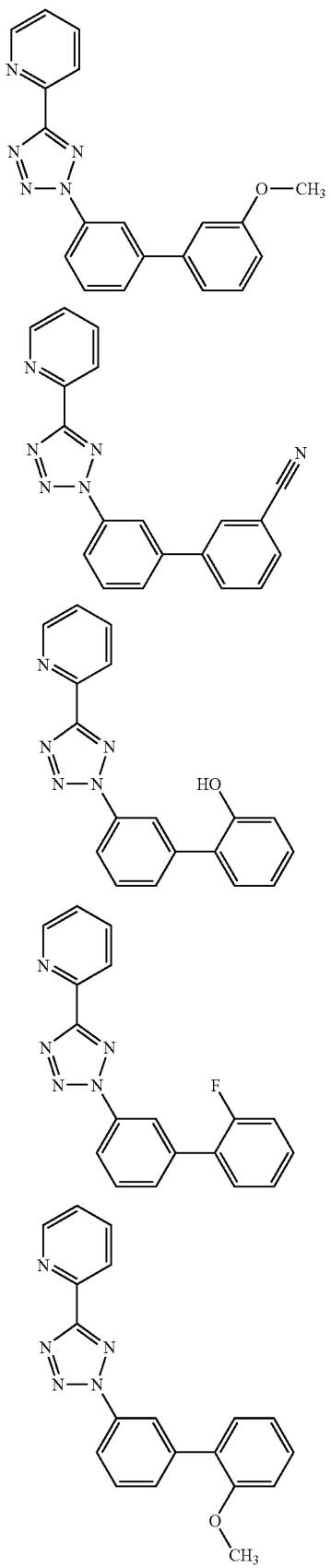

-continued
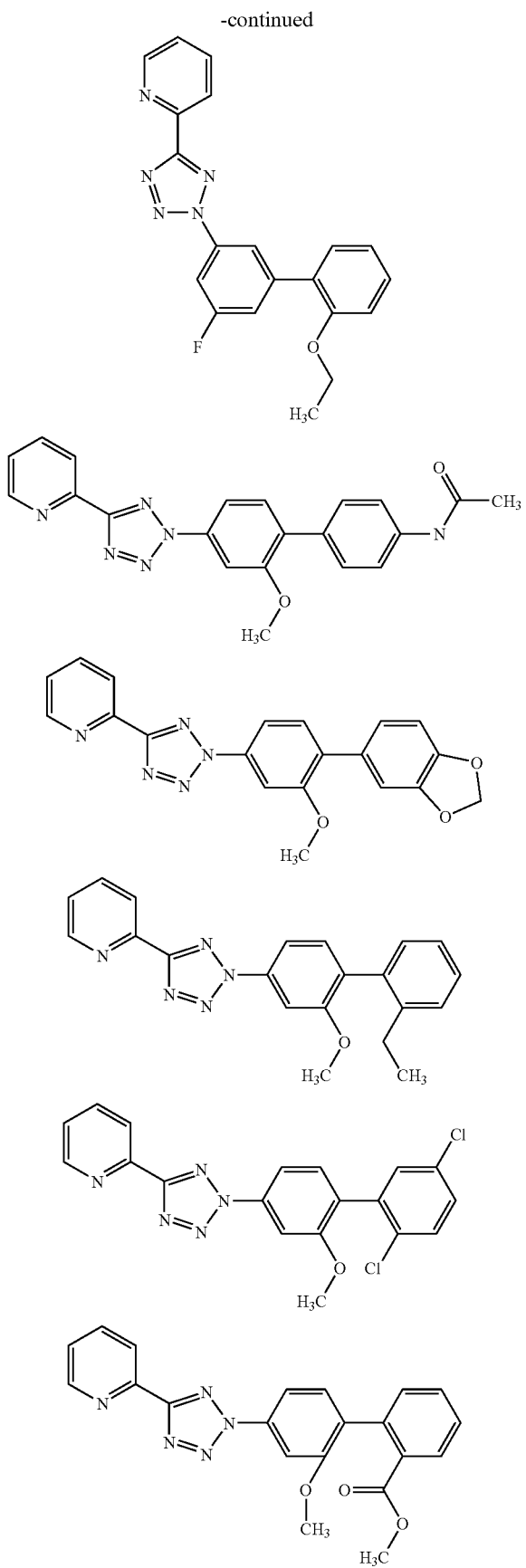
-continued
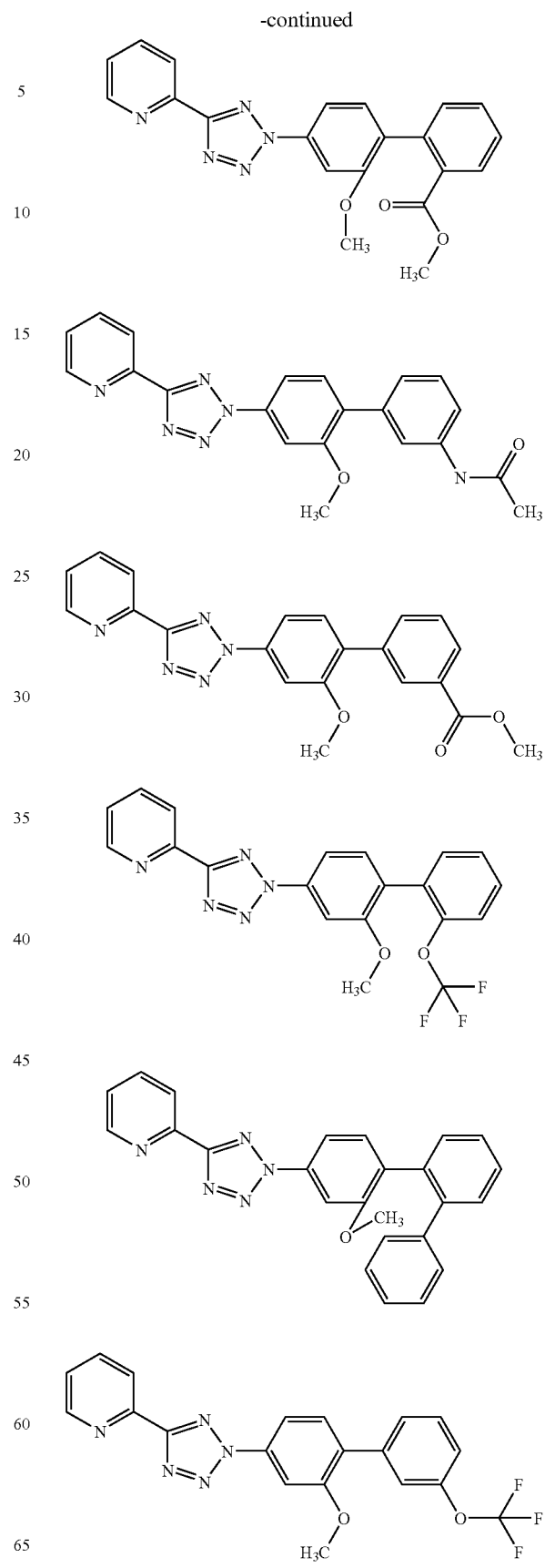

-continued

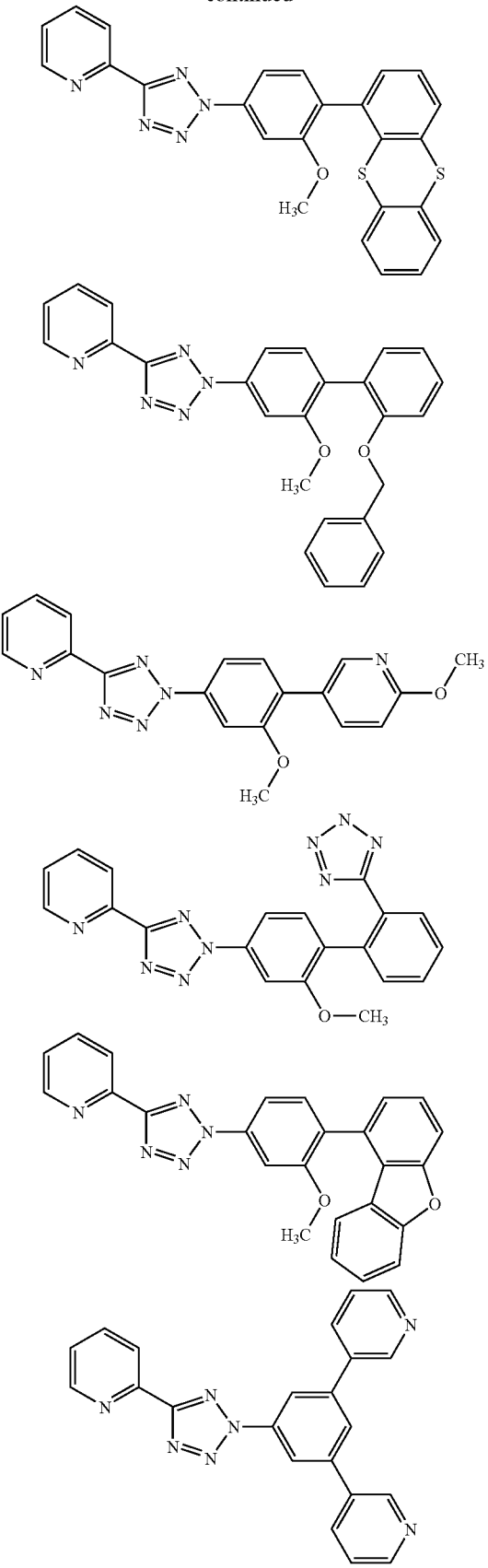

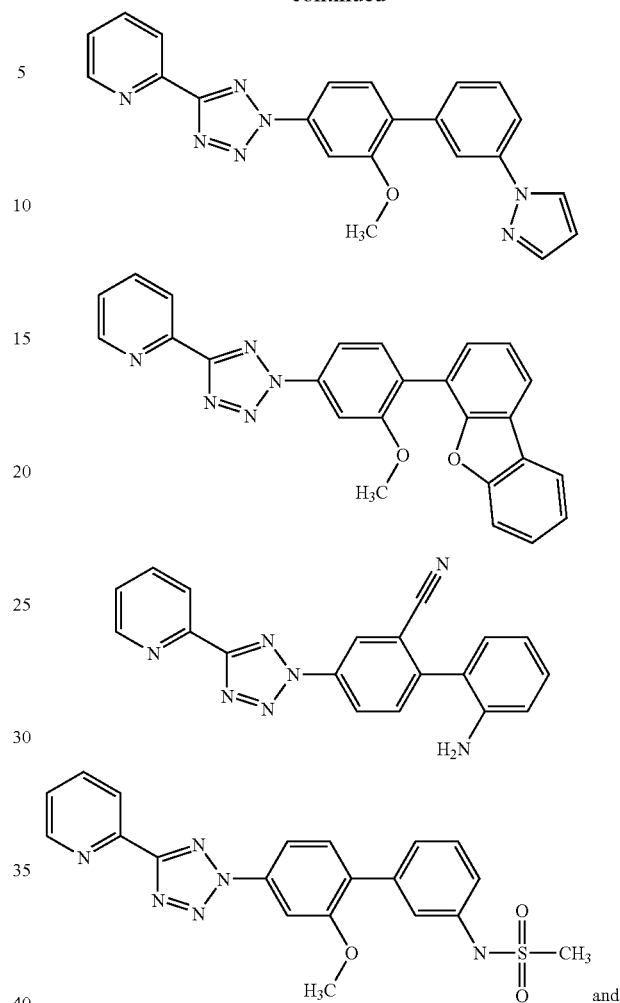

or a pharmaceutically acceptable salt thereof.

7. A pharmaceutical composition comprising the compound of claim 1, or a pharmaceutically acceptable salt thereof, and a pharmaceutically acceptable carrier.

8. A pharmaceutical composition comprising the compound of claim 5, or a pharmaceutically acceptable salt thereof, and a pharmaceutically acceptable carrier.

9. A pharmaceutical composition comprising the compound of claim 6, or a pharmaceutically acceptable salt thereof, and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,592,337 B2 | Page 1 of 1 |
| APPLICATION NO. | : 10/506479 | |
| DATED | : September 22, 2009 | |
| INVENTOR(S) | : Chen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1406 days.

Signed and Sealed this

Twenty-eighth Day of September, 2010

David J. Kappos
*Director of the United States Patent and Trademark Office*